US007890313B2

(12) United States Patent
Kita et al.

(10) Patent No.: US 7,890,313 B2
(45) Date of Patent: Feb. 15, 2011

(54) METHOD AND APPARATUS FOR ANALYSIS OF MOLECULAR COMBINATION BASED ON COMPUTATIONS OF SHAPE COMPLEMENTARITY USING BASIS EXPANSIONS

(75) Inventors: David Kita, Milpitas, CA (US); Somalee Datta, Menlo Park, CA (US); Adityo Prakash, Fremont, CA (US); Eniko Fodor, Fremont, CA (US)

(73) Assignee: Verseon, Milpitas, CA (US)

( * ) Notice: Subject to any disclaimer, the term of this patent is extended or adjusted under 35 U.S.C. 154(b) by 1215 days.

(21) Appl. No.: 10/966,160

(22) Filed: Oct. 14, 2004

(65) Prior Publication Data

US 2005/0119834 A1  Jun. 2, 2005

Related U.S. Application Data

(60) Provisional application No. 60/511,477, filed on Oct. 14, 2003.

(51) Int. Cl.
*G06G 7/48* (2006.01)
*G01N 33/48* (2006.01)
*G01N 19/00* (2006.01)
*G06G 7/58* (2006.01)

(52) U.S. Cl. .............................. 703/11; 702/19; 702/27; 703/12

(58) Field of Classification Search ........................ None
See application file for complete search history.

(56) References Cited

U.S. PATENT DOCUMENTS

| 6,230,102 B1 | 5/2001 | Tidor et al. |
|---|---|---|
| 2003/0046011 A1 | 3/2003 | Friedman |
| 2003/0216867 A1 | 11/2003 | Campbell et al. |

OTHER PUBLICATIONS

Combet et al. "geno3D: automatic comparative molecular modeling of protein" Bioinformatics (2002) vol. 18, pp. 213-214.*
Sobolev et al., "Molecular Docking Using Surface Complementarity," *Proteins: Structure, Function and Genetics*, 25:120-129 (1996).
Taylor et al., "DARWIN: A Program for Docking Flexible Molecules," *Proteins: Structure, Function and Genetics*, 41(2):173-191 (2000).
Wang et al., "Flexible Ligand Docking: A Multistep Strategy Approach," *Proteins: Structure, Function and Genetics*, 36:1-19 (1999).
Waszkowycz et al., "Large-scale virtual screening for discovering leads in the post-genomic era," *IBM Systems Journal*, 40(2):360-376 (2001).
Welch et al., "Hammerhead: fast, fully automated docking of flexible ligands to protein binding sites," *Chemistry & Biology*, 3:449-462 (1996).
Abagyan et al., "ICM—A New Method for Protein Modeling and Design: Applications to Docking and Structure Prediction from the Distorted Native Conformation," *J. Comp. Chem.*, 15(5):488-506 (1994).
Abagyan et al., "High-throughput docking for lead generation," *Current Opinion in Chemical Biology*, 5(4):375-382 (2001).
Bohacek et al., "Multiple Highly Diverse Structures Complementary to Enzyme Binding Sites: Results of Extensive Application of a de Novo Design Method incorporating Combinatorial Growth," *J. American Chemical Society*, 116:5560-5571 (1994).
Bohm, H. J., "The Computer program LUDI: a new method for the de novo design of enzyme inhibitors," *J. Computer-Aided Molecular Design*, 6:61-78 (1992).
Clark et al., "Validation of the General Purpose Tripos 5.2 Force Field," *J. Comp. Chem.*, 10(8):982-1012 (1989).
Clauben et al., "FlexE: Efficient Molecular Docking Considering Protein Structure Variations," *J. Molecular Biology*, 308:377-395 (2001).
Connolly, M. L., "Analytical molecular surface calculation," *J. Applied Crystallography*, 16:548-558 (1983).
Desjarlais et al., "Docking Flexible Ligands to Macromolecular Receptors by Molecular Shape," *J. Med. Chem.*, 29:2149-2153 (1986).
Di Nola et al., "Molecular Dynamics Simulation of the Docking of Substrates to Proteins," *Proteins: Structure, Function and Genetics*, 19:174-182 (1994).
Drews, J., "Drug Discovery: A Historical perspective," *Science*, 287(5460):1960-1964 (2000).
Ewing et al., "Critical Evaluation of Search Algorithms for Automated Molecular Docking and Database Screening," *J. Computational Chemistry*, 18(9):1175-1189 (1997).
Fischer et al., "Surface Motifs by a Computer Vision Technique: Searches, Detection, and Implications for Protein-Ligand Recognition," *Proteins: Structure, Function and Genetics*, 16:278-292 (1993).
Gabb et al., "Modelling Protein Docking using Shape Complementarity, Electrostatics and Biochemical Information," *J. Mol. Biol.*, 272(1):106-120 (1997).

(Continued)

*Primary Examiner*—Eric S. DeJong
(74) *Attorney, Agent, or Firm*—Kilpatrick Townsend & Stockton LLP

(57) ABSTRACT

A method and apparatus for analysis of molecular combinations featuring two or more molecular subsets is described. The method computes the shape complementarity of the system utilizing a basis expansion representing molecular shapes of the first and second molecular subsets in a coordinate system. The precomputed sets of translated expansion coefficients for the first molecular subset are first constructed via application of a translation operator to a reference set of expansion coefficients and then stored on a computer recordable medium for later retrieval. Then, a shape complementarity score, representing a correlation of the first and second molecular subsets, is computed via suitable application of rotation operators to both the stored translated expansion coefficients of the first molecular subset and the reference expansion coefficients for the second molecular subset over the sequence of different sampled configurations for the molecular combination.

52 Claims, 17 Drawing Sheets

OTHER PUBLICATIONS

Goodsell et al., "Automated Docking of Substrates to Proteins by Simulated Annealing," *Proteins: Structure, Function, and Genetics*, 8:195-202 (1990).

Halgren et al., "Glide: A New Approach for Rapid, Accurate Docking and Scoring. 2. Enrichment Factors in Database Screening," *J. Med. Chem.*, 47(7):1750-1759 (2004).

Jones et al., "Molecular Recognition of Receptor Sites using a Genetic Algorithm with a Description of Desolvation," *J. Mol. Biol.*, 245:43-53 (1995).

Jones et al., "Development and Validation of a Genetic Algorithm for Flexible Docking," *J. Mol. Biol.*, 267:727-748 (1997).

Kastenholz et al., "GRID/CPCA: A New Computational Tool to Design Selective Ligands," *J. Medical Chemistry*, 43:3033-3044 (2000).

Katchalski-Katzir et al., "Molecular surface recognition: Determination of geometric fit between proteins and their ligands by correlation techniques," *PNAS*, 89(6):2195-2199 (1992).

Kramer et al., "Evaluation of the FlexX Incremental Construction Algorithm for Protein-Ligand Docking," *Proteins: Structure, Function and Genetics*, 37:228-241 (1999).

Lamb et al., "Design, docking, and evaluation of multiple libraries against multiple targets," *Proteins: Structure, Function and Genetics*, 42:296-318 (2001).

Lawrence et al., "CLIX: A Search Algorithm for Finding Novel Ligands Capable of Binding Proteins of Known Three-Dimensional Structure," *Proteins: Structure, Function and Genetics*, 12:31-41 (1992).

Leach et al., "Conformational Analysis of Flexible Ligands in Macromolecular Receptor Sites," *J. Comp. Chem.*, 13(6):730-748 (1992).

Lin et al., "Molecular Surface Representations by Sparse Critical Points," *Proteins: Structure, Function, and Genetics*, 18:94-101 (1994).

Luty et al., "Molecular Mechanics/Grid Method for the Evaluation of Ligand-Receptor Interactions," *J. Comp. Chem.*, 16(4):454-464 (1995).

Meng et al., "Orientational Sampling and Rigid-Body Minimization in Molecular Docking," *Proteins: Structure, Function, and Genetics*, 17:266-278 (1993).

Miller et al., "FLOG: a system to select 'qasi-flexible' ligands complementary to a receptor of known three-dimensional structure," *J. Computer-Aided Molecular Design*, 8(2):153-174 (1994).

Morris et al., "Automated Docking Using a Lamarckian Genetic Algorithm and an Empirical Binding Free Energy Function," *J. Comp. Chem.*, 19(14):1639-1662 (1998).

Rarey et al., "A Fast Flexible Docking Method Using an Incremental Construction Algorithm," *J. Mol. Biol.*, 261:470-489 (1996).

Rarey et al., "Placement of medium-sized molecular fragments into active sites of proteins," *J. Computer-Aided Molecular Design*, 10:41-54 (1996).

Ritchie et al., "Protein Docking Using Spherical Polar Fourier Correlations," *Proteins: Structure, Function, and Genetics*, 39:178-194 (2000).

Ritchie et al., "Fast Computation, Rotation, and Comparison of Low Resolution Spherical Harmonic Molecular Surfaces," *J. Computational Chemistry*, 20(4):383-395 (1999).

Shoichet et al., "Molecular Docking Using Shape Descriptors," *J. Comp. Chem.*, 13(3):380-397 (1992).

* cited by examiner

0240

```
HEADER  OXIDO-REDUCTASE              25-JUN-82  4DFR
COMPND  DIHYDROFOLATE REDUCTASE (E.C.1.5.1.3) COMPLEX WITH
COMPND  2 METHOTREXATE
SOURCE  (ESCHERICHIA $COLI B), STRAIN /MB1428$,
SOURCE  2 A METHOTREXATE-RESISTANT MUTANT
AUTHOR  D.J.FILMAN,D.A.MATTHEWS,J.T.BOLIN,J.KRAUT
JRNL        AUTH  J.T.BOLIN,D.J.FILMAN,D.A.MATTHEWS,R.C.HAMLIN,
JRNL        AUTH 2 J.KRAUT
JRNL        REF   J.BIOL.CHEM.         V. 257 13650 1982
REMARK  1 RESOLUTION. 1.7
ANGSTROMS.
FORMUL  2 MTX   2(C20 H22 N8 O5)
HETATM   1 N1  MTX A   1      22.983  58.667  24.488  1.00 15.10
HETATM   2 C2  MTX A   1      23.468  58.215  23.282  1.00 17.30
HETATM   3 NA2 MTX A   1      24.797  58.223  23.208  1.00 16.50
HETATM   4 N3  MTX A   1      22.792  57.819  22.230  1.00 17.90
HETATM   5 C4  MTX A   1      21.459  57.803  22.068  1.00 18.60
HETATM   6 NA4 MTX A   1      20.821  57.440  21.075  1.00 18.10
HETATM   7 C4A MTX A   1      20.900  58.304  23.363  1.00 18.90
HETATM   8 N5  MTX A   1      19.558  58.514  23.370  1.00 19.80
HETATM   9 C6  MTX A   1      18.989  58.982  24.422  1.00 18.60
HETATM  10 C7  MTX A   1      19.781  59.256  25.628  1.00 18.80
HETATM  11 N8  MTX A   1      21.096  59.176  25.562  1.00 21.90
HETATM  12 C8A MTX A   1      21.608  58.594  24.363  1.00 19.50
HETATM  13 C9  MTX A   1      17.465  59.006  24.451  1.00 20.50
HETATM  14 N10 MTX A   1      16.957  59.967  25.533  1.00 17.40
HETATM  15 CM  MTX A   1      16.225  59.184  26.643  1.00 22.30
HETATM  16 C11 MTX A   1      18.122  64.100  25.805  1.00 22.10
HETATM  17 C12 MTX A   1      17.288  63.511  26.732  1.00 18.80
HETATM  18 C13 MTX A   1      16.845  62.195  26.688  1.00 18.10
HETATM  19 C14 MTX A   1      17.320  61.452  25.680  1.00 19.70
HETATM  20 C15 MTX A   1      18.141  62.098  24.672  1.00 17.60
HETATM  21 C16 MTX A   1      18.518  63.414  24.738  1.00 17.00
HETATM  22 C   MTX A   1      18.192  65.626  25.834  1.00 23.30
HETATM  23 O   MTX A   1      17.516  66.280  26.783  1.00 25.90
HETATM  24 N   MTX A   1      19.329  65.981  25.135  1.00 21.30
HETATM  25 CA  MTX A   1      19.837  67.459  25.135  1.00 22.60
HETATM  26 CT  MTX A   1      20.159  67.548  23.635  1.00 22.80
HETATM  27 O1  MTX A   1      20.289  66.659  22.848  1.00 21.30
HETATM  28 O2  MTX A   1      19.921  68.750  23.149  1.00 27.20
HETATM  29 CB  MTX A   1      21.217  67.669  25.761  1.00 27.40
HETATM  30 CG  MTX A   1      20.891  67.636  27.320  1.00 36.20
```

0250

0260

```
HETATM  31 CD  MTX A   1      19.921  68.524  28.357  1.00 41.50
HETATM  32 OE1 MTX A   1      19.413  68.371  29.593  1.00 49.10
HETATM  33 OE2 MTX A   1      19.441  69.469  27.489  1.00 42.50
CONECT   1   2  12
CONECT   2   1   3   4
CONECT   3   2
CONECT   4   2   5
CONECT   5   4   6   7
CONECT   6   5
CONECT   7   5   8  12
CONECT   8   7   9
CONECT   9   8  10  13
CONECT  10   9  11
CONECT  11  10  12
CONECT  12   1   7  11
CONECT  13   9  14
CONECT  14  13  15  19
CONECT  15  14
CONECT  16  17  21  22
CONECT  17  16  18
CONECT  18  17  19
CONECT  19  14  18  20
CONECT  20  19  21
CONECT  21  16  20
CONECT  22  16  23  24
CONECT  23  22
CONECT  24  22  25
CONECT  25  24  26  29
CONECT  26  25  27  28
CONECT  27  26
CONECT  28  26
CONECT  29  25  30
CONECT  30  29  31
CONECT  31  30  32  33
CONECT  32  31
CONECT  33  31
END
```

METHOD AND APPARATUS FOR ANALYSIS OF MOLECULAR COMBINATION BASED ON COMPUTATIONS OF SHAPE COMPLEMENTARITY USING BASIS EXPANSIONS

CROSS-REFERENCES TO RELATED APPLICATIONS

The present application claims priority from and is a non-provisional application of U.S. Provisional Application No. 60/511,477, entitled "Method and Apparatus for Assessing a Likelihood of Combination of Molecules Using a Basis Expansion" filed Oct. 14, 2003, the entire contents of which are herein incorporated by reference for all purposes.

FIELD OF THE INVENTION

The present invention generally relates to bioinformatics, proteomics, molecular modeling, computer-aided molecular design (CAMD), and more specifically computer-aided drug design (CADD) and computational modeling of molecular combinations.

BACKGROUND OF THE INVENTION

An explanation of conventional drug discovery processes and their limitations is useful for understanding the present invention.

Discovering a new drug to treat or cure some biological condition, is a lengthy and expensive process, typically taking on average 12 years and $800 million per drug, and taking possibly up to 15 years or more and $1 billion to complete in some cases.

A goal of a drug discovery process is to identify and characterize a chemical compound or ligand biomolecule, that affects the function of one or more other biomolecules (i.e., a drug "target") in an organism, usually a biopolymer, via a potential molecular interaction or combination. Herein the term biopolymer refers to a macromolecule that comprises one or more of a protein, nucleic acid (DNA or RNA), peptide or nucleotide sequence or any portions or fragments thereof. Herein the term biomolecule refers to a chemical entity that comprises one or more of a biopolymer, carbohydrate, hormone, or other molecule or chemical compound, either inorganic or organic, including, but not limited to, synthetic, medicinal, drug-like, or natural compounds, or any portions or fragments thereof.

The target molecule is typically a disease-related target protein or nucleic acid for which it is desired to affect a change in function, structure, and/or chemical activity in order to aid in the treatment of a patient disease or other disorder. In other cases, the target is a biomolecule found in a disease-causing organism, such as a virus, bacteria, or parasite, that when affected by the drug will affect the survival or activity of the infectious organism. In yet other cases, the target is a biomolecule of a defective or harmful cell such as a cancer cell. In yet other cases the target is an antigen or other environmental chemical agent that may induce an allergic reaction or other undesired immunological or biological response.

The ligand is typically a small molecule drug or chemical compound with desired drug-like properties in terms of potency, low toxicity, membrane permeability, solubility, chemical/metabolic stability, etc. In other cases, the ligand may be biologic such as an injected protein-based or peptide-based drug or even another full-fledged protein. In yet other cases the ligand may be a chemical substrate of a target enzyme. The ligand may even be covalently bound to the target or may in fact be a portion of the protein, e.g., protein secondary structure component, protein domain containing or near an active site, protein subunit of an appropriate protein quaternary structure, etc.

Throughout the remainder of the background discussion, unless otherwise specifically differentiated, a (potential) molecular combination will feature one ligand and one target, the ligand and target will be separate chemical entities, and the ligand will be assumed to be a chemical compound while the target will be a biological protein (mutant or wild type). Note that the frequency of nucleic acids (both DNA/RNA) as targets will likely increase in coming years as advances in gene therapy and pathogenic microbiology progress. Also the term "molecular complex" will refer to the bound state between the target and ligand when interacting with one another in the midst of a suitable (often aqueous) environment. A "potential" molecular complex refers to a bound state that may occur albeit with low probability and therefore may or may not actually form under normal conditions.

The drug discovery process itself typically includes four different subprocesses: (1) target validation; (2) lead generation/optimization; (3) preclinical testing; and (4) clinical trials and approval.

Target validation includes determination of one or more targets that have disease relevance and usually takes two-and-a-half years to complete. Results of the target validation phase might include a determination that the presence or action of the target molecule in an organism causes or influences some effect that initiates, exacerbates, or contributes to a disease for which a cure or treatment is sought. In some cases a natural binder or substrate for the target may also be determined via experimental methods.

Lead generation typically involves the identification of lead compounds that can bind to the target molecule and thereby alter the effects of the target through either activation, deactivation, catalysis, or inhibition of the function of the target, in which case the lead would be a viewed as a suitable candidate ligand to be used in the drug application process. Lead optimization involves the chemical and structural refinement of lead candidates into drug precursors in order to improve binding affinity to the desired target, increase selectivity, and also to address basic issues of toxicity, solubility, and metabolism. Together lead generation and lead optimization typically takes about three years to complete and might result in one or more chemically distinct leads for further consideration.

In preclinical testing, biochemical assays and animal models are used to test the selected leads for various pharmacokinetic factors related to drug absorption, distribution, metabolism, excretion, toxicity, side effects, and required dosages. This preclinical testing takes approximately one year. After the preclinical testing period, clinical trials and approval take another six to eight or more years during which the drug candidates are tested on human subjects for safety and efficacy.

Rational drug design generally uses structural information about drug targets (structure-based) and/or their natural ligands (ligand-based) as a basis for the design of effective lead candidate generation and optimization. Structure-based rational drug design generally utilizes a three-dimensional model of the structure for the target. For target proteins or nucleic acids such structures may be as the result of X-ray crystallography/NMR or other measurement procedures or may result from homology modeling, analysis of protein motifs and conserved domains, and/or computational modeling of protein folding or the nucleic acid equivalent. Model-built structures are often all that is available when considering many membrane-associated target proteins, e.g., GPCRs and ion-channels. The structure of a ligand may be generated in a similar manner or may instead be constructed ab initio from a known 2-D chemical representation using fundamental physics and chemistry principles, provided the ligand is not a biopolymer.

Rational drug design may incorporate the use of any of a number of computational components ranging from computational modeling of target-ligand molecular interactions and combinations to lead optimization to computational prediction of desired drug-like biological properties. The use of computational modeling in the context of rational drug design has been largely motivated by a desire to both reduce the required time and to improve the focus and efficiency of drug research and development, by avoiding often time consuming and costly efforts in biological "wet" lab testing and the like.

Computational modeling of target-ligand molecular combinations in the context of lead generation may involve the large-scale in-silico screening of compound libraries (i.e., library screening), whether the libraries are virtually generated and stored as one or more compound structural databases or constructed via combinatorial chemistry and organic synthesis, using computational methods to rank a selected subset of ligands based on computational prediction of bioactivity (or an equivalent measure) with respect to the intended target molecule.

Throughout the text, the term "binding mode" refers to the 3-D molecular structure of a potential molecular complex in a bound state at or near a minimum of the binding energy (i.e., maximum of the binding affinity), where the term "binding energy" (sometimes interchanged with "binding affinity" or "binding free energy") refers to the change in free energy of a molecular system upon formation of a potential molecular complex, i.e., the transition from an unbound to a (potential) bound state for the ligand and target. Here the term free energy generally refers to both enthalpic and entropic effects as the result of physical interactions between the constituent atoms and bonds of the molecules between themselves (i.e., both intermolecular and intramolecular interactions) and with their surrounding environment. Examples of the free energy are the Gibbs free energy encountered in the canonical or grand canonical ensembles of equilibrium statistical mechanics.

In general, the optimal binding free energy of a given target-ligand pair directly correlates to the likelihood of formation of a potential molecular complex between the two molecules in chemical equilibrium, though, in truth, the binding free energy describes an ensemble of (putative) complexed structures and not one single binding mode. However, in computational modeling it is usually assumed that the change in free energy is dominated by a single structure corresponding to a minimal energy. This is certainly true for tight binders (pK~0.1 to 10 nanomolar) but questionable for weak ones (pK~10 to 100 micromolar). The dominating structure is usually taken to be the binding mode. In some cases it may be necessary to consider more than one alternative-binding mode when the associated system states are nearly degenerate in terms of energy.

It is desirable in the drug discovery process to identify quickly and efficiently the optimal docking configurations, i.e., binding modes, of two molecules or parts of molecules. Efficiency is especially relevant in the lead generation and lead optimization stages for a drug discovery pipeline, where it is desirable to accurately predict the binding mode for possibly millions of potential molecular complexes, before submitting promising candidates to further analysis.

Binding modes and binding affinity are of direct interest to drug discovery and rational drug design because they often help indicate how well a potential drug candidate may serve its purpose. Furthermore, where the binding mode is determinable, the action of the drug on the target can be better understood. Such understanding may be useful when, for example, it is desirable to further modify one or more characteristics of the ligand so as to improve its potency (with respect to the target), binding specificity (with respect to other targets), or other chemical and metabolic properties.

A number of laboratory methods exist for measuring or estimating affinity between a target molecule and a ligand. Often the target might be first isolated and then mixed with the ligand in vitro and the molecular interaction assessed experimentally such as in the myriad biochemical and functional assays associated with high throughput screening. However, such methods are most useful where the target is simple to isolate, the ligand is simple to manufacture and the molecular interaction easily measured, but is more problematic when the target cannot be easily isolated, isolation interferes with the biological process or disease pathway, the ligand is difficult to synthesize in sufficient quantity, or where the particular target or ligand is not well characterized ahead of time. In the latter case, many thousands or millions of experiments might be needed for all possible combinations of the target and ligands, making the use of laboratory methods unfeasible.

While a number of attempts have been made to resolve this bottleneck by first using specialized knowledge of various chemical and biological properties of the target (or even related targets such as protein family members) and/or one or more already known natural binders or substrates to the target, to reduce the number of combinations required for lab processing, this is still impractical and too expensive in most cases. Instead of actually combining molecules in a laboratory setting and measuring experimental results, another approach is to use computers to simulate or characterize molecular interactions between two or more molecules (i.e., molecular combinations modeled in silico). The use of computational methods to assess molecular combinations and interactions is usually associated with one or more stages of rational drug design, whether structure-based, ligand-based, or both.

The computational prediction of one or more binding modes and/or the computational assessment of the nature of a molecular combination and the likelihood of formation of a potential molecular complex is generally associated with the term "docking" in the art. To date, conventional "docking" methods have included a wide variety of computational techniques as described in the forthcoming section entitled "REFERENCES & PRIOR ART".

Whatever the choice of computational docking method there are inherent trade-offs between the computational complexity of both the underlying molecular models and the intrinsic numerical algorithms, and the amount of computing resources (time, number of CPUs, number of simulations) that must be allocated to process each molecular combination. For example, while highly sophisticated molecular dynamics simulations (MD) of the two molecules surrounded by explicit water molecules and evolved over trillions of time steps may lead to higher accuracy in modeling the potential molecular combination, the resultant computational cost (i.e., time and computing power) is so enormous that such simulations are intractable for use with more than just a few molecular combinations.

One major distinction amongst docking methods as applied to computational modeling of molecular combinations is whether the ligand and target structures remain rigid throughout the course of the simulation (i.e., rigid-body docking) vs. the ligand and/or target being allowed to change their molecular conformations (i.e., flexible docking). In general, the latter scenario involves more computational complexity, though flexible docking may often achieve higher accuracy than rigid-body docking when modeling various molecular combinations.

That being said rigid-body docking can provide valuable insight into the nature of a molecular combination and/or the likelihood of formation of a potential molecular complex and has many potential uses within the context of rational drug discovery. For instance rigid-body docking may be appropriate for docking small, rigid molecules (or molecular fragments) to a simple protein with a well-defined, nearly rigid active site. As another example, rigid-body docking may also be used to more efficiently and rapidly screen out a subset of likely nonactive ligands in a molecule library for a given target, and then applying more onerous flexible docking procedures to the surviving candidate molecules. Rigid-body docking may also be suitable for de novo ligand design and combinatorial library design.

Moreover, in order to better predict the binding mode and better assess the nature and/or likelihood of a molecular combination when one or both molecules are likely to be flexible, rigid-body docking can be used in conjunction with a process for generating likely yet distinct molecular conformers of one or both molecules for straightforward and efficient virtual screening of a molecule library against a target molecule. However, as will be discussed, even rigid body docking of molecular combinations can be computationally expensive and thus there is a clear need for better and more efficient computational methods based on rigid body docking when assessing the nature and/or likelihood of molecular combinations.

As outlined in the section entitled "REFERENCES & PRIOR ART", conventional computational methods for predicting binding modes and assessing the nature and/or likelihood of molecular combinations in the context of rigid-body docking include a wide variety of techniques. These include methods based on pattern matching (often graph-based), maximization of shape complementarity (i.e., shape correlations), geometric hashing, pose clustering, and even the use of one or more flexible docking methods with the simplifying run-time condition that both molecules are rigid.

Of special interest to this invention is class of rigid-body docking techniques based on the maximization of shape complementarity via evaluation of the spatial correlation between two representative molecular surfaces at different relative positions and orientations. One example is the "Hex" docking software described in Ritchie, D. W. and Kemp. G. J. L, "Protein Docking Using Spherical Polar Fourier Correlations", (2000), *Proteins: Structure, Function, and Genetics*, 39, 178-194; (hereinafter, "Ritchie et al"), all of which is hereby incorporated by reference in their entirety.

Further examples include the "FTDOCK" docking software of the *Cambridge Crystallographic Data Center* described in Aloy, P., Moont, G., Gabb, H. A., Querol, E., Aviles, F. X., and Sternberg, M. J. E., "Modeling Protein Docking using Shape Complementarity, Electrostatics and Biochemical Information," (1998), *Proteins: Structure, Function, and Genetics*, 33(4) 535-549; all of which is hereby incorporated by reference in their entirety.

Such shape complementarity based methods while typically treating molecules as rigid and thus perhaps less rigorous than their flexible docking counterparts, especially in the context of flexible molecules, is still potentially valuable for the fast, efficient screening of two molecules in order to make a preliminary assessment of the nature and/or likelihood of formation of a potential molecular complex of the two molecules or to make an initial prediction of the preferred binding mode for the molecular combination. Such a preliminary assessment may significantly reduce the number of candidates that must be further screened in silico by another more computationally costly docking method. Moreover, the utility of computing shape complementarity has been demonstrated with respect to multiple protein-protein systems, including both enzyme-inhibitor and antibody-antigen, as per FTDOCK and Ritchie et al.

Previous formulations for the computation of shape complementarity generally fall into four categories.

The first category involves the calculation of a spatial correlation in the spatial domain between two volumetric functions describing a representative molecular surface for each molecule, where the spatial correlation between two 3-D complex functions, $f(\vec{r})$ and $g(\vec{r})$, is calculated as follows:

$$f * g = \int_{\vec{r}} \overline{f}(\vec{r}) g(\vec{r} + \vec{x}) d\vec{r} \qquad \text{[Eqn. 1]}$$

where $\overline{f}$ denotes the complex conjugate and * denotes convolution. In the spatial domain, the spatial correlation is performed by converting the integrals into summations and directly computing over a sampling space comprising three translation variables with a specified sampling resolution. A search is then conducted by reevaluating the spatial correlation for each new and different relative orientation of the molecules. Those configurations that show the highest net spatial correlation are typically selected as possible candidate binding modes.

However, the method of directly computing the spatial correlation in the spatial domain is often very computationally intensive, since if the sampling translation grid is a M×M×M grid, the above spatial correlation calculation requires $O(M^6)$ operations. For instance, when M=256, there are more than $2.8 \times 10^{14}$ multiplication operations required. Furthermore, the $O(M^6)$ calculations must be performed for every relative orientation of the two molecules, making the total number of calculations impractical at best.

The second category involves the calculation of a spatial correlation in the frequency domain between two volumetric functions describing a representative molecular surface for each molecule, where the spatial correlation between two 3-D functions, f and g, is still defined as before, but a frequency space decomposition, such as a Fourier transform, is used in order to reduce the number of calculations. For a full description of the Fourier transform refer to Press, W. H., Flannery, B. P., Teukolsky, S. A., and Vetterling, W. T., "Numerical Recipes in C: The Art of Scientific Computing", Cambridge University Press (1993) (hereinafter, "Press et al"), hereby incorporated by reference in its entirety.

To compute a 3-D spatial correlation in Fourier space, one can use the following relation, also known as the Correlation Theorem (Press et al). The convolution of two complex 3-D functions $f(\vec{r})$ with $g(\vec{r})$ is given by:

$$f * g = F^{-1}(\overline{F}(\upsilon) G(\upsilon)) \qquad \text{[Eqn. 2]}$$

where $F^{-1}$ refers to the inverse Discrete Fourier Transform (Press et al), $\overline{F}(\upsilon)$ is Discrete Fourier Transform of the complex conjugate of f($\vec{r}$) and G($\upsilon$) is the Discrete Fourier Transform of g($\vec{r}$). Similar formulae can be generated for other frequency decompositions besides Fourier, such as a Laplace transform, a Discrete Cosine transform, and others, as described in Arfken, G. B., and Weber H. J., "Mathematical Method for Physicist", Harcourt/Academic Press (2000), (hereinafter, "Arfken et al"), hereby incorporated by reference in its entirety.

For the same M×M×M grid, the frequency based evaluation of the spatial correlation will require approximately $O(3M^3 \ln(M))$ operations where $\ln(M)$ denotes the natural logarithm of M. While the number of operations decreases substantially when the DFTs are used as opposed to direct computation in the spatial domain, the amount of memory storage and/or the amount of data that must be read from storage must still be taken into account, i.e., the input/output (I/O) bandwidth requirement.

For example, for M=256 at 16 bit precision, 800 Mbits are required for computing the 3-D spatial correlation using DFTs for just one relative orientation. Generally, this is a very large amount of data for storage directly in memory and would require millions of clock cycles to fetch from one or more DRAM chips with current DRAM and I/O bus technology. Moreover, the $O(3M^3 \ln(M))$ calculations and the access of hundreds of millions of data bits must be performed for every relative orientation of the two molecules, making the entire process onerous when considering possibly millions of such relative orientations in the course of a high resolution search of the shape complementarity space. For this reason, Fourier based methods for evaluating shape complementarity often take hours on conventional computer software in order to complete for large protein systems, for instance, as in FTDOCK, and as such are not suitable for large-scale screening.

The third category involves the least-square minimization (or equivalent minimization) of separation distances between critical surface and/or fitting points that represent the molecular surfaces of the two molecules. Examples include the Patchdock docking software written by Nussinov-Wolfson Structural Bioinformatics Group at Tel-Aviv University, based on principles described in Lin, S. L., Nussinov, R., Fischer, D., and Wolfson, H. J., "Molecular surface representations by sparse critical points", (1994) *Proteins: Structure, Function, and Genetics*, 18, 94-101; all of which are hereby incorporated by reference in their entirety.

Such methods often suffer from degraded accuracy, especially when the molecular surface geometry is complex or when the ligand molecule is very small relative to the protein receptor and/or characterized by poor binding affinities. Moreover, the cost of computing the surface critical points is often itself very expensive.

The number of computations associated with the three method categories described above renders the process impractical for use with conventional computer software and hardware configurations when performing large-scale screening. Moreover, the above methods are not practical for high accuracy prediction of the binding mode due to the requirement of a high resolution of the associated sampling space.

A fourth category has been developed for the efficient estimation of shape complementarity based on the decomposition of two volumetric functions describing a representative molecular surface for each molecule onto an appropriate orthogonal basis set, such as a radial-spherical harmonics expansion, as described in Ritchie et al. The chief advantage of this type of method is that the required number of calculations scale linearly with the desired number of sampled configurations, thus allowing for a dense sampling of the geometric shape complementarity. Moreover, the computing time is roughly invariant with respect to the sizes of the two molecules and is thus suitable for protein-protein docking. However, to achieve high accuracy for complex molecular surface geometries, it is necessary to perform the orthogonal basis expansion with a large expansion order and as such the total computing time can be quite large. Furthermore, current methods such as those outlined in Ritchie et al are not amenable to implementation in customized or other application specific hardware for use in large-scale screening.

In summary, it is desirable in the drug discovery process to identify quickly and efficiently the optimal configurations, i.e., binding modes, of two molecules or parts of molecules. Efficiency is especially relevant in the lead generation and lead optimization stages for a drug discovery pipeline, where it may be desirable to accurately predict the binding mode and binding affinity for possibly millions of potential target-ligand molecular combinations, before submitting promising candidates to further analysis. There is a clear need then to have more efficient systems and methods for computational modeling of the molecular combinations with reasonable accuracy.

In general, the present invention relates to an efficient computational method for analysis of molecular combinations based on maximization of shape complementarity over a set of configurations of a molecular combination through computation of a basis expansion representing molecular shapes in a coordinate system. Here the analysis of the molecular combination may involve the prediction of likelihood of formation of a potential molecular complex, the prediction of the binding mode (or even additional alternative modes) for the combination, the characterization of the nature of the interaction or binding of various components of the molecular combination, or even an approximation of binding affinity for the molecular combination based on a shape complementarity score or an equivalent measure. The invention also addresses and solves the various hardware implementation hurdles and bottlenecks associated with current conventional methods.

REFERENCES & PRIOR ART

Prior art in the field of the current invention is heavily documented: the following tries to summarize it.

Drews [1] provides a good overview of the current state of drug discovery. In [2] Abagyan and Totrov show the state of high throughput docking and scoring and its applications. Lamb et al [3] further teach a general approach to the design, docking, and virtual screening of multiple combinatorial libraries against a family of proteins, finally Waskowycz et al [4] describe the use of multiple computers to accelerate virtual screening of a large ligand library against a specific target by assigning groups of ligands to specific computers.

[1] J. Drews, "Drug Discovery: A Historical perspective," Science 287, 1960-1964 (2000).

[2] Ruben Abagyan and Maxim Totrov, "High-throughput docking for lead generation". Current Opinion in Chemical Biology 2001, 5:375-382.

[3] Lamb, M. L.; Burdick, K. W.; Toba, S.; Young, M. M.; Skillman, A. G. et al "Design, docking, and evaluation of multiple libraries against multiple targets". Proteins 2001, 42, 296-318.

[4] Waszkowycz, B., Perkins, T. D. J., Sykes, R. A., Li, J. "Large-scale virtual screening for discovering leads in the post-genomic era", IBM Systems Journal, Vol. 40, No. 2 (2001).

There are a number of examples of software tools currently used to perform docking simulations. These methods involve a wide range of computational techniques, including use of a) rigid-body pattern-matching algorithms, either based on surface correlations, use of geometric hashing, pose clustering, or graph pattern-matching; b) fragmental-based methods, including incremental construction or "place and join" operators; c) stochastic optimization methods including use of Monte Carlo, simulated annealing, or genetic (or memetic) algorithms; d) molecular dynamics simulations; or e) hybrids strategies derived thereof.

The earliest docking software tool was a graph-based rigid-body pattern-matching algorithm called DOCK [5, 6, 7], developed at UCSF back in 1982 (v1.0) and now up to v5.0 (with extensions to include incremental construction). Other examples of graph-based pattern-matching algorithms include CLIX [8] (which in turn uses GRID [9]), FLOG [10] and LIGIN [11].

[5] Shoichet, B. K., Bodian, D. L. and Kuntz, I. D., "Molecular docking using shape descriptors", *J. Comp. Chem.*, Vol. 13 No. 3, 380-397 (1992).

[6] Meng, E. C., Gschwend, D. A., Blaney, J. M., and I. D. Kuntz, "Orientational sampling and rigid-body minimization in molecular docking", Proteins: Structure, Function, and Genetics, Vol. 17, 266-278 (1993).

[7] Ewing, T. J. A. and Kuntz, I. D., "Critical Evaluation of Search Algorithms for Automated Molecular Docking and Database Screening", *J. Computational Chemistry*, Vol. 18 No. 9, 1175-1189 (1997).

[8] Lawrence, M. C. and Davis, P. C.; "CLIX: A Search Algorithm for Finding Novel Ligands Capable of Binding Proteins of Known Three-Dimensional Structure", *Proteins*, Vol. 12, 31-41 (1992).

[9] Kastenholz, M. A., Pastor, M., Cruciani, G., Haaksma, E. E. J., Fox, T., "GRID/CPCA: A new computational tool to design selective ligands", *J. Medicinal Chemistry*, Vol. 43, 3033-3044 (2000).

[10] Miller, M. D., Kearsley, S. K., Underwood, D. J. and Sheridan, R. P., "FLOG: a system to select 'qasi-flexible' ligands complementary to a receptor of known three-dimensional structure", *J. Computer-Aided Molecular Design*, Vol. 8 No. 2, 153-174 (1994).

[11] Sobolev, V., Wade, R. C., Vriend, G. and Edelman, M., "Molecular docking using surface complementarity", *Proteins*, Vol. 25, 120-129 (1996).

Other rigid-body pattern-matching docking software tools include the shape-based correlation methods of FTDOCK [12] and HEX [13], the geometric hashing of Fischer et al [14], or the pose clustering of Rarey et al [15].

[12] Katchalski-Katzir, E., Shariv, I., Eisenstein, M., Friesem, A. A., Aflalo, C., and Vakser, I. A., "Molecular surface recognition: Determination of geometric fit between proteins and their ligands by correlation techniques", *Proceedings of the National Academy of Sciences of the United States of America*, Vol. 89 No. 6, 2195-2199 (1992).

[13] Ritchie, D. W. and Kemp. G. J. L., "Fast Computation, Rotation, and Comparison of Low Resolution Spherical Harmonic Molecular Surfaces", *J. Computational Chemistry*, Vol. 20 No. 4, 383-395 (1999).

[14] Fischer, D., Norel, R., Wolfson, H. and Nussinov, R., "Surface motifs by a computer vision technique: searches, detection, and implications for protein-ligand recognition", *Proteins*, Vol. 16, 278-292 (1993).

[15] Rarey, M., Wefing, S., and Lengauer, T., "Placement of medium-sized molecular fragments into active sites of proteins", *J. Computer-Aided Molecular Design*, Vol. 10, 41-54 (1996).

In general, rigid-body pattern-matching algorithms assume that both the target and ligand are rigid (i.e., not flexible) and hence may be appropriate for docking small, rigid molecules (or molecular fragments) to a simple protein with a well-defined, nearly rigid active site. Thus this class of docking tools may be suitable for de novo ligand design, combinatorial library design, or straightforward rigid-body screening of a molecule library containing multiple conformers per ligand.

Incremental construction based docking software tools include FlexX [16, 17] from Tripos (licensed from EMBL), Hammerhead [18], DOCK v4.0 [7] (as an option), and the nongreedy, backtracking algorithm of Leach et al [19]. Programs using incremental construction in the context of de novo ligand design include LUDI [20] (from Accelrys) and GrowMol [21]. Docking software tools based on 'place and join' strategies include DesJarlais et al [22].

[16] Kramer, B., Rarey, M. and Lengauer, T., "Evaluation of the FlexX incremental construction algorithm for protein-ligand docking", *Proteins*, Vol. 37, 228-241 (1999).

[17] Rarey, M., Kramer, B., Lengauer, T., and Klebe, G., "A Fast Flexible Docking Method Using An Incremental Construction Algorithm", *J. Mol. Biol.*, Vol. 261, 470-489 (1996).

[18] Welch, W., Ruppert, J. and Jain, A. N., "Hammerhead: Fast, fully automated docking of flexible ligands to protein binding sites", *Chemical Biology*, Vol. 3, 449-462 (1996).

[19] Leach, A. R., Kuntz, I. D., "Conformational Analysis of Flexible Ligands in Macromolecular Receptor Sites", *J. Comp. Chem.*, Vol. 13, 730-748 (1992).

[20] Bohm, H. J., "The computer program LUDI: a new method for the de novo design of enzyme inhibitors", *J. Computer-Aided Molecular Design*, Vol. 6, 61-78 (1992).

[21] Bohacek, R. S. and McMartin, C., "Multiple Highly Diverse Structures Complementary to Enzyme Binding Sites: Results of Extensive Application of a de Novo Design Method Incorporating Combinatorial Growth", *J. American Chemical Society*, Vol. 116, 5560-5571 (1994).

[22] DesJarlais, R. L., Sheridan, R. P., Dixon, J. S., Kuntz, I. D., and Venkataraghavan, R., "Docking Flexible Ligands to Macromolecular Receptors by Molecular Shape", *J. Med. Chem.*, Vol. 29, 2149-2153 (1986).

Incremental construction algorithms may be used to model docking of flexible ligands to a rigid target molecule with a well-characterized active site. They may be used when screening a library of flexible ligands against one or more targets. They are often comparatively less compute-intensive, yet consequently less accurate, than many of their stochastic optimization based competitors. However, even FlexX may take on order of <1-2 minutes to process one target-ligand combination and thus may still be computationally onerous depending on the size of the library (e.g., tens of millions or more compounds). Recently FlexX was extended to FlexE [23] to attempt to account for partial flexibility of the target molecule's active site via use of user-defined ensembles of certain active site rotamers.

[23] Claussen, H., Buning, C., Rarey, M., and Lengauer, T., "FlexE: Efficient Molecular Docking Considering Protein Structure Variations", *J. Molecular Biology*, Vol. 308, 377-395 (2001).

Computational docking software tools based on stochastic optimization include ICM [24] (from MolSoft), GLIDE [25] (from Schrodinger), and LigandFit [26] (from Accelrys), all based on modified Monte Carlo techniques, and AutoDock v.2.5 [27] (from Scripps Institute) based on simulated annealing. Others based on genetic or memetic algorithms include GOLD [28, 29], DARWIN [30], and AutoDock v.3.0 [31] (also from Scripps).

[24] Abagyan, R. A., Totrov, M. M., and Kuznetsov, D. N., "Biased probability Monte Carlo conformational searches and electrostatic calculations for peptides and proteins", *J. Comp. Chem.*, Vol. 15, 488-506 (1994).

[25] Halgren, T. A., Murphy, R. B., Friesner, R. A., Beard, H. S., Frye, L. L., Pollard, W. T., and Banks, J. L., "Glide: a new approach for rapid, accurate docking and scoring. 2. Enrichment factors in database screening", *J Med Chem.*, Vol. 47 No. 7, 1750-1759, (2004).

[26] Luty, B. A., Wasserman, Z. R., Stouten, P. F. W., Hodge, C. N., Zacharias, M., and McCammon, J. A., "Molecular Mechanics/Grid Method for the Evaluation of Ligand-Receptor Interactions", *J. Comp. Chem.*, Vol. 16, 454-464 (1995).

[27] Goodsell, D. S. and Olson, A. J., "Automated Docking of Substrates to Proteins by Simulated Annealing", *Proteins: Structure, Function, and Genetics*, Vol. 8, 195-202 (1990).

[28] Jones, G., Willett, P. and Glen, R. C., "Molecular Recognition of Receptor Sites using a Genetic Algorithm with a Description of Desolvation", *J. Mol. Biol.*, Vol. 245, 43-53 (1995).

[29] Jones, G., Willett, P., Glen, R. C., Leach, A., and Taylor, R., "Development and Validation of a Genetic Algorithm for Flexible Docking", *J. Mol. Biol.*, Vol. 267, 727-748 (1997).

[30] Taylor, J. S. and Burnett, R. M., *Proteins*, Vol. 41, 173-191 (2000).

[31] Morris, G. M., Goodsell, D. S., Halliday, R. S., Huey, R., Hart, W. E., Belew, R. K. and Olson, A. J., "Automated Docking Using a Lamarckian Genetic Algorithm and an Empirical Binding Free Energy Function", *J. Comp. Chem.*, Vol. 19, 1639-1662 (1998).

Stochastic optimization-based methods may be used to model docking of flexible ligands to a target molecule. They generally use a molecular-mechanics based formulation of the affinity function and employ various strategies to search for one or more favorable system energy minima. They are often more compute-intensive, yet also more robust, than their incremental construction competitors. As they are stochastic in nature, different runs or simulations may often result in different predictions. Traditionally most docking software tools using stochastic optimization assume the target to be nearly rigid (i.e., hydrogen bond donor and acceptor groups in the active site may rotate), since otherwise the combinatorial complexity increases rapidly making the problem difficult to robustly solve in reasonable time.

Molecular dynamics simulations have also been used in the context of computational modeling of target-ligand combinations. This includes the implementations presented in Di Nola et al [32] and Luty et al [16] (along with Monte Carlo). In principle, molecular dynamics simulations may be able to model protein flexibility to an arbitrary degree. On the other hand, they may also require evaluation of many fine-grained, time steps and are thus often very time-consuming (one order of hours or even days per target-ligand combination). They also often require user-interaction for selection of valid trajectories. Use of molecular dynamics simulations in lead discovery is therefore more suited to local minimization of predicted complexes featuring a small number of promising lead candidates.

[32] Di Nola, A., Berendsen, H. J. C., and Roccatano, D., "Molecular Dynamics Simulation of the Docking of Substrates to Proteins", *Proteins*, Vol. 19, 174-182 (1994).

Hybrid methods may involve use of rigid-body pattern matching techniques for fast screening of selected low-energy ligand conformations, followed by Monte Carlo torsional optimization of surviving poses, and finally even molecular dynamics refinement of a few choice ligand structures in combination with a (potentially) flexible protein active site. An example of this type of docking software strategy is Wang et al [33].

[33] Wang, J., Kollman, P. A. and Kuntz, I. D., "Flexible ligand docking: A multi-step strategy approach", *Proteins*, Vol. 36, 1-19 (1999).

Force fields may be used to assign various atomic, bond, and/or other chemical or physical descriptors associated with components of molecules. In the context of the current invention this may include, but is not limited to, such items as vdW radii, charges (formal or partial), solvation dependent parameters, and equilibrium bond constants. An example cited in the technical description is the Tripos force field described in Clark et al. [34].

[34] Clark, M., Cramer, R. D., Opdenbosch, N. V., "Validation of the General Purpose Tripos 5.2 Force Field", *J. Comp. Chem.*, Vol. 10, 982-1012 (1989).

BRIEF SUMMARY OF THE INVENTION

Aspects of the present invention relate to a method and apparatus for the analysis of molecular combinations featuring two or more molecular subsets, wherein either one or both molecular subsets are from a plurality of molecular subsets selected from a molecule library, based on computations of shape complementarity utilizing a basis expansion representing molecular shapes of the first and second molecular subsets in a coordinate system. Sets of transformed expansion coefficients are calculated for a sequence of different configurations, i.e., relative positions and orientations, of the first molecular subset and the second molecular subset using coordinate transformations. In order to first obtain sets of translated expansion coefficients, the calculation includes application of a translation operator to a reference set of expansion coefficients before performing one or more rotation operations. The precomputed sets of translated expansion coefficients may be stored on a computer recordable medium, then later retrieved, and further subjected to one or more rotation operators in order to obtain sets of transformed expansion coefficients. Then a shape complementarity score, representing a correlation of the first and second molecular subsets, is computed over the sequence of different sampled configurations for the molecular combination, where each sampled configuration differs in both the relative positions and orientations of the first and second molecular subsets. The aspect of the invention involving application of the translation operator prior to one or more rotation operator(s) has significant and beneficial implications for hardware-based implementations of the method. Various embodiments of the invention relating to efficient implementation in the context of a hardware apparatus are also discussed.

BRIEF DESCRIPTION OF THE DRAWINGS

A more complex appreciation of the invention and many of the advantages thereof will be readily obtained as the same becomes better understood by references to the detailed description when considered in connection with the accompanying drawings, wherein:

FIGS. 2a, 2b, and 2c respectively show a 'ball and stick' representation of a input pose for a methotrexate molecule, a digital representation in the form of a pdb formatted file, and another digital representation in the form of a mol2 formatted file, both files containing structural and chemical information for the molecule depicted in FIG. 2a;

DETAILED DESCRIPTION OF THE INVENTION

Figure 1:
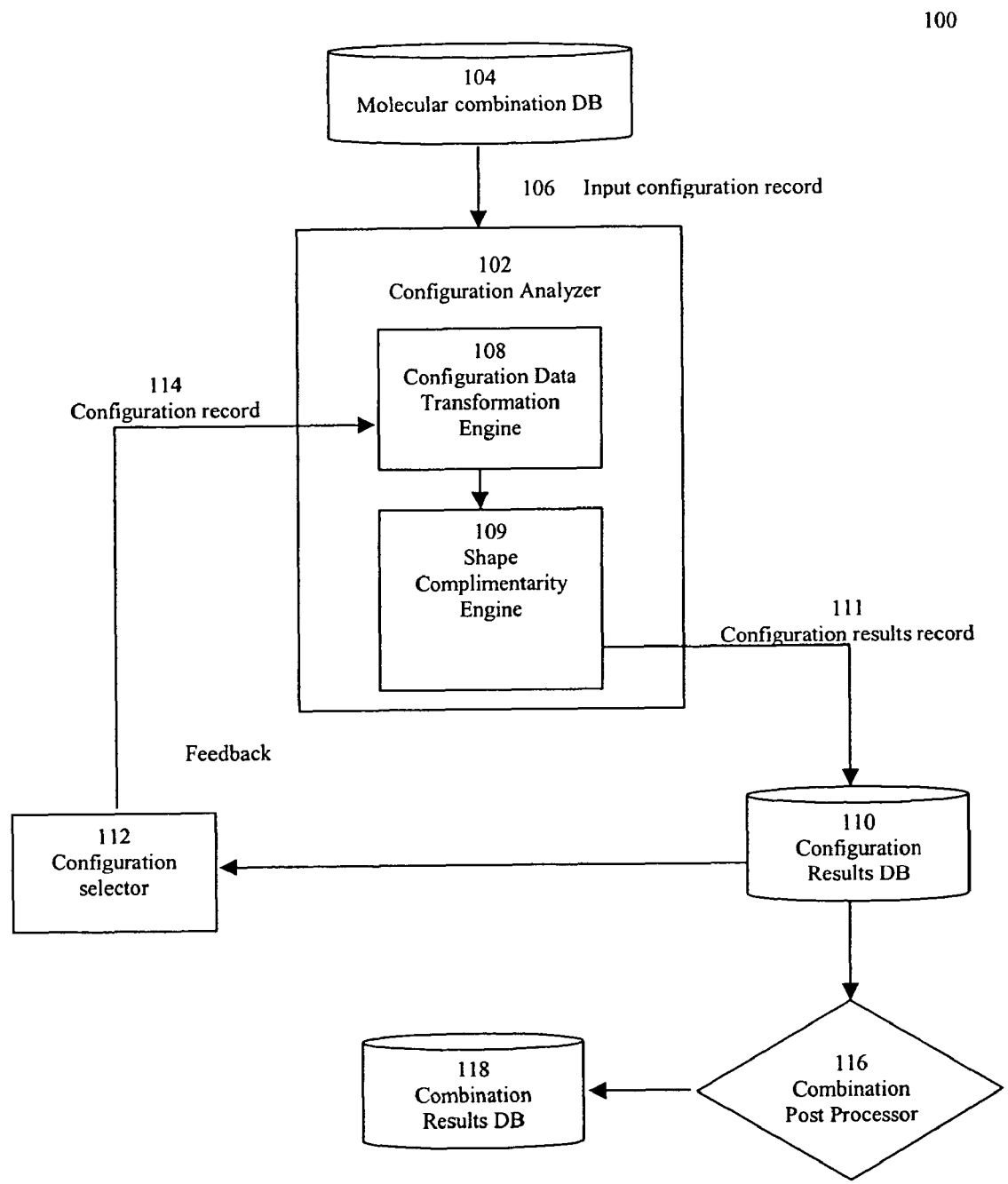
FIG. 1 is a block diagram view of an embodiment of a system that utilizes the present invention in accordance with analysis of a molecular combinations based on computations of shape complementarity over a set of sampled configurations.

The present invention has many applications, as will be apparent after reading this disclosure. In describing an embodiment of a computational system according to the present invention, only a few of the possible variations are described. Other applications and variations will be apparent to one of ordinary skill in the art, so the invention should not be construed as narrowly as the examples, but rather in accordance with the appended claims.

Embodiments of the invention will now be described, by way of example, not limitation. It is to be understood that the invention is of broad utility and may be used in many different contexts.

A molecular subset is a whole or parts of the components of a molecule, where the components can be single atoms or bonds, groups of atoms and/or bonds, amino acid residues, nucleotides, etc. A molecular subset might include a molecule, a part of a molecule, a chemical compound composed of one or more molecules (or other bio-reactive agents), a protein, one or more subsets or domains of a protein, a nucleic acid, one or more peptides, or one or more oligonucleotides. In another embodiment of the present invention, a molecular subset may also include one or more ions, individual atoms, or whole or parts of other simple molecules such as salts, gas molecules, water molecules, radicals, or even organic compounds like alcohols, esters, ketones, simple sugars, etc. In yet another embodiment, the molecular subset may also include organic molecules, residues, nucleotides, carbohydrates, inorganic molecules, and other chemically active items including synthetic, medicinal, drug-like, or natural compounds.

In yet another embodiment, the molecular subset may already be bound or attached to the target through one or more covalent bonds. In another embodiment the molecular subset may in fact include one or more structural components of the target, such as secondary structure elements that make-up a tertiary structure of a protein or subunits of a protein quaternary structure. In another embodiment the molecular subset may include one or more portions of a target molecule, such as protein domains that include the whole or part of an active site, one or more spatially connected subsets of the protein structure that are selected based on proximity to one or more protein residues, or even disconnected protein subsets that feature catalytic or other surface residues that are of interest for various molecular interactions. In another embodiment, the molecular subset may include the whole of or part of an existing molecular complex, meaning a molecular combination between two or more other molecular subset, as, for example, an activated protein or an allosterically bound protein.

A molecular combination (or combination) is a collection of two or more molecular subsets that may potentially bind, form a molecular complex, or otherwise interact with one another. A combination specifies at the very least the identities of the two or more interacting molecular subsets.

A molecular pose is the geometric state of a molecular subset described by its position and orientation within the context of a prescribed coordinate system. A molecular configuration (or configuration) of a molecular combination represents the joint poses of all constituent molecular subsets of a molecular combination. Different configurations are denoted by different relative positions and orientations of the molecular subsets with respect to one another. Linear coordinate transformations that do not change the relative position or orientation of constituent molecular subsets will not result in different configurations.

For the purposes of the invention different configurations of a molecular combination are obtained by the application of rigid body transformations, including relative translation and rotation, to one or more molecular subsets. For the purposes of the invention, such rigid body transformations are expected to preserve the conformational structure, as well as the stereochemistry and/or tautomerism (if applicable), of each molecular subset. In regards to the invention it is contemplated that when analyzing distinct conformations or stereoisomers of a molecular subset, each distinct conformation or stereoisomer will appear in a distinct molecular combination, each with its own attendant analysis. In this way, molecular combinations featuring flexible molecular subsets may be better analyzed using the invention based on consideration of multiple combinations comprising distinct conformations and/or stereoisomers.

In many of the forthcoming examples and explanations, the molecular combination will represent the typical scenario of two molecular subsets where a ligand biomolecule (first molecular subset) interacts with a target biomolecule (usually a biopolymer; second molecular subset). Thus in regards to the present invention, an of a molecular combination may seek to determine whether, in what fashion (i.e., binding mode), and/or to what degree, a ligand will interact with a target molecule based on computations of shape complementarity of one or more configurations. Here the term "shape complementarity" measures the geometric fit or correlation between the molecular shapes of two molecules. The concept can be generalized to any two objects. For example, two pieces of a jigsaw puzzle that fit each other exhibit strong shape complementarity. It should be understood that, unless otherwise indicated, such examples and explanations could more generally apply to molecular combinations wherein more than two molecular subsets bind or interact with one another, representing the whole of, or portion(s) of, one or more target molecules and/or one or more ligands.

As an example, in one embodiment of the present invention the molecular combination may represent a target interacting with a ligand (i.e., target-ligand pair) where one molecular subset is from the protein and the other the ligand. In a further embodiment, the molecular combination may represent a target-ligand pair where one molecular subset is the entire ligand biomolecule but the other molecular subset is a portion of a target biopolymer containing one or more relevant active sites.

In yet another embodiment, the molecular combination may feature more than two molecular subsets, one representing a target (whole or part) and the other two correspond to two distinct ligands interacting with the same target at the same time, such as in the case of competitive thermodynamic equilibrium between a possible inhibitor and a natural binder of a protein. In yet another embodiment the previous example may be turned around such that the molecular combination features two target molecules in competition with one ligand biomolecule.

As another example, in one embodiment the molecular combination may represent a protein-protein interaction in which there are two molecular subsets, each representing the whole or a relevant portion of one protein. In a further embodiment, the molecular combinations may also represent a protein-protein interaction, but now with potentially more than two molecular subsets, each representing an appropriate protein domain.

As a further example, the molecular combination may feature two molecular subsets representing a target-ligand pair but also additional molecular subsets representing other atoms or molecules (heteroatoms or heteromolecules) relevant to the interaction, such as, but not limited to, one or more catalytic or structural metal ions, one or more ordered, bound, or structural water molecules, one or more salt molecules, or even other molecules such as various lipids, carbohydrates, acids, bases, mRNA, ATP/ADP, etc. In yet another embodiment, the molecular combination may feature two molecular subsets representing a target-ligand pair but also one or more added molecular subsets representing a whole or portion of a cell membrane, such as a section of a lipid bi-layer, nuclear membrane, etc., or a whole or portion of an organelle such as a mitochondrion, a ribosome, endoplasmic reticulum, etc.

In another embodiment, the molecular combination may feature two or more molecular subsets, with one or more molecular subsets representing various portions of a molecular complex and another subset representing the ligand interacting with the complex at an unoccupied active site, such as for proteins complexed with an allosteric activator or for proteins containing multiple, distinct active sites.

In another embodiment, the molecular combination may feature two or more molecular subsets representing protein chains or subunits interacting noncovalently as per a quaternary protein structure. In another embodiment, the molecular combination may feature two or more molecular subsets representing protein secondary structure elements interacting as per a tertiary structure of a polypeptide chain, induced for example by protein folding or mutagenesis.

In many of the forthcoming examples and explanations, the molecular combination will represent the typical scenario of a target-ligand pair interacting with one another. As already mentioned in regards to the present invention, an analysis of a molecular combination may seek to determine whether, in what fashion, and/or to what degree or with what likelihood, a ligand will interact with a target molecule based on computations of shape complementarity. In another embodiment, the analysis may involve a plurality of molecular combinations, each corresponding to a different ligand, selected, for example, from a molecule library (virtual or otherwise), in combination with the same target molecule, in order to find one or more ligands that demonstrate high shape complementarity with the target, and are therefore likely to bind or otherwise react with the target. In such cases, it may be necessary to assign a score or ranking to each analyzed molecular combination based on the estimated maximal shape complementarity across a set of different configurations for each combination, in order to achieve relative comparison of relevant predicted bioactivity.

In such a scenario where each target-ligand pair is an individual combination, and if there are N ligands to be tested against one target, then there will be N distinct molecular combinations involved in the analysis. For sufficiently large molecule libraries, it may be necessary to analyze millions or more potential molecular combinations for a single target protein. In yet another embodiment, the analysis may be reversed and the plurality of molecular combinations represents a plurality of target molecules, each in combination with the same ligand biomolecule in the same environment. In other embodiments, the molecular combinations may represent multiple ligands and/or targets reacting simultaneously, i.e., more than just a target-ligand pair, and may also include various heteroatoms or molecules as previously discussed.

FIG. 1 illustrates a modeling system 100 for the analysis of molecular combinations based on computations of shape complementarity across a set of configurations for the molecular combination. As shown a configuration analyzer 102 receives one or more input (or reference) configuration records 106, including relevant structural, chemical, and physical data associated with input structures for both molecular subsets from an input molecular combination database 104. The configuration analyzer 102 comprises a configuration data transformation engine 108 and a shape complementarity engine 109. Results from the configuration analyzer 102 are output as configuration results records 111 to a configuration results database 110.

Modeling system 100 may be used to efficiently analyze molecular combinations via computations of shape complementarity. In some embodiments, this may include, but is not limited to, prediction of likelihood of formation of a potential molecular complex, or a proxy thereof, the estimation of the binding affinity between molecular subsets in the molecular combination, the prediction of the binding mode (or even additional alternative modes) for the molecular combination, or the rank prioritization of a collection of molecular subsets (e.g., ligands) based on maximal shape complementarity with a target molecular subset across sampled configurations of the combination, and would therefore also include usage associated with computational target-ligand docking.

Furthermore, the method provides for performing a dense search in the configurational space of two or more molecular subsets having rigid bodies, that is, assessing relative orientations and translations of the constituent molecular subsets. The method can also be used in conjunction with a process for generating likely yet distinct conformations of one or both molecular subsets, in order to better analyze those molecular combinations where one or both of the molecular subsets are flexible.

In a typical operation, many molecular combinations, each featuring many different configurations, may be analyzed. Since the total possible number of configurations may be enormous, the modeling system 100 may sample a subset of configurations during the analysis procedure according to an appropriate sampling scheme as will be discussed later. However, the sampled subset may still be very large (e.g., millions or even possibly billions of configurations per combination). A shape complementarity score is generated for each sampled configuration and the results for one or more configurations recorded in a storage medium.

The molecular combination may then be assessed by examination of the set of configuration results including the corresponding computed shape complementarity scores. Once the cycle of computation is complete for one molecular combination, modeling of the next molecular combination may ensue. Alternatively, in some embodiments of the modeling system 100, multiple molecular combinations may be modeled in parallel. Likewise, in some embodiments, during modeling of a molecular combination, more than one configuration may be processed in parallel as opposed to simply in sequence.

In one embodiment, modeling system 100 may be implemented on a dedicated microprocessor, ASIC, or FPGA. In another embodiment, modeling system 100 may be implemented on an electronic or system board featuring multiple microprocessors, ASICs, or FPGAs. In yet another embodiment, modeling system 100 may be implemented on or across multiple boards housed in one or more electronic devices. In yet another embodiment, modeling system 100 may be implemented across multiple devices containing one or more microprocessors, ASICs, or FPGAs on one or more electronic boards and the devices connected across a network.

In some embodiments, modeling system 100 may also include one or more storage media devices for the storage of various, required data elements used in or produced by the analysis. Alternatively, in some other embodiments, some or all of the storage media devices may be externally located but networked or otherwise connected to the modeling system 100. Examples of external storage media devices may include one or more database servers or file systems. In some embodiments involving implementations featuring one or more boards, the modeling system 100 may also include one or more software processing components in order to assist the computational process. Alternatively, in some other embodiments, some or all of the software processing components may be externally located but networked or otherwise connected to the modeling system 100.

In some embodiments, results records from database 110 may be further subjected to a configuration selector 112 during which one or more configurations may be selected based on various results criteria and then resubmitted to the configuration analyzer 102 (possibly under different operational conditions) for further scrutiny (i.e., a feedback cycle). In such embodiments, the molecular configurations are transmitted as inputs to the configuration analyzer 102 in the form of selected configuration records 114. In another embodiment, the configuration selector 112 may examine the results records from database 110 and construct other configurations to be subsequently modeled by configuration analyzer 102. For example, if the configuration analyzer modeled ten target-ligand configurations for a given target-ligand pair and two of the configurations had substantially higher estimated shape complementarity than the other eight, then the configuration selector 112 may generate further additional configurations that are highly similar to the top two high-scoring configurations and then schedule the new configurations for processing by configuration analyzer 102.

In some embodiments, once analysis of a molecular combination is completed (i.e., all desired configurations assessed) a combination post-processor 116 may used to select one or more configuration results records from database 110 in order to generate one or more either qualitative or quantitative measures for the combination, such as a combination score, a combination summary, a combination grade, etc., and the resultant combination measures are then stored in a combination results database 118. In one embodiment, the combination measure may reflect the configuration record stored in database 110 with the best-observed shape complementarity. In another embodiment, multiple configurations with high shape complementarity are submitted to the combination post-processor 116 and a set of combination measures written to the combination results database 118. In another embodiment, the selection of multiple configurations for use by the combination post-processor 116 may involved one or more thresholds or other decision-based criteria.

In a further embodiment, the combination measures output to the combination results database 118 are based on various statistical analysis of a sampling of possibly a large number of configuration results records stored in database 110. In other embodiment the selection sampling itself may be based on statistical methods (e.g., principal component analysis, multidimensional clustering, multivariate regression, etc.) or on pattern-matching methods (e.g., neural networks, support vector machines, etc.)

In another embodiment, the combination post-processor 116 may be applied dynamically (i.e., on-the-fly) to the configuration results database 110 in parallel with the analysis of the molecular combination as configuration results records become available. In yet another embodiment, the combination post-processor 116 may be used to rank different configurations in order to store a sorted list of either all or a subset of the configurations stored in database 110 that are associated with the combination in question. In yet other embodiments, once the final combination results records, reflecting the complete analysis of the molecular combination by the configuration analyzer 102, have been stored in database 118, some or all of the configuration records in database 110 may be removed or deleted in order to conserve storage in the context of a library screen involving possibly many different molecular combinations. Alternatively, some form of garbage collection may be used in other embodiments to dynamically remove poor configuration results records from database 110.

In one embodiment, the molecular combination record database 104 may comprise one or more molecule records databases (e.g., flat file, relational, object oriented, etc.) or file systems and the configuration analyzer 102 receives an input molecule record corresponding to an input structure for each molecular subset of the combination. In another embodiment, when modeling target protein-ligand molecular combinations, the molecular combination record database 104 is replaced by an input target record database and an input ligand (or drug candidate) record database. In a further embodiment, the input target molecular records may be based on either experimentally derived (e.g., X-ray crystallography, NMR, etc.), energy minimized, or model-built 3-D protein structures. In another embodiment, the input ligand molecular records may reflect energy minimized or randomized 3-D structures or other 3-D structures converted from a 2-D chemical representation, or even a sampling of low energy conformers of the ligand in isolation. In yet another embodiment, the input ligand molecular records may correspond to naturally existing compounds or even to virtually generated compounds, which may or may not be synthesizable.

Figure 2A:
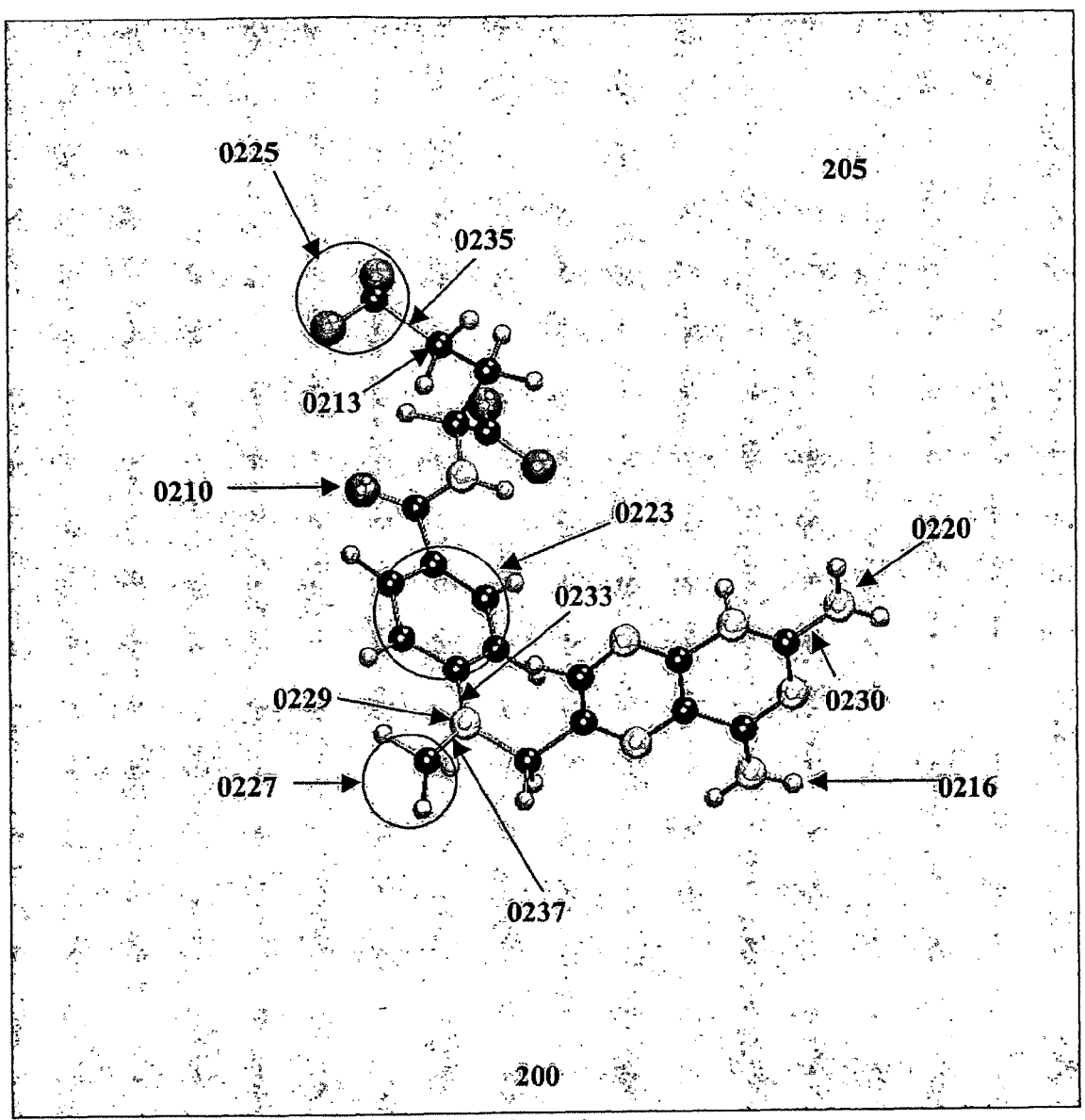
Figure 2C:
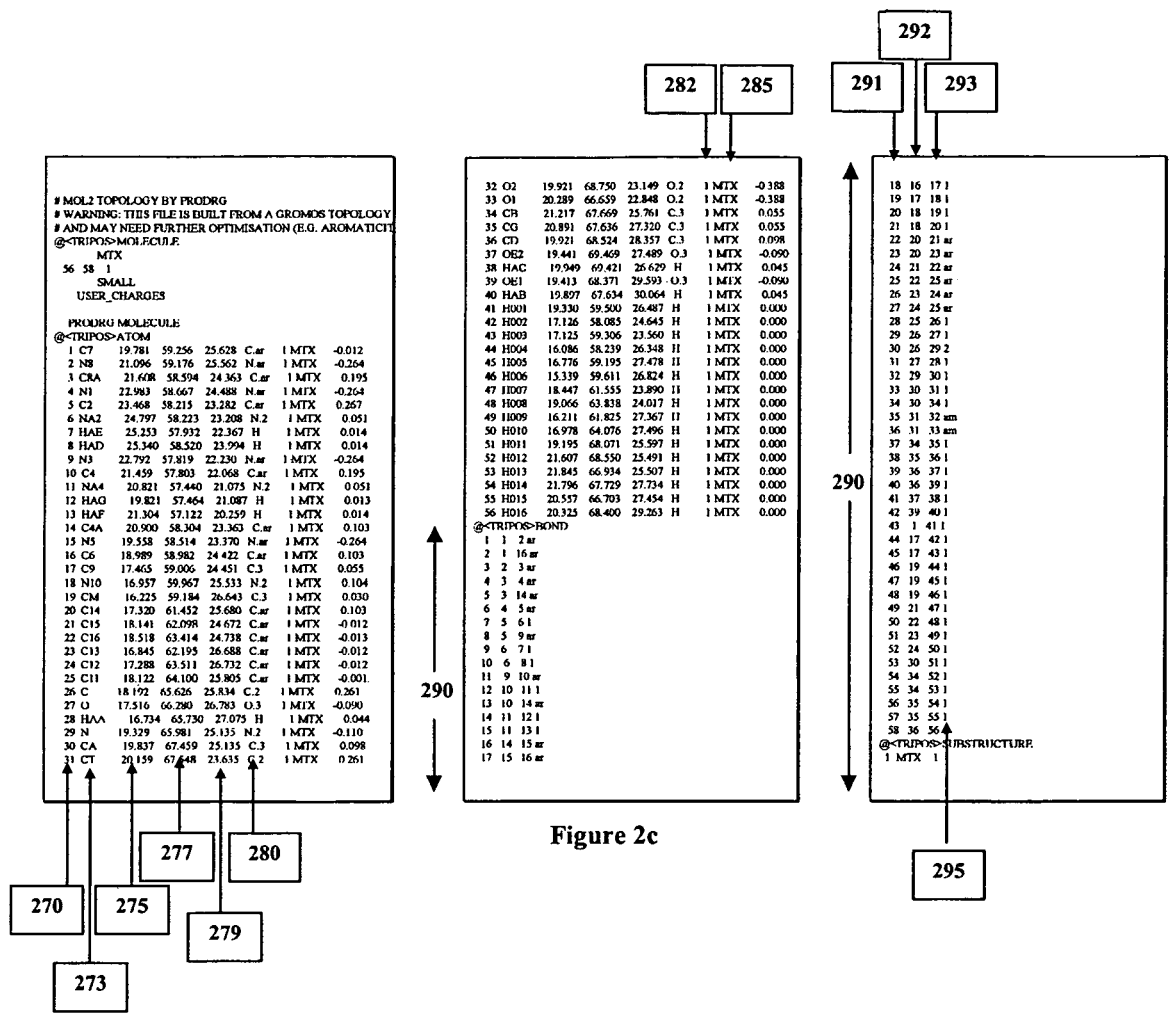

In order to better illustrate an example of an input structure and the associated input molecule record(s) that may form an input configuration record submitted to configuration analyzer 102 we refer the reader to FIGS. 2a, 2b, and 2c.

FIG. 2a shows a "ball-and-stick" rendering of a pose 205 of a methotrexate molecule 200 with chemical formula $C_{20}H_{22}N_8O_5$. The depicted molecular subset comprises a collection of atoms 220 and bonds 230. The small, black atoms, as indicated by item 213, represent carbon atoms. The tiny, white atoms, as indicated by item 216, represent hydrogen atoms, whereas the slightly larger dark atoms (item 210) are oxygen atoms and the larger white atoms (item 229) are nitrogen atoms. Continuing in FIG. 2a, item 223 denotes a circle containing a benzene ring ($C_6H_4$), and item 225 a circle containing a carboxyl group ($COO^-$), and item 227 another circle containing a methyl group ($CH_3$). Item 233 denotes a covalent bond connecting the benzene ring 223 to the ester group that includes the methyl group 227. Item 235 denotes a covalent bond connecting the carbon atom 213 to the carboxyl group 225. Lastly item 237 denotes a covalent bond connecting the methyl group 227 to a nitrogen atom 229.

FIG. 2b shows a pdb file representation 240 of a chemical structure for the methotrexate ligand pose described in FIG. 2a, including a general header 250, a section 260 composed of atom type and coordinate information, and a section 265 regarding bond connectivity information. The header section 250 may contain any annotation or other information desired regarding the identity, source, or characteristics of the molecular subset and its conformation and/or stereochemistry. Section 0260 shows a list of all 33 nonhydrogen atoms of methotrexate and for each atom it includes a chemical type (e.g., atomic element) and three spatial coordinates. For instance, the line for atom 6 shows that it is a nitrogen atom with name NA4 in a compound (or residue if a protein) named MTX in chain A with compound (or residue) id of 1 and with (x, y, z) coordinates (20.821, 57.440, 21.075) in a specified Cartesian coordinate system. Note that the compound or residue name field may be more relevant for amino or nucleic acid residues in biopolymers.

Section 265 of the PDB file 240, sometimes called the connect record of a PDB file, describes a list of the bonds associated with each atom. For instance, the first line of this section shows that atom 1 is bonded to atoms (2), and (12), whereas the second line shows that atom 2 is bonded to atoms (1), (3), and (4). Notice also how in this example hydrogens are missing and as such the bond connections for each atom may not be complete. Of course, completed variants of the PDB file representation are possible if the positions of hydrogen atoms are already specified, but in many cases where the chemical structure originates from experimental observations the positions of hydrogens may be very uncertain or missing altogether.

FIG. 2c shows a Tripos mol2 file containing various additional chemical descriptors above and beyond the information shown in the PDB file in FIG. 2b. Column 270 lists an index for each atom; column 273 lists an atom name (may be nonunique) for each atom; columns 275, 277, and 279 respectively list x, y, z coordinates for each atom in an internal coordinate system; column 280 lists a SYBYL atom type according to the Tripos force field [34] for each atom that codifies information for hybridization states, chemical type, bond connectivity, hydrogen bond capacity, aromaticity, and in some cases chemical group; and columns 282 and 285 list a residue id and a residue name for each atom (relevant for proteins, nucleic acids, etc.). Section 290 lists all bonds in the molecular subset. Column 291 lists a bond index for each bond; columns 292 and 293 the atom indices of the two atoms connected by the bond; and column 295 the bond type, which may be single, double, triple, delocalized, amide, aromatic, or other specialized covalent bonds. In other embodiments such information may also represent noncovalent bonds such as salt bridges or hydrogen bonds. In this example, notice how the hydrogen atoms have now been included.

In one embodiment the configuration data transformation engine 108 may directly transform one or more input molecular configurations into one or more other new configurations by application of various rigid body transformations. In other embodiments, the configuration data transformation engine 108 may instead apply rigid body transformations to sets of basis expansion coefficients representing molecular shapes for reference poses for each molecular subset as will be discussed in more detail later in the technical description. In some embodiments, the set of configurations visited during the course of an analysis of a molecular combination may be determined according to a schedule or sampling scheme specified in accordance with a search of the permitted configuration space for the molecular combination.

In some embodiments, whether generated by direct transformation of structural coordinates or by transformation of sets of basis expansion coefficients, the configuration data transformation engine 108 may produce new configurations (or new sets of basis expansion coefficients corresponding to new configurations) sequentially and feed them to the shape complementarity engine 109 in a sequential manner, or may instead produce them in parallel and submit them in parallel to the shape complementarity engine 109.

The shape complementarity engine 109 is responsible for generating a shape complementarity score or equivalent measure for each sampled configuration of the molecular combinations and makes use of the present invention to efficiently compute the shape complementarity for each configuration based on use of basis expansions and rigid body transformations of molecular shapes. The shape complementarity engine 109 may also include one or more storage components for data specific to the computations of shape complementarity.

In some embodiments, the configuration results records 111 may include a quantitative measure related to the shape complementarity evaluated for each configuration. In one embodiment, this may be a score. In another embodiment, this may be a probability. In other embodiments, the configuration results records 111 may include a qualitative measure related to the shape complementarity evaluated for the configuration. In one embodiment, this may be a grade. In another embodiment this may be a categorization (i.e., poor, weak, strong, etc.). In yet another embodiment this may be a simple pass-fail measure.

In many embodiments, the configuration results records 111 may also include information used to specify the identity and/or nature of configuration corresponding to a given shape complementarity score. In addition to the identity of the interacting molecular subsets, there may be a need to annotate or otherwise represent the geometrical state of the configuration.

Typically this may be achieved by storing the parameters of the rigid body transformation used to generate the configuration from an input or reference configuration.

In some embodiments, the configuration selector 112 may utilize various selection criteria in order to resubmit certain configurations back to modeling system 102 for more computations. In one embodiment, the selection criteria may be predicated on passing of a threshold or other decision mechanism based on one or more qualitative affinity measures. In another embodiment, the selection criteria may be based on a threshold or other decision mechanism based on one or more quantitative shape complementarity scores.

In yet another embodiment, the selection criteria used by the configuration selector 112 may be based on various statistical analysis of a number of different configuration results records stored in database 110, including, but not limited to, principal component analysis, multidimensional clustering, Bayesian filters, multivariate regression analysis, etc. In yet another embodiment, the selection criteria may be based on various pattern matching analysis of a number of different configuration results records stored in database 110, including, but not limited to, use of neural networks, support vector machines, hidden Markov models, etc.

In some embodiments, the configuration data transformation engine 108 may receive certain resubmitted configurations from the configuration selector 112 and utilize them as inputs to start a new cycle of shape complementarity computations. For example, if a particular configuration was selected from database 110 based on high shape complementarity by the configurations selector 112, the configuration data transformation engine 108 may generate multiple configurations (or multiple sets of basis expansion coefficients corresponding to new configurations) that are similar (i.e., slightly different positions and orientations for each molecular subset) in order to better investigate that portion of the possible configuration space of the molecular combination. In other embodiments, the new cycle of shape complementarity computations instigated by the resubmission of the selected configurations records 114 may involve the operation of the configuration analyzer 102 under a different set of conditions or using a different set of control parameters. In further embodiments, the selected configurations records 114 may kick off a new cycle of shape complementarity computations using a different variant of the configuration analyzer 102, including the use of a modified formulation for subsequent shape complementarity scores (if appropriate).

Figure 3:
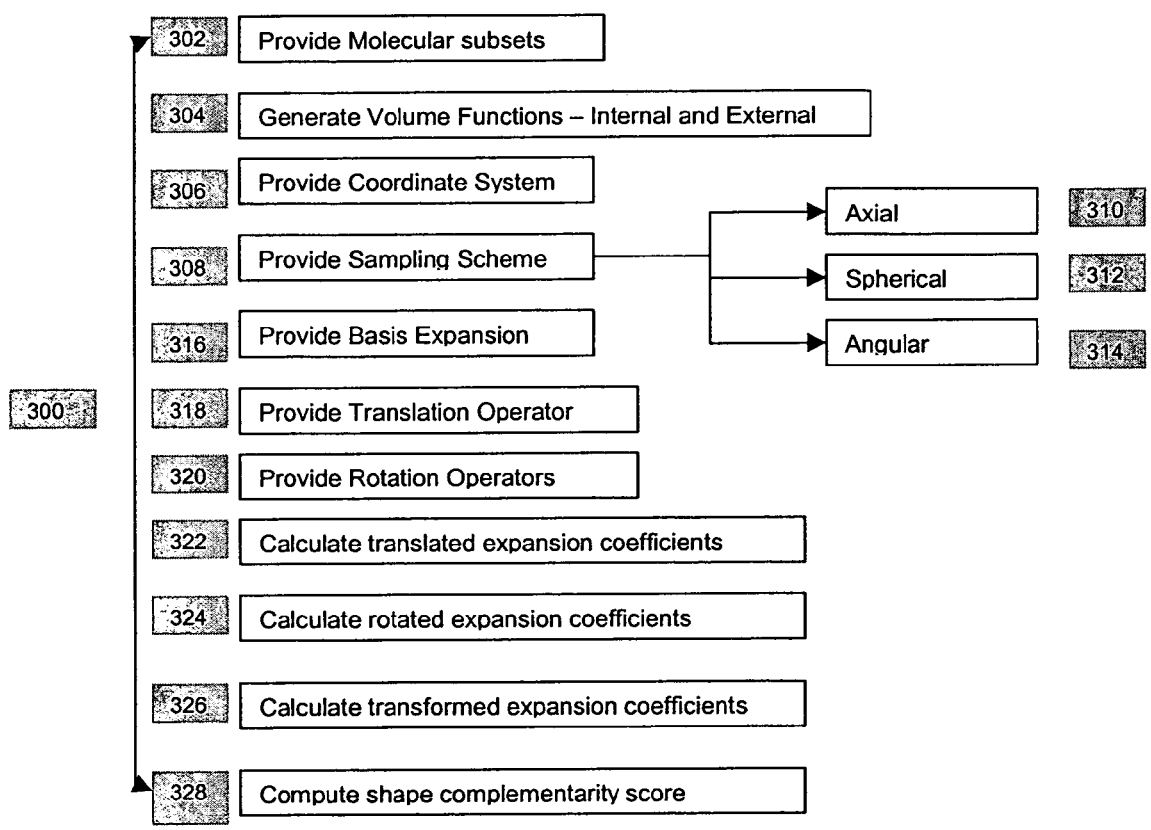
FIG. 3 shows a flow diagram of an exemplary method of assessing shape complementarity of two molecular subsets, performed in accordance with embodiments of the present invention.

FIG. 3 shows a flow diagram of an exemplary method 300 of analyzing a molecular combination based on computations of shape complementarity across a set of configurations, performed in accordance with embodiments of the present invention. The method 300 of FIG. 3 is described with reference to FIGS. 4-15. As explained below, the method 300 generally involves computing a basis expansion representing molecular shapes of the constituent molecular subsets, computing transformed expansion coefficients for different configurations (i.e., relative positions and orientations) of the molecular subsets, and computing a correlation function representing a shape complementarity of the two molecular subsets using the transformed expansion coefficients. Embodiments of this method incorporate various combinations of hardware, software, and firmware to perform the steps described below.

Figure 4:
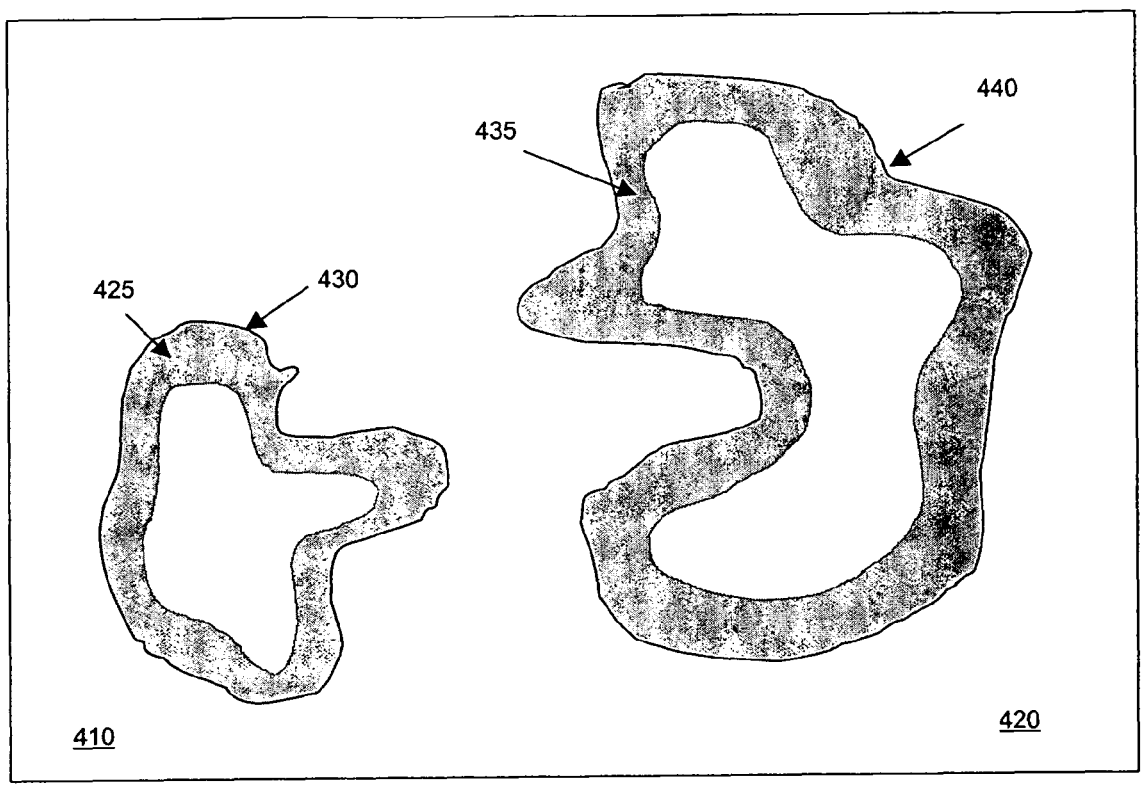
FIG. 4 shows illustrations of two molecular subsets assessed in accordance with embodiments of the present invention.
Figure 5:
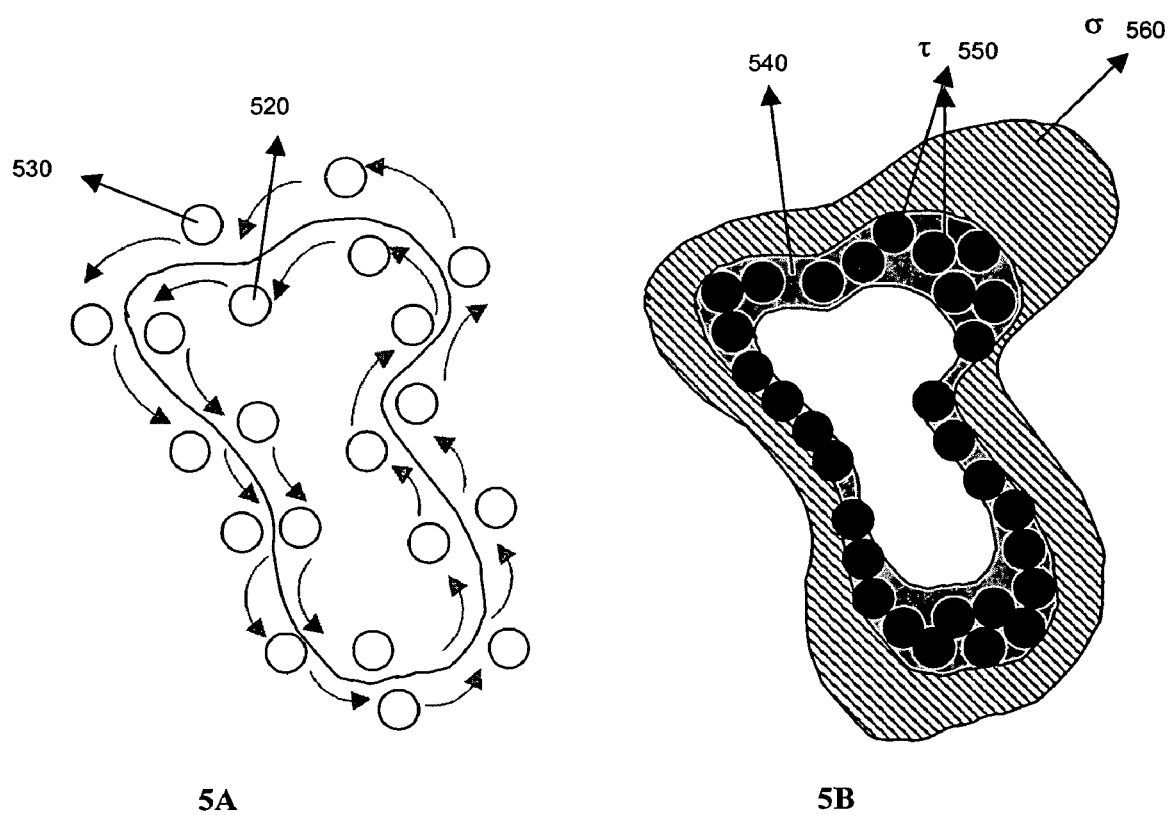
FIGS. 5A and 5B show two molecular subsets having internal and external volume functions generated in accordance with embodiments of the present invention.

In FIG. 3, in step 302, a first molecular subset 410 and a second molecular subset 420 are provided, as shown in FIG. 4. Each molecular subset has a molecular shape, illustrated in FIG. 4. As used herein, "molecular shape" generally refers to a volumetric function representing the structure of a molecular subset comprising a plurality of atoms and bonds. Those skilled in the art will appreciate that the molecular subsets may have various shapes other than those shown in FIG. 4. The first molecular subset 410 has a plurality of atoms and bonds. Some of these atoms in the first molecular subset are surface atoms 425. The surface atoms are proximal to and define a molecular surface 430 for the first molecular subset 410 based on the location of those surfaced atoms 425. Similarly, the second molecular subset 420, as shown in FIG. 4, also has a plurality of atoms and bonds. Some of the atoms in the second molecular subset are surface atoms 435, the locations of which define a molecular surface 440 for the second molecular subset 420. The molecular surface 430 of the first molecular subset can be a solvent accessible molecular surface, which is generally the surface traced by the center of a small sphere rolling over the molecular surface 430. As used herein, "solvent" generally refers to the plurality of atoms, ions, and/or simple molecules (e.g., water, salt, sugars) that comprise an ambient medium, polarizable or otherwise. Computational methods for generation of solvent accessible surfaces includes the method presented in Connolly, M. L., "Analytical molecular surface calculation.", (1983), *J. Applied Crystallography*, 16, 548-558; all of which is hereby incorporated in its entirety.

In FIG. 4, often the first molecular subset 410 is a ligand, and the second molecular subset 420 is a protein. However, as already discussed in regards to the definition of a molecular subset, the molecular subsets 410 and 420 can have various compositions.

In FIG. 3, in step 304, a first internal volume function is generated. This first internal volume function is a representation of the subset of a volume enclosed by the first molecular surface 430 of molecular subset 410. As used herein, the "internal volume function" of a molecular subset is generally any subset of the 3-D volume enclosed by the molecular surface. In one embodiment, the first internal volume function is defined as a union of a set of kernel functions, where generally a kernel function is a 3-D volumetric function with finite support in a localized neighborhood about an atom and/or bond, and where each kernel function is associated with atoms and/or bonds in the first molecular subset 410.

In one embodiment, the kernel function used in defining an internal volume function is a 3-D Gaussian function localized around the center of an atom. In other embodiments, each kernel function can be dependent on the chemical identity of associated atoms and/or bonds. Alternatively, the kernel function can be dependent on the location of the associated atom or bond within a chemical group. In one embodiment, the kernel function associated with an atom is a nonzero constant for positions within a Van der Waals (VdW) sphere, i.e., a sphere with radius equal to the VdW radius of an atom of the given type and centered on the atom, and has a value of zero at other positions. This nonzero constant can have a value of unity, for example.

In another embodiment, the first internal volume function is further specified by intersection with a proximal surface volume defined by the movement of a probe sphere 520 (white balls), as shown in FIG. 5A, which moves at positions proximal to and internal to a first molecular surface 510 for the first molecular subset 410. The proximal surface volume is shown in FIG. 5B as the shaded region 540, which depicts the same molecular subset 410, and the first internal volume function resulting from the intersection of the molecular subset and region 540 is displayed as the volume occupied by the dark balls 550 also in FIG. 5B. In yet another embodiment, the first internal volume function is wholly comprised of the proximal surface volume depicted in FIG. 5B as the shaded region 540.

Similarly, a second internal volume function may be generated for the second molecular subset 420 and can be defined in a similar manner as the first internal volume function.

Also in step 304 of FIG. 3, external volume functions are defined for both the first molecular subset and the second molecular subset. As used herein, the "external volume function" of a molecular subset is generally any subset of the 3-D volume external to the molecular surface of that molecular subset. A first external volume function is generated as a representation of a subset of a volume external to the first molecular surface. As shown in FIG. 5A, this external volume function can be defined by the movement of a probe sphere 530 (white balls) that moves at positions proximal to and external to the first molecular surface 510. Similarly, a second external volume function is defined for the second molecular subset.

In one embodiment, when the volume functions are generated, the probe spheres 520 (internal) or 530 (external) travels along the entire molecular surface 510, while in another embodiment, the probe sphere moves along a portion of the molecular surface 510. In one embodiment, the probe sphere has a constant radius, while in another embodiment the radius of the probe sphere varies as a function of the location of the probe sphere on the molecular surface.

In FIG. 5B, the external volume function and the internal volume function for first molecular subset 410 are shown. In FIG. 5B, the region 550, represented as a union of dark balls, identifies the volumetric domain of the internal volume function, $\tau$, while the diagonal dashed region 560 represents the volumetric domain of the external volume function, $\sigma$, of the first molecular subset 410. The volumetric domains for $\tau$ and $\sigma$ may be similarly identified for the second molecular subset 420. The volumetric functions, $\tau$ and $\sigma$, are used to calculate shape correlations, as described below.

In one embodiment, described with reference to FIG. 6, the first and second molecular subsets 410 and 420 are represented in discrete space 600 in order to generate the respective internal and external volume functions. As used herein, "discretization" generally refers to converting a continuous representation to a discrete one, e.g., converting the function from its continuous representation into a series of numbers that best approximates the continuous function as projected onto a set of grid cells.

Figure 7:
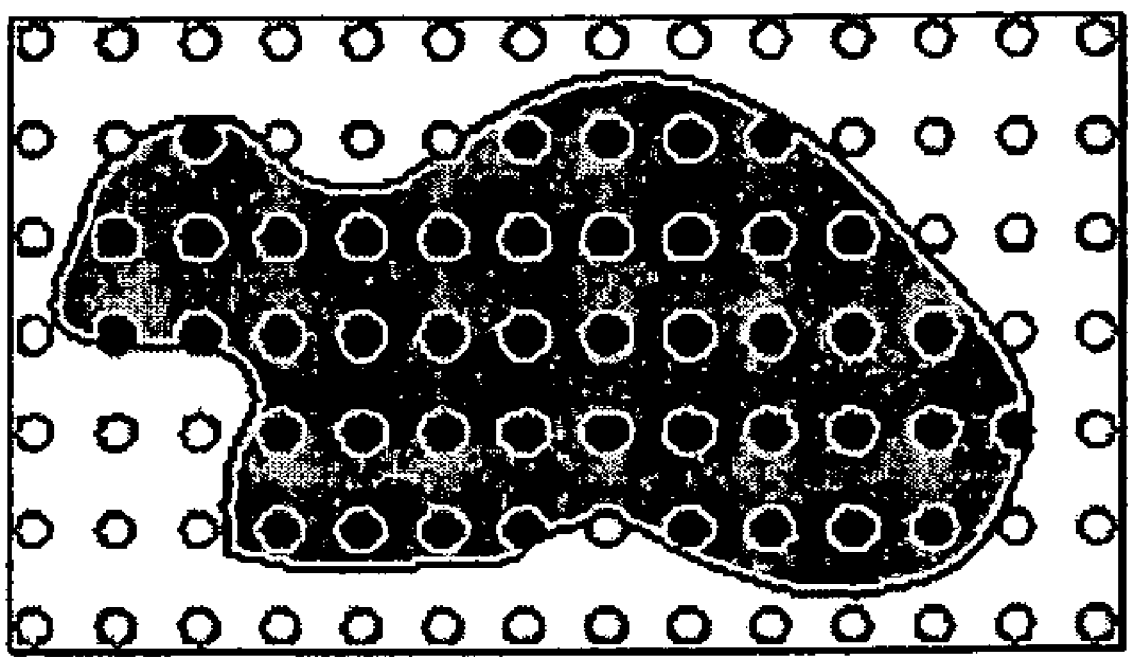
FIG. 7 illustrates how a 2-D continuous shape is discretized in accordance with embodiments of the present invention.

For example, the FIG. 7 illustrates how a general 2-D continuous shape is discretized on a 2-D rectilinear grid. The black dots represent centers of the occupied grid cells; the white dots represent centers of unoccupied grid cells.

Figure 6:
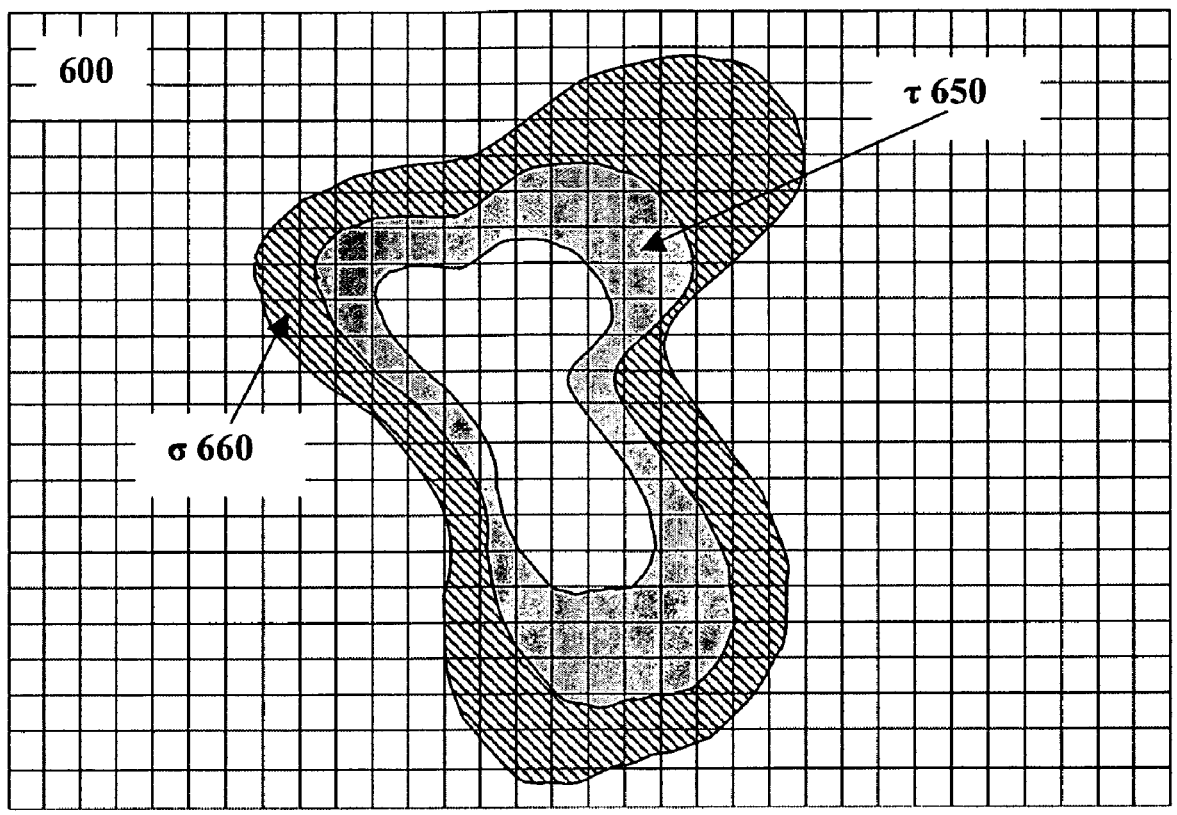
FIG. 6 shows representations of two molecular subsets in discrete space for generating internal and external volume functions, in accordance with embodiments of the present invention.

In FIG. 6, the external volume function, $\sigma$, for a particular grid cell is assigned a nonzero numerical value when a grid cell is inside the volumetric domain 660 of FIG. 6, i.e., the grid cell is occupied, and zero otherwise. Similarly, the internal volume function, $\tau$, for a particular grid cell is assigned a nonzero numerical value when the grid cell is inside the volumetric domain 650 of FIG. 6, and zero otherwise. In one embodiment only a significant fraction of the grid cell must lie within the appropriate domain in order for the grid cell to be considered occupied.

While FIG. 6 shows a two-dimensional cross-sectional view of the volume functions for the molecular subsets and a 2-D Cartesian grid, those skilled in the art should understand that the principles described above are equally applicable to three-dimensional and higher multidimensional spaces, as well as to other coordinate based representations, where the phrase "coordinate based representation" generally refers to representing a function in terms of coordinates of a coordinate system.

In one embodiment, a Cartesian coordinate based representation is used where each grid cell in three-dimensions is a cuboid. The cuboid grid cells in FIG. 6 with nonzero values for $\sigma$ are illustrated as having horizontal stripes, and those with nonzero values for $\tau$ are illustrated as having vertical stripes. In this way, values are assigned to $\sigma$ and $\tau$, for each grid cell so that the internal and external volume functions are represented as a set of numbers for the entirety of grid cells. In one embodiment, the positive numerical value assigned when a grid cell is occupied is unity and thus the representative set of numbers is a 3-D bitmap.

Figure 8:
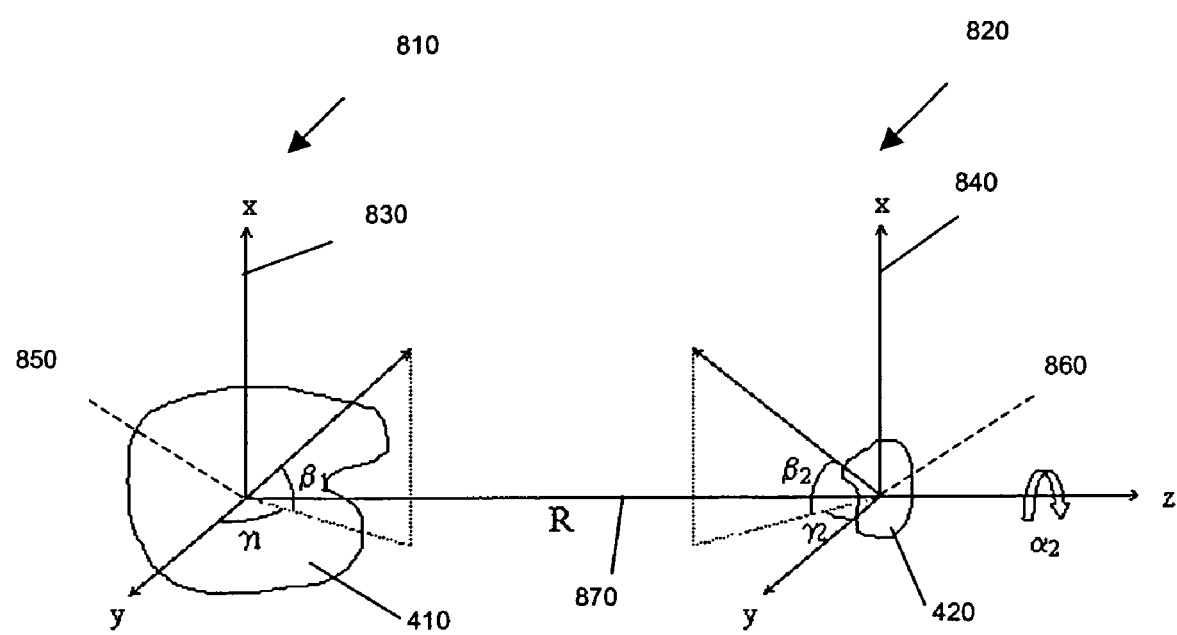
FIG. 8 shows coordinate-based representations of two molecular subsets in a joint coordinate system, in accordance with embodiments of the present invention.
Figure 9A:
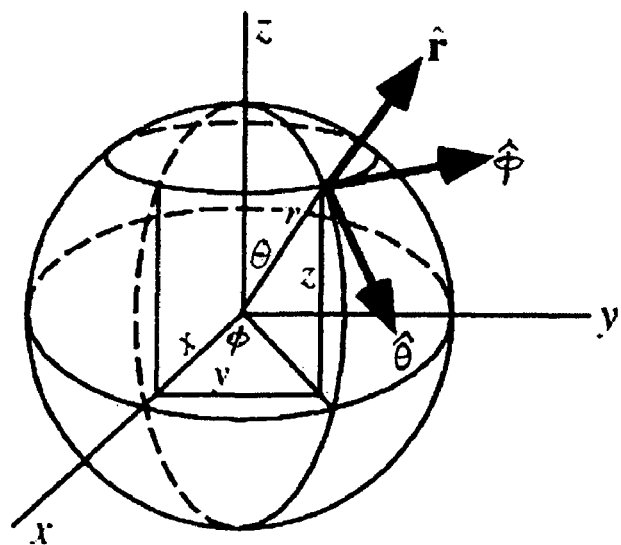
FIG. 9 shows the representation of various coordinate systems used in the present invention.
Figure 9B:
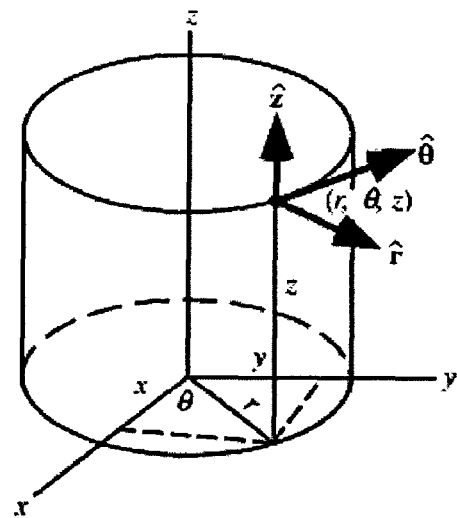
Figure 9C:
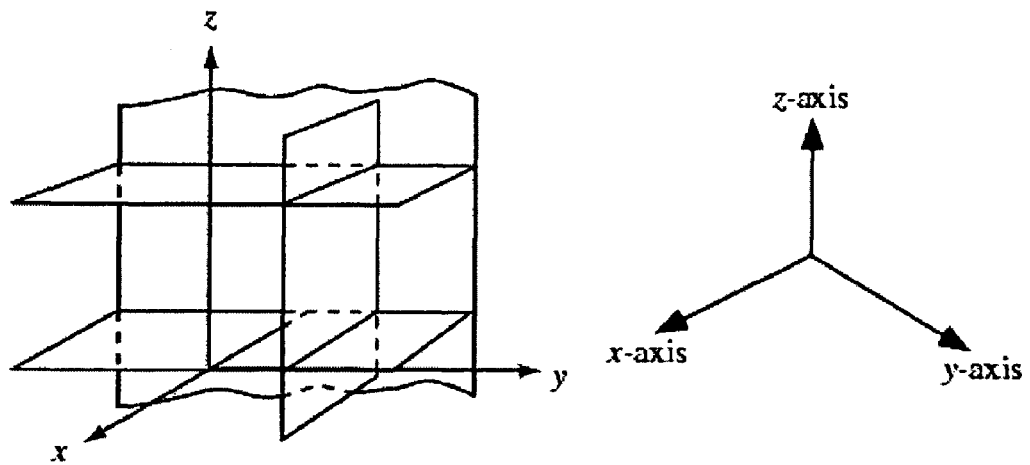

In FIG. 3, in step 306, the method 300 includes defining individual coordinate-based representations for the molecular subsets 410 and 420, whereby each molecular subset is represented in a coordinate system. A three-dimensional coordinate system is a systematic way of describing points in three-dimensional space using sets of three numbers (or points in a plane using pairs of numbers for a two-dimensional space). As shown in FIG. 8, an individual coordinate based representation of the first molecular subset 410 is defined using a first coordinate system 810. An individual coordinate based representation of the second molecular subset 420 is defined using a second coordinate system 820.

In one embodiment, the individual coordinate based representations are defined using a spherical polar coordinate system. The spherical polar coordinate system is a three-dimensional coordinate system where the coordinates are as follows: a distance from the origin r, and two angles $\theta$ and $\phi$ found by drawing a line from the given point to the origin and measuring the angles formed with a given plane and a given line in that plane. Angle $\theta$ is taken as the polar (co-latitudinal) coordinate with $\theta \in [0, \pi]$ and angle $\phi$ is the azimuthal (longitudinal) coordinate with $\phi \in [0, 2\pi]$. An illustration is provided in FIG. 9a.

In another embodiment, the individual coordinate based representations are defined using a cylindrical coordinate system (FIG. 9b), which is another three dimensional coordinate system where the coordinates are described in terms of (r, $\theta$, z), where r and $\theta$ are the radial and angular components on the (x, y) plane and z component is the z-axis coming out of the plane.

In yet another embodiment, the individual coordinate based representations are defined using a Cartesian coordinate system. The Cartesian coordinate system describes any point in three-dimensional space using three numbers, by using a set of three axes at right angles to one another and measuring distance along these axes. The three axes of three-dimensional Cartesian coordinates conventionally denoted the x-, y- and z-axis are chosen to be linear and mutually perpendicular. In three dimensions, the coordinates can lie anywhere in the interval $[-\infty, +\infty]$. An illustration is provided in FIG. 9c.

For practical purposes of computation in software and/or hardware, the individual coordinate based representations are generally discrete in nature. The individual coordinate based representations are used to compute a reference set of basis expansion coefficients as described below.

A point in space can be represented in many different coordinate systems. It is possible to convert from one type of coordinate based representation to another by means of a coordinate transformation. A coordinate transformation is a method for relabeling the coordinates from one coordinate system in terms of another coordinate system. For example, the following equations represent the transformation between Cartesian and spherical polar coordinates: {x=r sin θ cos φ, y=r sin θ sin φ, z=r cos φ}, and thus a Cartesian coordinate base representation for the internal volume function for molecular subset 410 can be converted to a spherical polar coordinate based representation for the internal volume function for molecular subset 410 by applying an appropriate Cartesian to spherical coordinates transform.

In FIG. 3, also in step 306, the individual coordinate based representations 810 and 820 of the first and second molecular subsets are then placed in a joint coordinate system, as shown in FIG. 8. The joint coordinate system is used to represent distinct configurations of the molecular combination. The joint coordinate system is also used to generate new configurations by translating and/or rotating the respective individual coordinate based representations of molecular subsets 410 and 420 relative to one another, as described below. In one embodiment, the joint coordinate system is also used to transform a reference set of basis expansion coefficients for each molecular subset as part of a process to generate shape complementarity scores for each configuration of a molecular combination, as described below.

In one embodiment, a first three-dimensional Cartesian frame 830 is provided for the first molecular subset 410, and a second three-dimensional Cartesian frame 840 is provided for the second molecular subset, as shown in FIG. 8. "Cartesian frame" generally refers to the unit vectors in the Cartesian coordinate system, as illustrated in FIG. 3c.

In FIG. 8, the first and second Cartesian frames 830 and 840 are centered at respective molecular centers 850 and 860 of the first and second molecular subsets. The molecular center is generally a point in 3-D space that is designated as the center of the molecular subset. In one embodiment, the molecular center is the geometric center of mass of the molecular subset. In another embodiment, the molecular center is the centroid of the molecular subset. An intermolecular axis 870 is defined as the vector between the molecular centers 850 and 860, and the Z-axes of the respective Cartesian frames 830 and 840 are both aligned with the intermolecular axis 870.

In principal, any rotation in three dimensions may be described using three angles. The three angles giving the three rotation matrices are called Euler angles. There are several conventions for Euler angles, depending on the axes about which the rotations are carried out. In a common convention described in FIG. 10, the first rotation is by angle φ about z-axis, the second is by angle θ∈[0, π] about x-axis, and the third is by angle ψ about z-axis (again). If the rotations are written in terms of rotation matrices B, C and D, then a general rotation A can be written as A=BCD where B, C, and D are shown below and A is obtained by multiplication of the three matrices.

$$D \equiv \begin{bmatrix} \cos\phi & \sin\phi & 0 \\ -\sin\phi & \cos\phi & 0 \\ 0 & 0 & 1 \end{bmatrix}, C \equiv \begin{bmatrix} 1 & 0 & 0 \\ 0 & \cos\theta & \sin\theta \\ 0 & -\sin\theta & \cos\theta \end{bmatrix}, \quad [\text{Eqn. 3}]$$

$$B \equiv \begin{bmatrix} \sin\psi & -\cos\psi & 0 \\ \cos\psi & \sin\psi & 0 \\ 1 & 1 & 1 \end{bmatrix}$$

Figure 10:
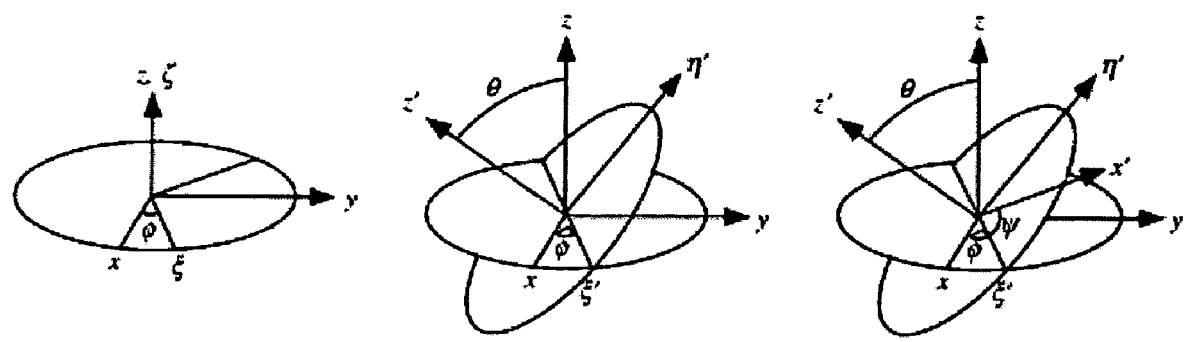
FIG. 10 shows a representation of Euler angles as used in various embodiments of the present invention.
Figure 11:
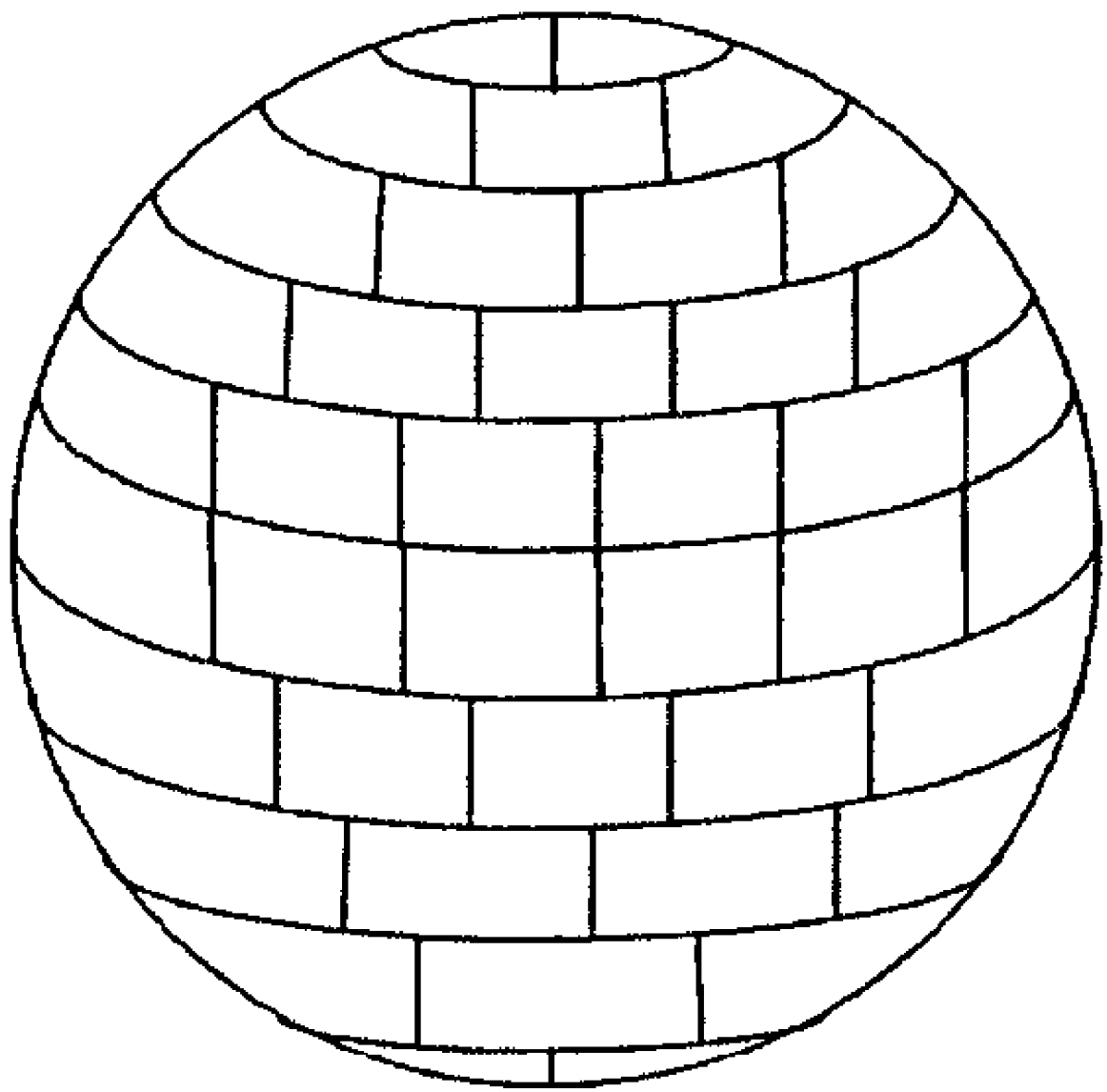
FIG. 11 shows a spherical sampling scheme used in embodiments of the present invention.

The diagrams in FIG. 10 are excerpted from web pages available at Eric Weisstein's World of Mathematics on the world-wide web at http://mathworld.wolfram.com/.

Another commonly used convention for Euler angles is the well-known "roll, pitch, and yaw" convention encountered in aeronautics. Herein, the roll Euler angle is the Euler angle representing a rotation, □ about the z-axis, the pitch Euler angle is the Euler angle representing a rotation, □, about the y-axis and the yaw Euler angle is the Euler angle representing a rotation, □, about x-axis.

In one embodiment, as shown in FIG. 8, R is the intermolecular separation between the first molecular subset 410 and the second molecular subset 420. $\beta_1$ and $\beta_2$ refer to pitch Euler angles representing rotation of each corresponding molecular subset in the x-z plane (i.e., around the y-axis). $\gamma_1$ and $\gamma_2$ refer to yaw Euler angles representing rotations in the y-z plane (i.e., around the x-axis). Therefore, $(\beta_1, \gamma_1)$ are polar and azimuthal Euler angles describing the pitch and yaw of the first molecular subset 410 with respect to the joint coordinate system, $(\beta_2, \gamma_2)$ are polar and azimuthal Euler angles describing the pitch and yaw of the second molecular subset 420 with respect to the joint coordinate system, and $\alpha_2$ is a twist Euler angle describing the roll of the second molecular subset 420 with respect to the intermolecular axis. In this way, a set of six coordinates, (R, $\beta_1$, $\gamma_1$, $\alpha_2$, $\beta_2$, $\gamma_2$), completely specify the configuration of the molecular combination, i.e., the relative position and orientation of the molecular subsets.

For practical purposes of computation in software and/or hardware, the coordinate variables of the joint coordinate system, (R,$\beta_1$,$\gamma_1$,$\alpha_2$,$\beta_2$,$\gamma_2$), are generally sampled as a discrete set of values. In other embodiments, the joint coordinate system may be characterized by a different set of parameters other than (R,$\beta_1$,$\gamma_1$,$\alpha_2$,$\beta_2$,$\gamma_2$). For example, ($\alpha_2$,$\beta_2$,$\gamma_2$) may be any one of several sets of permissible Euler angles for molecular subset 420. In another example the angular parameters are not Euler angles. In yet another example, the parameters of the joint coordinate system are expressed in terms of translation and rotation operators, defined below, as applied to (μ, ν, φ) of a prolate spheroidal coordinate system for each molecular subset.

In FIG. 3, as part of the sampling scheme definitions in step 308, an axial sampling scheme is defined in step 310. The axial sampling scheme has a plurality of axial sample points representing a sequence of positions distributed along the intermolecular axis 870 in FIG. 8. As used herein, a "sample point" generally refers to one of a sequence of elements defining the domain of a discretized function, and "sampling scheme" generally refers to a scheme for selecting a sequence of sample points.

An "axial sampling scheme" is a scheme for selecting sample points along an axis or a line (i.e., "axial sample points") and thus provides for relative translation of the individual coordinate based representation 810 of the first molecular subset with respect to the coordinate based representation 820 of the second molecular subset. The allowed values of the intermolecular separation, R, are defined by the axial sampling scheme. In another embodiment, the axial sampling scheme is a regular sampling scheme, which involves selecting sample points at regular intervals. In one embodiment, the axial sampling scheme is an irregular sampling scheme, which involves selecting sample points at irregular intervals according to a nonlinear mapping.

In one embodiment, the endpoints for the axial sampling scheme can be set based on geometric analysis of the molecular shapes 430 and 440 of both the first and second molecular subsets. In another embodiment, the geometric analysis constitutes a determination of a maximum radial extent of each molecular subset, and the endpoints of the axial sampling scheme for the first molecular subset 410 are set based on a function of the maximum radial extents of each molecular subset.

In FIG. 3, in step 312, a first spherical sampling scheme is defined for the first molecular subset 410. The first spherical sampling scheme has a plurality of spherical sample points representing a sequence of positions distributed on a surface of a first unit sphere centered on the molecular center of the first molecular subset. In one embodiment, the allowed values of the pitch and yaw Euler angels, $(\beta_1, \gamma_1)$, for molecular subset 410 are defined by the first spherical sampling scheme.

In one embodiment, the first spherical sampling scheme is the Cartesian product of a regular sampling of the pitch Euler angle ($\beta_1$) and a regular sampling of the yaw Euler angle ($\gamma_1$), where the Cartesian product of two sets A and B is a set of the ordered pairs, $\{(a, b) | a \in A, b \in B\}$ and either set is allowed to be a single element set. This is an example of an irregular sampling scheme in that spherical sample points near the poles will be closer together than at or near the equator.

In another embodiment, the first spherical sampling scheme is defined via an icosahedral mesh covering the two-dimensional surface of a sphere, where "icosahedral mesh" refers to the projection of all vertices and face centers of a many-sided icosahedron onto a unit sphere. In this way an evenly spaced 2-D grid can be constructed on the surface of the sphere as shown in the illustration in FIG. 11. This is an example of a regular sampling scheme in that each spherical sample point corresponds to the center of a 2-D surface element of approximately the same surface area. Similar icosahedral-based regular spherical sampling schemes are discussed in ref. [13].

A second spherical sampling scheme for the second molecular subset 420 can be constructed in the same manner as the first spherical sampling scheme. In this way, the allowed values of the pitch and yaw Euler angels, $(\beta_2, \gamma_2)$, for molecular subset 420 are defined by this second spherical sampling scheme.

In FIG. 3, in step 314, an angular sampling scheme is defined for the second molecular subset 420. The angular sampling scheme has a plurality of angular sample points representing a sequence of positions distributed on a circumference of a unit circle orthogonal to the intermolecular axis 870 disposed between the molecular centers of the two molecular subsets 410 and 420. The allowed values of the roll Euler angle, $\alpha_1$, for molecular subset 420 are defined by this angular sampling scheme. In one embodiment, the angular sampling scheme is a regular sampling scheme, representing intervals with uniform arc length. In another embodiment, the angular sampling scheme is an irregular sampling scheme.

In FIG. 3, in step 316, a basis expansion with a corresponding set of basis functions is provided. The "basis expansion," as used herein, refers to decomposition of a general function into a set of coefficients, each representing projection onto a particular basis function. One can express this decomposition in a mathematical form, i.e., a general function in M-dimensions, $f(\vec{x})$, can be written in terms of a set of basis functions $B_i(\vec{x})$, as $$f(\vec{x}) = \sum_{i=0}^{i=\infty} a_i B_i(\vec{x}) \quad [\text{Eqn. 4}]$$

where, $i \in \{0, 1, 2, \ldots \infty\}$ refers to a specific basis function, $\vec{x}$ is a set of M coordinates, and each basis function, $B_i$, is generally one member of a set of M-dimensional functions in a function space such that any general function in the function space can be expressed as a linear combination of them with appropriately chosen coefficients. In Eqn. 4, $a_1$ is the expansion coefficient associated with the $i^{th}$ basis function, $B_i$.

The choice of basis expansion and hence the choice of a set of basis functions is often dictated by the choice of coordinate system for representation of the general function in question. Characteristics and/or underlying symmetries of the given function can also influence the choice of basis expansion.

For practical purposes of computation in software and/or hardware, the upper limit of the summation in Eqn. 4 has a finite value, N. This upper limit is referred to as the order of the basis expansion. This leads to the following mathematical form for the basis expansion:

$$f(\vec{x}) = \sum_{i=0}^{i=N} a_i B_i(\vec{x}) \quad [\text{Eqn. 5}]$$

and the plurality of expansion coefficients $\{a_1, a_2, a_3, \ldots, a_N\}$ are known as a set of expansion coefficients.

Such an approximation, as in Eqn. 5, necessitates the existence of representation errors because the basis expansion is now of finite order. However, in general, if N is chosen to be sufficiently large, the representation errors will be small for all but the most intransigent of functions. In one embodiment, the order of the expansion is predetermined and is much larger than unity, e.g., N>=30. In another embodiment, the order of the expansion is adaptively determined based on a preliminary quantitative analysis of representation errors for trial values of the expansion order, and may therefore be of different magnitude for different pairs of molecular subsets 410 and 420 based on the characteristics of their respective internal and external volume functions.

In one embodiment, the basis expansion is an orthogonal basis expansion comprising a plurality of mutually orthogonal basis functions. If the basis functions satisfy the following mathematical condition, they are called mutually orthogonal:

$$\int_{\vec{x}} B_i(\vec{x}) B_j(\vec{x}) d\vec{x} = C_{ij} \delta_{ij} \quad [\text{Eqn. 6}]$$

where $C_{ij}$ is a constant (not necessarily unity when i=j), $\delta_{ij}$ is the usual Kronecker delta, and the integral is over the entire M-dimensional space.

For an orthogonal basis expansion, an expansion coefficient, $a_i$, corresponding to a particular basis function, $B_i$, can be written as follows:

$$a_i = \left(\frac{1}{C_{ii}}\right) \int_{\vec{x}} f(\vec{x}) B_i(\vec{x}) d\vec{x} \qquad [\text{Eqn. 7}]$$

where $C_{ii}$ is a constant.

However, once again for the practical purposes of computation, the expansion coefficients are discretized by converting the integral in Eqn. 7 to a finite summation. In the case of a set of expansion coefficients for an orthogonal basis expansion, the discretized expansion coefficient, $a_i$, for an orthonormal basis function, $B_i$, takes the following form:

$$a_i = \left(\frac{1}{C_{ii}}\right) \sum_c f(\vec{x}_c) B_i(\vec{x}_c) \qquad [\text{Eqn. 8}]$$

where the summation is over the discrete points c, i.e., $\vec{x}_c$ is a sample point in the M-dimensional space represented here by $\vec{x}$.

In another embodiment, the basis expansion is an orthonormal basis expansion comprising a plurality of mutually orthonormal basis functions. If the basis functions are mutually orthogonal and in Eqn. 8, $C_{ii}$ is unity for all relevant basis functions, then the basis functions are said to be mutually orthonormal. This similarly simplifies the expressions for $a_i$ in eqns. 7 and 8.

A general 3-D function in spherical polar coordinates can be represented in terms of a radial/spherical harmonics basis expansion comprising a plurality of basis functions, each basis function defined as the product of one of a set of orthonormal radial basis functions, $R_{nl}(r)$, and one of a set of real-valued spherical harmonics basis functions, $y_l^m(\theta,\phi)$, as follows:

$$f(r, \theta, \phi) = \sum_{nlm}^{n=N} a_{nl} R_{nl}(r) y_l^m(\theta, \phi) \qquad [\text{Eqn. 9}]$$

where $\{a_{nlm}\}$ is the set of radial/spherical harmonics expansion coefficients, $(r, \theta, \phi)$ are the spherical coordinates of a point in 3D space, n=[1, N), integer, l=[0, n−1], integer, m=[−1, 1], integer.

The usage of such an expansion is common practice in the quantum mechanical description of numerous atomic and molecular orbitals. Hence the indices n, l, and $|m|\geq 0$ are often respectively referred to as the principal quantum number, angular quantum (or orbital) number and azimuthal (or magnetic moment) quantum number.

In Eqn. 9, each radial basis function, $R_{nl}(r)$, is a 1-D orthonormal basis function depending solely on the radius, r.

The form for the radial basis functions is often chosen based on the problem at hand, e.g., the scaled hydrogen atom radial wave function in quantum mechanics is based for example on associated Laguerre polynomials (Arfken et al.) as follows:

$$R_{nl}(r) = \left[\left(\frac{2}{k^{3/2}}\right) \frac{(n-l-1)!}{\Gamma\left(n+\frac{1}{2}\right)}\right]^{1/2} e^{-\rho/2} \rho^{l/2} L_{n-l-1}^{l+1/2}(\rho) \qquad [\text{Eqn. 10}]$$

where the square root term in the normalization factor, $\rho$ is the scaled distance, $\rho = r^2/k$, k is the scaling parameter, $\Gamma$ is the gamma function, and L( ) are the associated Laguerre polynomials; where a general Laguerre polynomial is a solution to the Laguerre differential equation given by:

$$xy'' + (1-x)y' + \lambda y = 0 \qquad [\text{Eqn. 11}]$$

and the associated Laguerre polynomials themselves are given explicitly by Rodrigue's formula as follows:

$$L_n^k(x) = \sum_{m=0}^n (-1)^m \frac{(n+k)!}{(n-m)!(k+m)!m!} x^m, \qquad [\text{Eqn. 12}]$$

$$L_n^k(x) = \sum_{m=0}^n \left((-1)^m \frac{(n+k)!}{(n-m)!(k+m)!m!} x^m\right),$$

Various radial basis functions can be used in accordance with embodiments of the present invention. In one embodiment, the radial basis functions include the scaled Laguerre polynomial-based functions of Eqn. 10. In another embodiment, the radial basis functions include unscaled forms of Eqn. 10 in terms of r (not $\rho$) and without the normalization constants. In yet another embodiment the radial basis functions include a Bessel function of the first kind ($J_n(r)$). In yet another embodiment the radial basis functions include a Hermite polynomial function ($H_n(r)$). In other embodiments, the radial basis functions include any mutually orthonormal set of basis functions that depend on the radius in a spherical coordinate system centered on the respective molecular center of the molecular subset in question.

In Eqn. 9, each real-valued spherical harmonic basis function, $y_l^m(\theta,\phi)$, is a 2-D orthonormal basis function depending on the angular variables $(\theta, \phi)$ of a spherical coordinate system centered on the molecular center of the each molecular subset. Spherical harmonics satisfy a spherical harmonic differential equation, representing the angular part of the Laplace's equation in spherical coordinate system:

$$\frac{\Phi(\phi)}{\sin\theta} \frac{d}{d\theta}\left(\sin\theta \frac{d\Theta}{d\theta}\right) + \frac{\Theta(\theta)}{\sin^2\theta} \frac{d^2\Phi(\phi)}{d\phi^2} + l(l+1)\Theta(\theta)\Phi(\phi) = 0. \qquad [\text{Eqn. 13}]$$

The spherical harmonics themselves are complex-valued, separable functions of $\theta$ and $\phi$, and are given in terms of an associated Legendre polynomial, $P_l^m(x)$, by the equation, $$Y_l^m(\theta, \phi) \equiv \sqrt{\frac{2l+1}{4\pi} \frac{(l-m)!}{(l+m)!}} P_l^m(\cos\theta) e^{im\phi}, \qquad [\text{Eqn. 14}]$$

where the associated Legendre polynomial is given by:

$$P_l^m(x) = \frac{(-1)^m}{2^l l!} (1-x^2)^{m/2} \frac{d^{l+m}}{dx^{l+m}} (x^2-1)^l \qquad [\text{Eqn. 15}]$$

Figure 12:
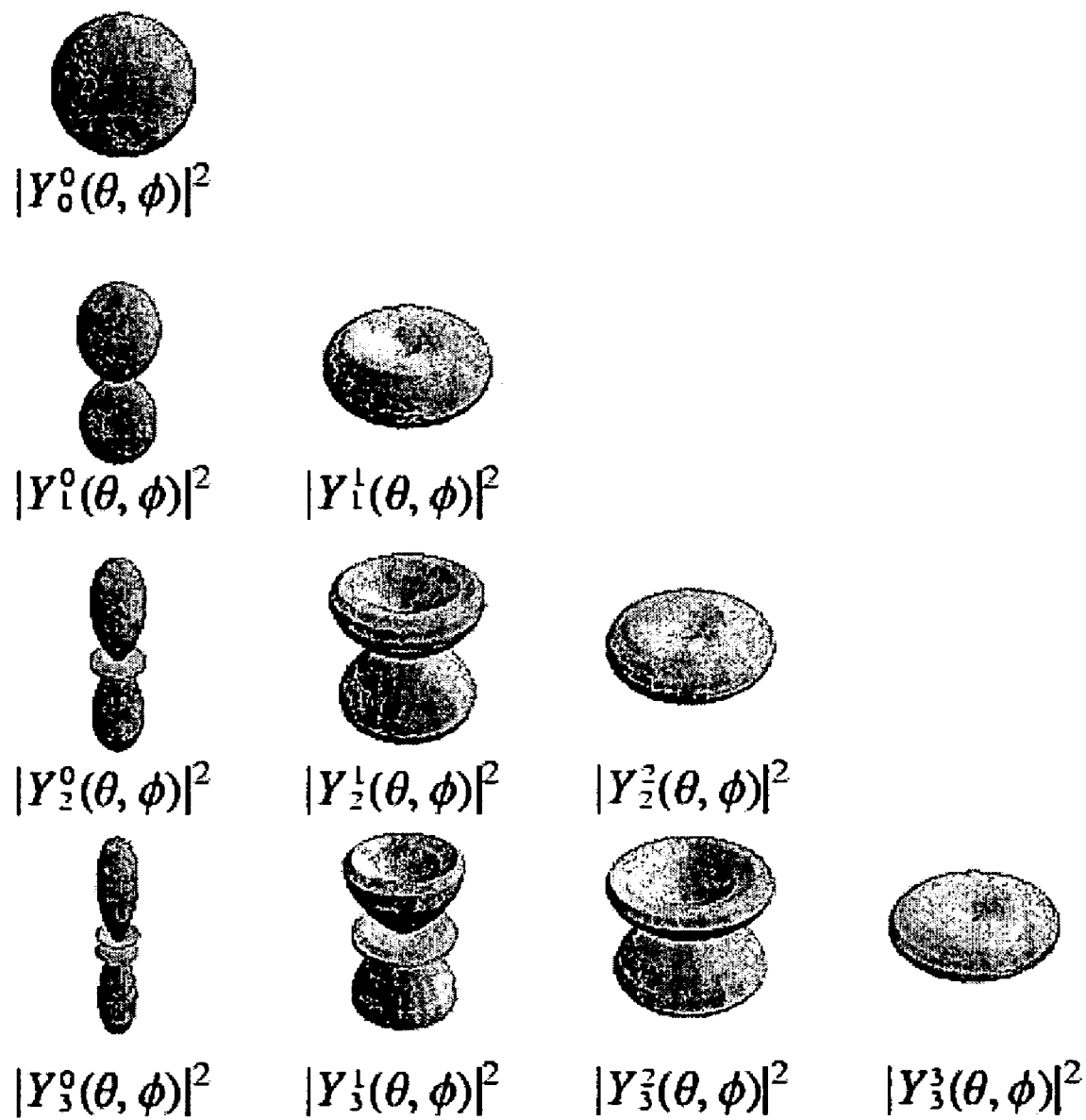
FIG. 12 is an illustration of spherical harmonics functions.

Spherical harmonics can be used to represent 3-D molecular shapes in the context of molecular docking, as described in Ritchie et al. An illustration of the first few spherical harmonics is shown in FIG. 12, in terms of their amplitudes. The depicted spherical harmonics surfaces are excerpted from web pages available at Eric Weisstein's World of Mathematics on the worldwide web at http://mathworld.wolfram.com/.

Real-valued spherical harmonics functions, $y_l^m(\theta,\phi)$, can be obtained from suitable linear combinations of $Y_l^m$ and its complex conjugate $Y*_l^m$ in order to represent the real and imaginary parts of $Y_l^m$, as follows:

$$y_l^m(\theta, \phi) = \begin{cases} (Y_l^m(\theta, \phi) + Y_l^m(\theta, \phi)^*)/\sqrt{2} & m > 0 \\ (Y_l^0(\theta, \varphi)) & m = 0 \\ -i(Y_l^m(\theta, \phi) - Y_l^m(\theta, \phi)^*)/\sqrt{2} & m < 0 \end{cases} \quad \text{[Eqn. 16]}$$

Based on Eqn. 9, the expansion coefficients $\{a_{nlm}\}$ coefficients for an arbitrary 3-D volume function $f(r, \theta, \phi)$ are defined as:

$$a_{nlm} = \int f(r,\theta,\phi) R_{nl}(r) y_l^m(r,\theta,\phi) dV \quad \text{[Eqn. 17]}$$

where the integral is over the extent of function $f(r, \theta, \phi)$ in spherical coordinates and $dV$ is a differential volume element in spherical coordinates.

The discretized analog of the expansion coefficients in Eqn. 17 are given by:

$$a_{nlm} = \sum_c f(r_c, \theta_c, \varphi_c) R_{nl}(r_c) y_l^m(r, \theta) \Delta V_c \quad \text{[Eqn. 18]}$$

where the summation is over all grid cells, c, and $(r_c, \theta_c, \phi_c)$ are the spherical coordinates of the center of grid cell c and $\Delta V_c$ is the volume of grid cell c.

In one embodiment of the present invention, the grid cells in Eqn. 18 are cuboids from a Cartesian coordinate system and the spherical 3-tuples $(r_c, \theta_c, \phi_c)$ are converted 'on-the-fly' to Cartesian 3-tuples $(x_c, y_c, z_c)$ by means of a suitable coordinate transformation, for easy addressing of the function, f, over a lattice representation stored in a computer readable memory. In another embodiment the grid cells can be a varying volume, $\Delta V_c$. In yet another embodiment the grid cells represent small volumes in a spherical coordinate system. In yet another embodiment the grid cells represent small volumes in a cylindrical coordinate system.

Eqn. 18 has been used to represent volumetric functions describing the shape of a molecular subset by a corresponding set of expansion coefficients as described in Ritchie et al. In one embodiment of the present invention, in step 316 of FIG. 3, Eqn. 18 is used to represent the coordinate based representation of the internal volume function of the first molecular subset 410, $\tau_a$, in terms of a set of expansion coefficients for an initial pose of molecular subset 410, herein designated as a reference set of expansion coefficients. Similarly, the coordinate based representation of the external volume function of the first molecular subset 410, $\sigma_a$, is represented in terms of a set of expansion coefficients for the same initial pose of molecular subset 410, also designated as a reference set of expansion coefficients but now for the external volume function, $\sigma_a$. In another embodiment, $f(r_c, \theta_c, \phi_c)=1$ if the grid cell is occupied, i.e., "lies within" (see above) the nonzero domain of the volume function in question, and zero otherwise.

Similarly, reference sets of expansion coefficients can be constructed for the internal and external volume functions of molecular subset 420 (respectively $\tau_b$ and $\sigma_b$) for an initial pose of molecular subset 420. Thus altogether there are four sets of reference expansion coefficients computed for the two molecular subsets 410 and 420, each corresponding to a volume function for one of the molecular subsets. The coefficient sets for molecular subset 410 are designated as $\{a^\sigma_{nlm}\}$ and $\{a^\tau_{nlm}\}$, respectively, and the coefficient sets for molecular subset 420 are designated as $\{b^\sigma_{nlm}\}$ and $\{b^\tau_{nlm}\}$ respectively. In another embodiment, the four reference sets of expansion coefficients are computed using Eqn. 8 where the set of basis functions $\{B_i\}$ correspond to a general basis expansion, i.e., need not be the radial/spherical harmonics expansion of Eqn. 9, upon which Eqn. 18 is predicated.

In one embodiment of the present invention, the set of values comprising $\{f(r_c, \theta_c, \phi_c)\}$ for all grid cells c (both occupied and unoccupied) in a coordinate based representation for the internal volume function of molecular subset 410 are converted to a stream or an array of Cartesian-based values $\{f(x_c, y_c, z_c)\}$ via a suitable coordinate transformation and stored on a computer readable and recordable medium for future retrieval. Later, when the stored values are to be used in the context of Eqn. 18 to compute expansion coefficients, the stored values are first retrieved and then converted back into $\{f(r_c, \theta_c, \phi_c)\}$ by an inverse coordinate transformation.

In the case that $f(r_c, \theta_c, \phi_c)$ is unity for occupied grid cells and zero otherwise, the stored set of values $\{f(x_c, y_c, z_c)\}$ become a bit stream or a bitmap. Similarly the values corresponding to coordinate based representations for the external volume function of molecular subset 410 can be stored and retrieved in a similar manner. The same also applies to the values corresponding to coordinate based representations for the internal and external volume functions of molecular subset 420.

In FIG. 3, in step 318, the method continues with providing a translation operator representing translation of the coordinate based representation 810 of the first molecular subset with respect to the coordinate based representation 820 of the second molecular subset in the joint coordinate system. The term "translation operator" refers to an operator that, when applied to a point, results in the point's translation along a vector as defined by the translation operator. The operator can be applied to any collections of points as a subset of 3-D space, e.g., a line, a curve, a surface, or a volume.

In one embodiment, the translation operator is a matrix function of the displacement along the intermolecular axis 870 between the first and second molecular subsets. Then the translation operator can be directly applied to the set of reference expansion coefficients for the internal and external volume functions of molecular subset 410, while leaving molecular subset 420 untouched. In another embodiment, molecular subset 410 is held fixed and the translation operator is directly applied to the set of reference expansion coefficients for the internal and external volume functions of molecular subset 420.

In one embodiment, using the joint $(R,\beta_1,\gamma_1,\alpha_2,\beta_2,\gamma_2)$ coordinate system of FIG. 8, in conjunction with the radial/spherical harmonics expansion of Eqn. 9, the translation operator representing the translation of the coordinate based representation of the internal volume function for molecular subset 410 from R=0 (meaning molecular centers of molecular subsets 410 and 420 are same point in FIG. 8) to R>0 is directly applied to the reference set of expansion coefficients $\{a^{\tau,\sigma}_{nlm}\}$ for the internal and external volume functions for molecular subset 410 according to the following rule:

$$\tilde{a}^{\tau,\sigma}_{nlm}(R) = \sum_{n'l'} a^{\tau,\sigma}_{n'l'm'} K_{nn'll'|m|}(R) \delta_{mm'} \quad \text{where } \{\tilde{a}^{\tau,\sigma}_{nlm}\} \quad \text{[Eqn. 19]}$$

are the new translated set of expansion coefficients, (n, l, m) are quantum numbers for the new translated expansion coefficient, (n', l', m') are quantum numbers for the one of the set of reference expansion coefficients, the summation is over all possible values of n' and l', $\delta_{mm'}$ is the standard Kronecker delta, and $K_{nn'll'|m|}$ are matrix elements of a translation matrix function with values equal to resultant overlap integrals between two different basis functions of the radial/spherical harmonics expansion, with quantum numbers n, l, m and n', l', m' respectively, separated by a distance R, and which are nonzero only when m=m'.

The exact form for the translation matrix $K_{nn'll'|m|}$ depends on the choice of radial basis functions used in Eqn. 9. Eqn. 19 has been used previously to efficiently derive a new set of translated expansion coefficients from a reference set of expansion coefficients as described in Danos, M., and Maximon, L. C., "Multipole matrix elements of the translation operator", J. Math. Phys., 6(1), 766-778, 1965; Talman, J. D., "Special Functions: A Group Theoretical Approach", W. A. Benjamin Inc., New York, 1968; all of which are hereby incorporated by reference in their entirety.

In one embodiment, the entire set of translation matrix elements, $K_{nn'll'|m|}$, may be pre-computed for all relevant values of n, n', l, l', & m for a finite order of expansion, N, and stored on a computer readable and recordable medium for future retrieval as needed. This is advantageous since calculation of the overlap integrals which define each translation matrix element can be very costly and yet for a given finite order of expansion and a given form for the radial basis functions used in Eqn. 8, the calculations need to be done only once and the resultant K-matrix is applicable to any molecular subset regardless of size and shape. Moreover, for the large values of N, the number of translation matrix elements is $O(N^5)$.

In FIG. 3, in step 320, the method continues with providing a first rotation operator representing rotation (change of orientation) of the coordinate based representation 810 of the internal and external volume functions for the first molecular subset 410 with respect to the Cartesian frame 830 co-located with the molecular center 850 of molecular subset 410 in the joint coordinate system.

The term "rotation operator" generally refers to an operator that, when applied to a point, results in the point's rotation about an axis as defined by the rotation operator. The operator can be applied to any collections of points, e.g., a line, a curve, a surface, or a volume. As described with regards to Eqn. 3, any rotation in 3-D can be represented by a set of three Euler angles.

In one embodiment, different orientations of the coordinate based representation 810 of the internal and external volume functions for the first molecular subset 410 with respect to the Cartesian frame 830 are generally represented by a set of three Euler angles representing roll ($\alpha_1$), pitch ($\beta_1$), and yaw ($\gamma_1$), as shown in FIG. 8. In another embodiment the roll angle ($\alpha_1$), describing rotation with respect to the z-axis of the Cartesian frame 830, is ignored since with respect to the common z-axis of the joint coordinate system only the relative orientation between the two molecular subsets is relevant. Then the orientation of molecular subset 410 with respect to Cartesian frame 830 is fully described by a pair of Euler angles ($\beta_1, \gamma_1$). In another embodiment the angles need not be Euler angles and in fact depend on the choice of joint coordinate system.

In one embodiment, the first rotation operator is a matrix function of ($\alpha_1, \beta_1, \gamma_1$). Then the first rotation operator can be directly applied to the set of reference expansion coefficients for the internal and external volume functions of molecular subset 410. In one embodiment, using the joint (R, $\beta_1, \gamma_1, \alpha_2, \beta_2, \gamma_2$) coordinate system of FIG. 8, in conjunction with the radial/spherical harmonics expansion of Eqn. 9, the first rotation operator representing the rotation of the coordinate based representation of the internal and external volume functions for molecular subset 410 from ($\alpha_1=0, \beta_1=0, \gamma_1=0$) to arbitrary ($\alpha_1, \beta_1, \gamma_1$) is directly applied to the reference set of expansion coefficients $$\{a_{nlm}^{\tau,\sigma}\}$$

for the internal and external volume functions for molecular subset 410 according to the following rule:

$$\hat{a}_{nlm}^{\tau,\sigma} = \sum_{m'=-l}^{m'=+l} a_{nlm'}^{\tau,\sigma} R_{mm'}^l(\alpha_1, \beta_1, \gamma_1) \text{ where } \{\hat{a}_{nlm}^{\tau,\sigma}\} \quad \text{[Eqn. 20]}$$

are the new rotated set of expansion coefficients, (n, l, m) are the quantum numbers for the new rotated expansion coefficient, m' denotes the magnetic moment quantum number for one of the set of reference expansion coefficients, $$\{a_{nlm}^{\tau,\sigma}\},$$

the summation is over all possible values of m', and $R^1_{mm'}$ are matrix elements of a block diagonal matrix such that each $R^{(1)}$ denotes a $(2l+1)*(2l+1)$ block sub matrix. This property that the harmonic expansion coefficients transform amongst themselves under rotation in a similar way in which rotations transform the (x, y, z) coordinates in Cartesian frame was first presented in the context of molecular shapes by Leicester, S. E., Finney, J. L., and Bywater, R. P., in "A Quantitative Representation of Molecular-Surface Shape. 1. Theory and Development of the Method", (1994), J. Mathematical Chemistry, 16(3-4), 315-341; all of which is hereby incorporated by reference in its entirety.

For an arbitrary Euler rotation with angles ($\alpha, \beta, \gamma$) and for a pair of positive magnetic moment quantum numbers, m and m', the individual matrix elements are computable in terms of Wigner rotation matrix elements, $d^1_{mm'}(\beta)$, as follows:

$$R^1_{mm'}(\alpha,\beta,\gamma)=d^1_{mm'}(\beta)\cos(m'\gamma+ma)+(-1)^m d^1_{mm'}(\beta)\cos(m'\gamma+ma) \quad \text{[Eqn. 21]}$$

where $d^1_{mm'}(\beta)$, the elements of the Wigner rotation matrix are given by:

$$d^l_{mm'}(\beta) = \sum_{k=k_1}^{k_2} (-1)^{k+m'-m} C(l, m, k) \quad \text{[Eqn. 22]}$$

$$\left(\cos\frac{\beta}{2}\right)^{2l+m-m'-2k} \left(\sin\frac{\beta}{2}\right)^{2k+m'-m}$$

with $k_1$=max (0, m-m'), $k_2$=min(1-m', 1+m), and C(1,m,k) being a constant function. Similar forms exist for the other eight possible signed pairs of m and m'. For further details on Wigner matrix elements, refer to Su, Z., and Coppens, P., J.

Applied Crystallography, 27, 89-91(1994); all of which is hereby incorporated by reference in their entirety. In one embodiment, where ($\alpha_1$=0) for all rotations of molecular subset 410, Eqn. 21 simplifies and the $R^1_{mm'}$ matrix elements are functions of ($\beta_1,\gamma_1$) alone.

For basis expansions other than the radial/spherical harmonics expansion of Eqn. 9, eqns. 20 and 21 will be replaced by appropriate analogs depending on the choice of angular basis functions, with suitable indices representing each basis function.

In FIG. 3, also in step 320, the method continues with providing a second rotation operator representing rotation of the coordinate based representation 820 of the internal and external volume functions for the second molecular subset 420 with respect to the Cartesian frame 840 co-located with the molecular center 860 of molecular subset 420 in the joint coordinate system. As with the first molecular subset 410, different orientations of the coordinate based representation 820 of the internal and external volume functions for the second molecular subset 420 with respect to the Cartesian frame 840 are generally represented by a set of three Euler angles representing roll ($\alpha_2$), pitch ($\beta_2$), and yaw ($\gamma_2$), as shown in FIG. 8. In another embodiment the angles need not be Euler angles and in fact depend on the choice of joint coordinate system.

In one embodiment, the second rotation operator is a matrix function of ($\alpha_2$, $\beta_2$, $\gamma_2$). Then the second rotation operator can be directly applied to the set of reference expansion coefficients for the internal and external volume functions of molecular subset 420 in a manner similar to the application of the first rotation operator to the set of reference expansion coefficients for the internal and external volume functions of molecular subset 410.

In one embodiment, the matrix function representing the second rotation operator can be split up into two distinct rotation operators, the first being a function of ($\beta_2$, $\gamma_2$) alone (i.e., $\alpha_2$=0) and the second being a function of the roll Euler angle, $\alpha_2$, alone (i.e., ($\beta_2$=0, $\gamma_2$=0)). Thus either of these two rotation operators can be applied first to the reference set of expansion coefficients in order to obtain an intermediate rotated set of coefficients and the remaining operator then applied in succession in order to generate a final resultant set of rotated coefficients. In such an embodiment, the two rotation operators are designated as the second and third rotation operators in order to avoid confusion regarding the first rotation operator for molecular subset 410. Moreover, in this embodiment, when in conjunction with the radial/spherical harmonics expansion of eqns. 9, 20, and 21 can be applied for determining the result of application of each rotation operator to the second molecular subset 420, in which case the application of the third rotation operator reduces to simple multiplication by constants and sines and cosines of the quantity (m'$\alpha$).

In another embodiment, similar to the work of Ritchie et al, the simplified form for the third rotation operator permits direct application of the third rotation operator to computed shape complementarity scores themselves, as described below, as opposed to intermediate rotated expansion coefficients for the volume functions associated with the second molecular subset 420.

In FIG. 3, in step 322, after the translation operators are defined, sets of translated expansion coefficients are constructed for the first molecular subset 410 from the sets of reference expansion coefficients for the internal and external volume functions of molecular subset 410. The term "translated expansion coefficients" generally refers to a set of expansion coefficients obtained by applying a translation operator to another set of expansion coefficients.

As discussed above, step 310 provides for an axial sampling scheme comprised of axial sample points which delimit the allowed values of the intermolecular separation, R, in FIG. 8 as applied to the relative translation of the two molecular subsets. In order to account for all allowed relative translations of the two molecular subsets, it is necessary to compute a set of translated expansion coefficients for both the internal and external volume functions of the first molecular subset 410, $$\{\tilde{a}^{\tau,\sigma}_{nlm}(R=R_i)\},$$

corresponding to each distinct axial sample point, $R_i$, in the axial sampling scheme.

As discussed above, this is accomplished via direct application of a translation operator in the form of a matrix multiplication to the reference sets of expansion coefficients for the first molecular subset 410, $$\{a^{\tau,\sigma}_{nlm}(R=0)\}.$$

In one embodiment, where the radial/spherical harmonics expansion of Eqn. 9 is utilized, Eqn. 19 governs the construction of $$\{\tilde{a}^{\tau,\sigma}_{nlm}(R=R_i)\}$$

for all axial sample points. Any and all permutations of the order in which axial sample points are visited is permitted, so long as in the end the construction is completed for all axial sample points.

In another embodiment, molecular subset 410 is held fixed, and the translation operator is directly applied instead to the reference sets of expansion coefficients for the internal and external volume functions of the second molecular subset 420, $$\{b^{\tau,\sigma}_{nlm}(R=0)\}.$$

Since only relative translation of the two molecular subsets in meaningful, it is necessary to apply the translation operator to the coordinate based representations for $\tau$ and $\sigma$ for only one of the two molecular subsets.

In FIG. 3, in step 324, after the rotation operators are defined, sets of rotated expansion coefficients are constructed for the second molecular subset 420 from the sets of reference expansion coefficients for the internal and external volume functions of molecular subset 420. The term "rotated expansion coefficients" generally refers to a set of expansion coefficients obtained by applying a rotation operator to another set of expansion coefficients. As discussed above, step 312 provides for a second spherical sampling scheme comprised of spherical sample points which delimit the allowed values of the pitch and yaw Euler angles, ($\beta_2$, $\gamma_2$), in FIG. 8 as applied to orientation of the second molecular subset 420. Also as discussed above, step 314 provides for an angular sampling scheme comprised of angular sample points which delimit the allowed values of the roll Euler angle, $\alpha_2$, in FIG. 8 as applied to rotation of the second molecular subset 420 with respect to the joint z-axis.

In order to account for all allowed orientations of the second molecular subset 420, it is necessary to compute a set of rotated expansion coefficients for both the internal and external volume functions of the second molecular subset 420, $$\{\hat{b}_{lmn}^{\tau,\sigma}(\alpha_2 = \alpha_{2i}, \beta_2 = \beta_{2j}, \gamma_2 = \gamma_{2k})\},$$

corresponding to each distinct angular sample point, $\alpha_{2i}$, in the angular sampling scheme and each distinct spherical sample point, $(\beta_{2j}, \gamma_{2k})$, in the second spherical sampling scheme, i.e., $(\alpha_{2i}, \beta_{2j}, \gamma_{2k}) \in$ Cartesian product of the angular sampling scheme and the second spherical sampling scheme.

As discussed above, this computation is accomplished via direct application of a rotation operator in the form of a matrix multiplication to the reference sets of expansion coefficients for the second molecular subset 420, $$\{b_{nlm}^{\tau,\sigma}\}.$$

In one embodiment, where the radial/spherical harmonics expansion of Eqn. 9 is utilized, Eqn. 20 governs the construction of $$\{\hat{b}_{lmn}^{\tau,\sigma}(\alpha_2 = \alpha_{2i}, \beta_2 = \beta_{2j}, \gamma_2 = \gamma_{2k})\}$$

for all $(\alpha_{2i}, \beta_{2j}, \gamma_{2k}) \in$ Cartesian product of the angular sampling scheme and the second spherical sampling scheme. Any and all permutations of the order in which the orientations $(\alpha_{2i}, \beta_{2j}, \gamma_{2k})$ are visited is permitted, so long as in the end the construction is completed for all permitted $(\alpha_{2i}, \beta_{2j}, \gamma_{2k})$. Also as discussed above, in one embodiment the construction can be accomplished by two distinct rotational operators, the first a function of the pitch and yaw Euler angles, $(\beta_2, \gamma_2)$, and the second a function solely of the roll Euler angle, $\alpha_2$. Moreover, in another embodiment, similar to the work of Ritchie et al, the latter operator (designated previously as the "third rotation operator") can be deferred until generation of shape complementarity scores, as described below.

In FIG. 3, in step 326, sets of transformed expansion coefficients are constructed for the first molecular subset 410 from the sets of translated expansion coefficients generated in FIG. 3, step 322, for the internal and external volume functions of molecular subset 410. The term "transformed expansion coefficients" generally refers to a set of expansion coefficients obtained by applying an operator representing an arbitrary linear transformation on another set of expansion coefficients. This linear transformation may be the composition of one or more translation and/or rotation operators.

As discussed above, step 312 provides for a first spherical sampling scheme comprised of spherical sample points which delimit the allowed values of the pitch and yaw Euler angles, $(\beta_1, \gamma_1)$, in FIG. 8 as applied to orientation of the first molecular subset 410. As discussed above, each set of translated expansion coefficients corresponds to an axial sample point of an axial sampling scheme which delimits the allowed values of the intermolecular separation, R, in FIG. 8 as applied to the relative translation of the two molecular subsets. In order to account for all allowed configurations (both relative orientations and translations) of the first molecular subset 410 relative to the second, it is necessary to compute a set of transformed expansion coefficients for both the internal and external volume functions of the first molecular subset 410, $$\{\ddot{a}_{nlm}^{\tau,\sigma}(R = R_i, \alpha_1 = 0, \beta_1 = \beta_{1j}, \gamma_1 = \gamma_{1k})\},$$

corresponding to each distinct axial sample point, $R_i$, in the axial sampling scheme and each distinct spherical sample point, $(\beta_{1j}, \gamma_{1k})$, in the first spherical sampling scheme, i.e., $(R_i, \alpha_1=0, \beta_{1j}, \gamma_{1k}) \in$ Cartesian product of the axial sampling scheme and the first spherical sampling scheme.

As discussed above, this computation is accomplished via direct application of a first rotation operator in the form of a matrix multiplication to the translated sets of expansion coefficients of step 318 for the first molecular subset 410, $$\{\tilde{a}_{nlm}^{\tau,\sigma}(R = R_i)\}.$$

In one embodiment, where the radial/spherical harmonics expansion of Eqn. 9 is utilized, a variant of Eqn. 20 governs the construction of $$\{\ddot{a}_{nlm}^{\tau,\sigma}(R = R_i, \alpha_1 = 0, \beta_1 = \beta_{1j}, \gamma_1 = \gamma_{1k})\}$$

in terms of $$\{\tilde{a}_{nlm}^{\tau,\sigma}(R = R_i)\}$$

for all $(R_i, \alpha_1=0, \beta_{1j}, \gamma_{1k}) \in$ Cartesian product of the axial sampling scheme and the first spherical sampling scheme. Any and all permutations of the order in which $(R_i, \alpha_1=0, \beta_{1j}, \gamma_{1k})$ are visited are permitted, so long as in the end the construction is completed for all permitted $(R_i, \alpha_1=0, \beta_{1j}, \gamma_{1k})$.

Due to commutativity, the transformed coefficients for the first molecular subset 410 can be generated by the application of the first rotation operator and the translation operator in any order. Operations are "commutative" if the order in which they are done does not affect the results of the operations. The first rotation operator commutes with the translation operator, so it is possible to have instead applied the first rotation operator to the set of reference expansion coefficients, in order to generate sets of rotated coefficients for the internal and external volume functions for the first molecular subset 410, in a manner similar to step 320 for the second molecular subset 420.

However, as will be discussed below in regards to the generation of shape complementarity scores, it is far more efficient in terms of computations (and potential storage) to generate sets of translated coefficients for one axial sample point at a time and to then subsequently apply the first rotation operator in order to generate the sets of transformed coefficients for the first molecular subset 410.

In FIG. 3, in step 328, a shape complementarity score is defined. The shape complementarity score represents a correlation between the internal volume function of the first molecular subset 410 with the external volume function of the second molecular subset 420, and a correlation between the internal volume function of the second molecular subset 420 with the external volume function of the first molecular subset 410. This correlation represents the shape complementarity of the first and second molecular subsets for one relative position and orientation of the coordinate based representations of the first and second molecular subsets in the joint coordinate system. The shape complementarity score is computed in terms of the set of transformed expansion coefficients for the first molecular subset and the set of rotated (also referred to as "transformed") expansion coefficients for the second molecular subset, corresponding to a position and orientation of the first molecular subset and to a position and orientation of the second molecular subset.

In one embodiment, the shape complementarity score, S, is defined, in a manner similar to that used in Ritchie et al, as follows:

$$S = \int \sigma_a \tau_b dV + \int \sigma_b \tau_a dV - \lambda \int \tau_a \tau_b dV \quad \text{[Eqn. 23]}$$

where $(\sigma_a, \tau_a)$ respectively refer to the external and internal volume functions of molecular subset 410, $(\sigma_b, \tau_b)$ respectively refer to the external and internal volume functions of molecular subset 420, $-\lambda \geq 0$ is a constant, and the integrals over all 3-D space.

The shape complementarity score of Eqn. 23 is based on assigning a positive value to the favorable overlap of the first external volume function and the second internal volume function, and a positive value to the favorable overlap of the first internal volume function and the second external volume function, and a negative value to the unfavorable overlap of the first and second internal volume functions, in the spirit of the Pauli Exclusion Principle. Hence, the constant $-\lambda$ in Eqn. 23 can be considered a penalty constant that weighs the third integral relative to the first two.

Figure 13:
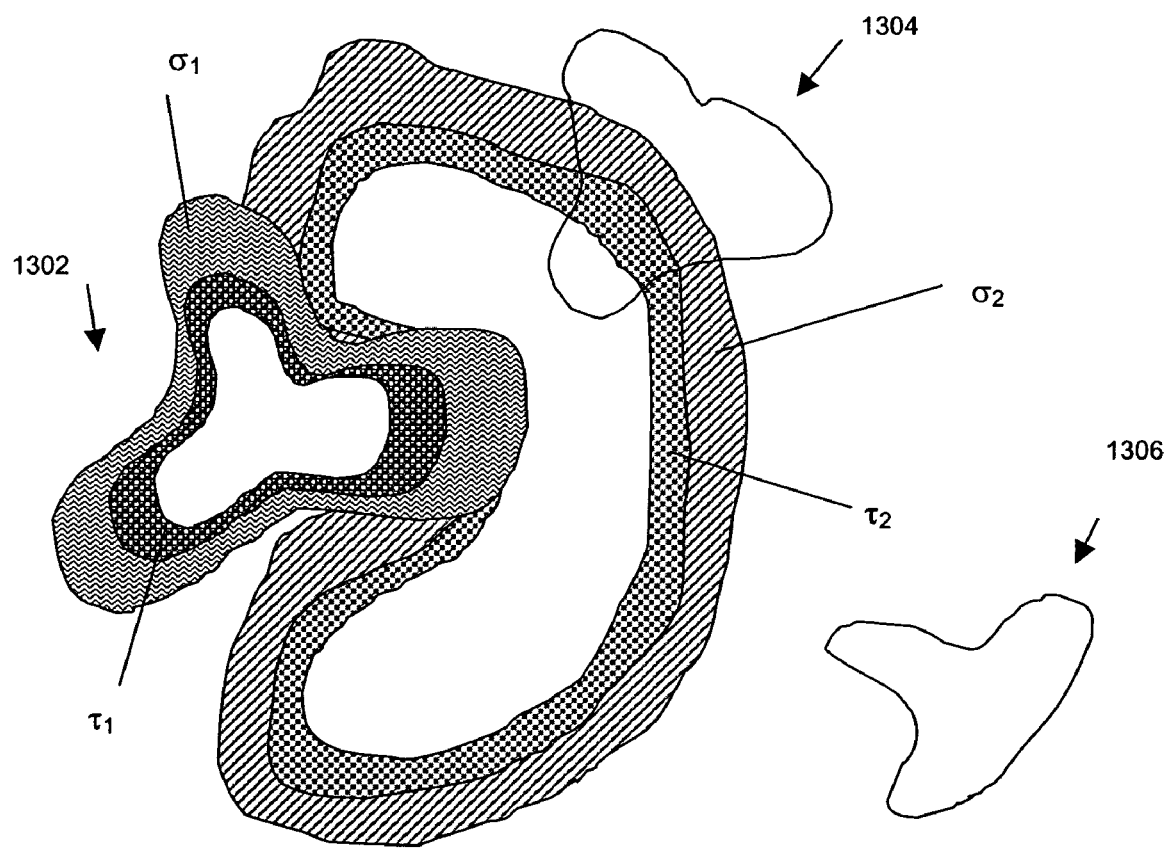
FIG. 13 shows two molecular subsets in various configurations, i.e., having various relative translations and orientations to one another, for computing shape complementarity scores, in accordance with embodiments of the present invention.

Shape complementarity scores are computed for different relative positions and orientations of the first and second molecular subsets 410 and 420, shown in FIG. 13 In this embodiment, as shown in FIG. 13 a high score is generated for a configuration when the external volume function of the first molecular subset $(\sigma_1)$ overlaps with the internal volume function of the second molecular subset $(\tau_2)$ and vice-versa, such as when the molecular subsets are oriented and positioned as indicated by reference numeral 1302, thus representing a more optimal fit. Lower scores are generally calculated for configurations when there is little or no overlap, as indicated by reference numeral 1306. Lower scores, and sometimes even negative scores, are generated for configurations when the internal volume function of the first molecular subset $(\tau_1)$ significantly overlaps with the internal volume function of the second molecular subset $(\tau_2)$ as indicated by reference numeral 1304.

In FIG. 3, in step 328, a plurality of shape complementarity scores are generated by iterating over the set of sampled configurations for the molecular combination, where the set of sampled configurations is the Cartesian product of the set of sampled poses for the first molecular subset and the set of sampled poses for the second molecular subset. The iteration over the set of sampled configurations for the molecular combination, for the purpose of generating the plurality of shape complementarity scores, can be performed in any order.

High correlations are achieved when the internal volume of the first molecular subset overlaps highly with the external volume of the second molecular subset and vice-versa. Low correlations result when there is little or no overlap between the volume functions from different molecular subsets or when significant overlap between two internal volume functions, representing unfavorable atomic overlaps.

In one embodiment, the optimal fit (for example the predicted binding mode) is generally decided based on the particular configuration, i.e., relative position and orientation, that yields the highest shape complementarity score. In another embodiment, the magnitude of the best score, or the top x % of scores, determines the results of the analysis of the molecular combination of the two molecular subsets. In another embodiment, all shape complementarity scores below a preset numerical threshold are rejected, and only those configurations with passing scores are retained for further analysis. In yet another embodiment, the shape complementarity scores are filtered based on an adaptive threshold dependent on observed statistics of the scores as they are generated. In yet another embodiment, the statistical analysis of both passing score magnitudes, as well as multidimensional clustering of the relative position and orientation coordinates of passing configurations, is used to predict the binding mode and/or assess the nature and likelihood of the molecular combination.

In yet another embodiment, the above strategies can be used when screening a collection of second molecular subsets against the same first molecular subset 410 in order to predict potential binding modes and estimate binding affinity based on computations of shape complementarity, in order to select promising candidates for further downstream processing in the drug discovery pipeline.

In one embodiment, the plurality of shape complementarity scores is calculated at one value for the order of the expansion, $N_1$, and then the results are quantitatively analyzed according to certain decision criteria. In another embodiment, the decision criteria are based on a cluster analysis of the shape complementarity scores. As used herein, the term "cluster analysis" generally refers to a multivariate analysis technique that seeks to organize information about variables so that relatively homogeneous groups, or "clusters," can be formed. The clusters formed with this family of methods should be highly, internally homogenous (members from same cluster are similar to one another) and highly, externally heterogeneous (members of each cluster are not like members of other clusters).

A further plurality of shape complementarity scores may then be calculated at a higher value for the order of the expansion, $N_2 > N_1$, based on results of the quantitative analysis. The shape complementarity scores may be computed at the higher expansion order, $N_2$, only at those sample points for which the corresponding shape complementarity score computed at the lower expansion order, $N_1$, satisfies the decision criteria imposed by the aforementioned quantitative analysis.

Generally, it is inefficient to directly evaluate Eqn. 23 in its integral form. By first applying a basis expansion to the coordinate based representations of the internal and external volume functions of the two molecular subsets to obtain reference sets of expansion coefficients and then using appropriate translation and rotation operators to generate sets of transformed expansion coefficients for the first molecular subset 410 corresponding to the sampled poses of the first molecular subset, and to likewise generate sets of transformed expansion coefficients for the second molecular subset 420 corresponding to the sampled poses of the second molecular subset, the shape complementarity score for a given configuration of the molecular combination can be computed efficiently and to arbitrary precision based on the magnitude of N, the order of the expansion.

In one embodiment, within the context of the joint coordinate system of FIG. 8 and using the radial/spherical harmonics expansion of Eqn. 9, and eqns. 18, 19, and 20 to construct and transform reference sets of expansions coefficients for the coordinate based representations of both the internal and external volume functions for both molecular subsets 410 and 420, Eqn. 23 can be rewritten as follows:

$$S(R, \beta_1, \gamma_1, \alpha_2, \beta_2, \gamma_2) = \sum_{nlm}^{N} \left( \ddot{a}_{nlm}^{\sigma} \hat{b}_{nlm}^{\tau} + \ddot{a}_{nlm}^{\tau} \hat{b}_{nlm}^{\lambda} \right) \quad \text{[Eqn. 24]}$$

where $\hat{b}_{nlm}{}^{\lambda} = \hat{b}_{nlm}{}^{\sigma} - \lambda \hat{b}_{nlm}{}^{\tau}$, the transformed expansion coefficients for the first molecular subset are evaluated at the sample point $$\{\ddot{a}_{nlm}^{\tau,\sigma}(R = R_i, \alpha_1 = 0, \beta_1 = \beta_{1j}, \gamma_1 = \gamma_{1k})\},$$

and the rotated expansion coefficients for the second molecular subset are evaluated at the sample point $$\{\hat{b}_{lmn}^{\tau,\sigma}(\alpha_2 = \alpha_{2i}, \beta_2 = \beta_{2j}, \gamma_2 = \gamma_{2k})\}.$$

In the embodiment where the third rotation operator is directly applied to the computed shape complementarity scores themselves, the score is computed in two steps. In the first step, two intermediate factors $\Lambda_m^+$ and $\Lambda_m^-$ are computed, $$\Lambda_m^+ = \sum_{nlm}^{N} \left( \ddot{a}_{nlm}^{\sigma} \hat{b}_{nlm}^{\tau} + \ddot{a}_{nlm}^{\tau} \hat{b}_{nlm}^{\lambda} \right) \quad \text{[Eqn. 25]}$$

$$\Lambda_m^- = \sum_{nlm}^{N} \left( \ddot{a}_{nlm}^{\sigma} \hat{b}_{nlm}^{\tau} + \ddot{a}_{nlm}^{\tau} \hat{b}_{nlm}^{\lambda} \right)$$

where $\overline{m}$ denote the negative values of m, the transformed expansion coefficients for the first molecular subset are as before $$\{\ddot{a}_{nlm}^{\tau,\sigma}(R = R_i, \alpha_1 = 0, \beta_1 = \beta_{1j}, \gamma_1 = \gamma_{1k})\}$$

but the rotated expansion coefficients for the second molecular subset are at the sample point, $$\{\hat{b}_{lmn}^{\tau,\sigma}(\alpha_2 = 0, \beta_2 = \beta_{2j}, \gamma_2 = \gamma_{2k})\}.$$

In the second step, the score is given by, $$S(R, \beta_1, \gamma_1, \alpha_2, \beta_2, \gamma_2) = \sum_{m=-l}^{m=+l} (\Lambda_m^+ \cos(m\alpha_2) + \Lambda_m^- \sin(\overline{m}\alpha_2)) \quad \text{[Eqn. 26]}$$

where m is the azimuthal quantum number, and $\alpha_2$ represents the third rotation operator. Splitting off the third rotation operator in the above manner reduces the total computation significantly.

As described above, a plurality of shape complementarity scores is generated for each existing element of the set of sampled configurations of the molecular combination, and can be generated in any order. In FIG. 8, this represents a sampling of shape complementarity scores over a six-dimensional space representing the relative positions and orientations of the two molecular subsets as given by $\{(R=R_i, \beta_1=\beta_{1j}, \gamma_1=\gamma_{1k}, \alpha_2=\alpha_{2l}, \beta_2=\beta_{2m}, \gamma_2=\beta_{2n})\}$ where $\{R_i\}$ refers to the elements of the axial sampling scheme of step 310, $\{\beta_{1j},\gamma_{1k}\}$ to the elements of the first spherical sampling scheme of step 312, $\{\beta_{2m},\gamma_{2n}\}$ to the elements of the second spherical sampling scheme, (also of step 312), and $\{\alpha_{2l}\}$ to the elements of the angular sampling scheme of step 314.

For reasonable sampling resolution for each sampling scheme, the total number of shape complementarity scores can be very large. For example, if there are 50 axial sample points, each 1 Å apart, 1000 first spherical sample points from an icosahedral mesh, 1000 second spherical sample points from an icosahedral mesh, and 100 angular sample points, this represents approximately five billion scores. However, reduction of the sampling resolution can lead to unacceptable inaccuracies in the final prediction and characterization of the optimal binding mode for the two molecular subsets. Thus efficiency in performing the repeated computation of Eqn. 24 for $S=S(R, \beta_1,\gamma_1, \alpha_2, \beta_2,\gamma_2)$ for each sampled configuration is important, whether it be accomplished via means of computer software and/or hardware. In other embodiments, as discussed below, the method provides for further increased computational efficiency when considering the screening of a collection of second molecular subsets against the same first molecular subset 410.

In order to increase efficiency when there is more prior knowledge about the first molecular subset 410, in one embodiment, the computation of shape complementarity scores is restricted to a subset of the possible orientations of the first molecular subset by constraining the first spherical sample points to a subset of the surface of the unit sphere. In another embodiment, the computation of shape complementarity scores can be restricted to a subset of the possible orientations of the first molecular subset by placing limits on the pitch and yaw Euler angles for the first molecular subset. In another embodiment, when the first molecular subset 410 includes a biopolymer with one or more known active sites, the computation of shape complementarity scores is restricted to a subset of possible orientations of the first molecular subset by constraining the first spherical sample points to those that lie with the active site.

In the context of large-scale screening, often little prior knowledge is known about the binding kinetics of the second molecular subset, however, if prior knowledge is available, in one embodiment the computation of shape complementarity scores is further restricted to a subset of the possible orientations of the second molecular subset by placing limits on the angular sample points for the second molecular subset and/or placing limits on the roll, pitch, and yaw Euler angles for the second molecular subset.

Figure 14:
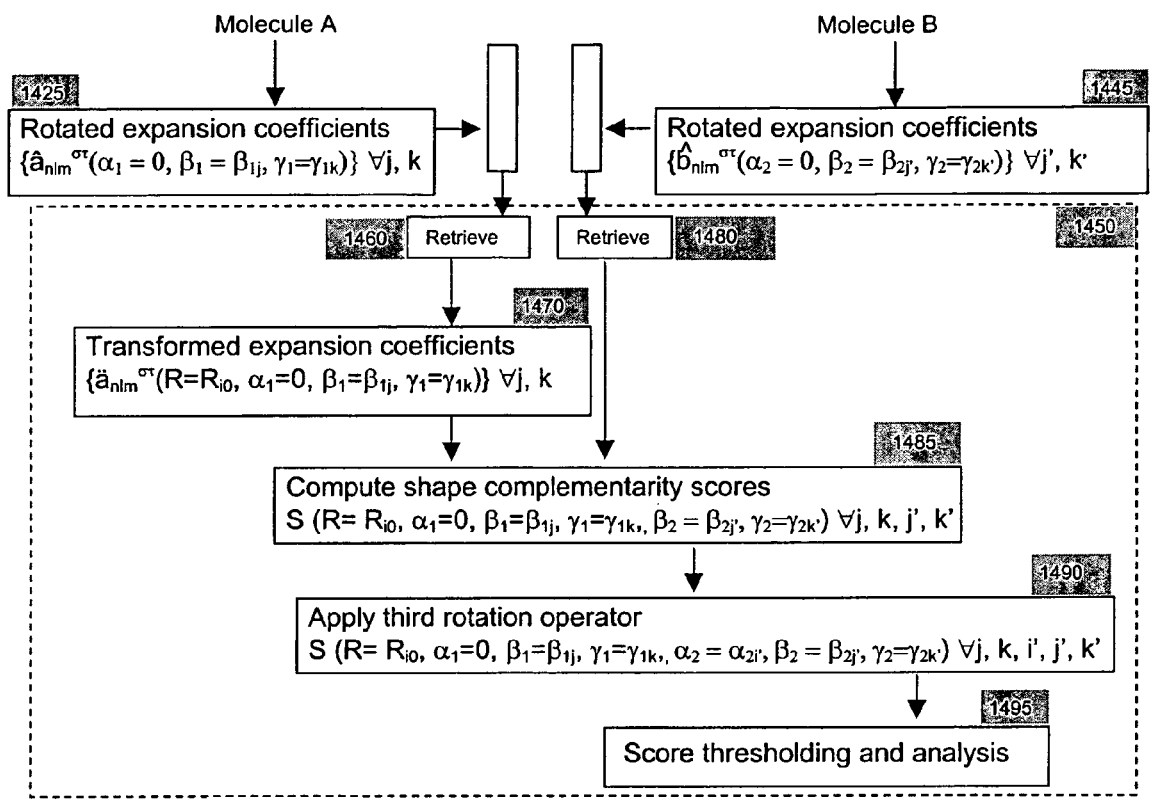
FIG. 14 shows a flow diagram of a method for analyzing a molecular combination comprising two molecular subsets based on computations of shape complementarity, by first performing a rotation operation on appropriate sets of expansion coefficients before applying a translation operator in order to generate sets of transformed expansion coefficients, as per the work of Ritchie et al.

In order to increase computational efficiency regardless of prior knowledge, previous work, such as that of Ritchie et al, has employed a strategy as shown in FIG. 14. Step 1420 corresponds to the direct application of the first rotation operator to the set of reference expansion coefficients for molecular subset 410 in order to generate a set of rotated coefficients, i.e., $$\{\hat{a}_{nlm}^{\tau,\sigma}(\beta_1 = \beta_{1j}, \gamma_1 = \gamma_{1k})\}$$

at each distinct $(\beta_{1j}, \gamma_{1k})$. Optionally, step 1425, more relevant in the context of large-scale screening, shows the complete set of rotated coefficients for molecular subset 410 generated in 1420, corresponding to all first spherical sample points $(\beta_{1j}, \gamma_{1k})$, being subsequently stored on a computer readable and recordable medium.

Step 1440 shows the application of the second rotation operator to the set of reference expansion coefficients for molecular subset 420 in order to generate a set of rotated coefficients, i.e., $$\{\hat{b}_{nlm}^{\tau,\sigma}(\beta_2 = \beta_{2j}, \gamma_2 = \gamma_{2k})\}$$

at each distinct $(\beta_{2j}, \gamma_{2k})$. Optionally, step 1445, shows the complete set of rotated coefficients for molecular subset 420 generated in step 1440, corresponding to all second spherical sample points $(\beta_{2j}, \gamma_{2k})$, being subsequently stored on a computer readable and recordable medium.

Step 1450 then shows the entire set of shape complementarity scores being constructed for one specifically chosen axial sample point, $R_{i0}$, in the following manner. First all of the rotated expansion coefficients for molecular subset 410 are retrieved from the storage medium of step 1425 in step 1460 (optional, only needed if step 1425 was performed). Then the translation operator corresponding to a displacement by $R=R_{i0}$, is applied to each and every retrieved set of rotated coefficients in step 1470, generating corresponding sets of transformed coefficients for the internal and external volume functions of molecular subset 410, i.e., $$\{\hat{a}_{nlm}^{\tau,\sigma}(R = R_{i0}, \beta_1 = \beta_{ij}, \gamma_1 = \gamma_{1k})\}$$

for one axial sample point, $R_{i0}$, and for all first spherical sample points $(\beta_{1j}, \gamma_{1k})$. Then all of the rotated expansion coefficients for molecular subset 420 are retrieved from the storage medium of step 1445 in step 1480 (optional, only needed if step 1445 was performed, but if not then step 1450 must still occur before proceeding).

Then continuing with the description of step 1450, the set of transformed coefficients from step 1470 and the set of rotated coefficients from step 1480 (or step 1440 if no storage) are combined in step 1485 in order to compute shape complementarity scores corresponding to $\{S_{(i0,j,k,m,n)} = S(R=R_{i0}, \beta_1=\beta_{1j}, \gamma_1=\gamma_{1k}, \beta_2=\beta_{2m}, \gamma_2=\gamma_{2n})\}$ for one axial sample point, $R_{i0}$, all first spherical sample points $(\beta_{2j}, \gamma_{2k})$, and all second spherical sample points $(\beta_{2j}, \gamma_{2k})$, according to Eqn. 24 or an alternative form such as in Eqn. 25. In step 1490, only necessary if step 1485 utilized Eqn. 25 as opposed to 24, the third rotation operator is applied directly to the scores obtained in step 1485, according to Eqn. 26, in order to construct further scores corresponding $\{S_{(i0,j,k,l,m,n)} = S(R=R_{i0}, \beta_1=\beta_{1j}, \alpha_2=\alpha_{2l}, \beta_2=\beta_{2m}, \gamma_2=\gamma_{2n})\}$ for one axial sample point, $R_{i0}$, all first spherical sample points $(\beta_{2j}, \gamma_{2k})$, all second spherical sample points $(\beta_{2j}, \gamma_{2k})$, and all angular sample points $(\alpha_{2l})$ describing rotation of molecular subset 420 around the z-axis of the joint coordinate system. In step 1495, the resultant scores from step 1490, or step 1485 if 1490 was skipped, are delivered for thresholding and passing scores archived for future examination. The entirety of step 1450 (including steps 1460, 1470, 1480, 1485, 1490, and 1495) is then repeated for another distinct axial sample point, $R_{i1}$, and so on for all axial sample points in $\{R_i\}$.

In the above procedure outlined in FIG. 14, step 1490 can be skipped if instead the third rotation operator was included in step 1440 as previously discussed. Moreover, steps 1425 and 1445 are optional, in that the coefficients need not be stored (and thus not retrieved so steps 1460 and 1480 become superfluous), in which case all subsequent steps which use the retrieved sets of coefficients of steps 1460 and 1480 must instead have the sets of coefficients ready at hand. However, foregoing steps 1425 and/or 1445, is generally impractical since for order of expansion, N>>1, there are simply to many coefficients to allow immediate ('on-the-fly') computation of all the coefficients in a generic software and/or hardware pipeline. It is also possible to apply variants of the FIG. 14 steps that operate on subsets of the sets of expansion coefficients at each stage, as opposed to the complete sets themselves, but overall this will generally not significantly impact the performance of the procedure in FIG. 14.

The procedure in FIG. 14 has a number of computational drawbacks. As will now be detailed, these drawbacks will also have major detrimental impact on any hardware architecture when the order of expansion, N, is large, i.e., N>>1. First, the number of expansion coefficients for one volume function for one molecular subset scales as $O(N^3)$ in terms of the order of the expansion, N. For example for N=25, there are 5525 distinct coefficients, in the set of reference expansion coefficients $\{a_{nlm}\}$ for one volume function for one molecular subset. Thus Eqn. 24, which minimally requires two sets of transformed coefficients for molecular subset 410 (one for $\tau_a$ and one for $\sigma_a$) and two similar rotated sets for molecular subset 420, there are, for N=25, 22, 100 coefficients involved in the calculation of just one shape complementarity score. Granted, a reasonable ordering, when imposed on the iteration of shape complementarity scores through the six-dimensional space of FIG. 8, allows for keeping half the coefficients fixed (e.g., those for molecular subset 410) while computing or retrieving the other half (e.g., those for molecular subset 420) for each new shape complementarity score, but this still represents a significant amount of memory or I/O bandwidth.

Moreover, the application of Eqn. 20 to just one set of reference coefficients (i.e., corresponding to one spherical sample point) is $O(N^4)$ operations, whereas the application of Eqn. 19 to just one set of reference coefficients (i.e., corresponding to one axial sample point) is $O(N^5)$ operations. Assuming that there are $N_{sphere,1}$ first spherical sample points, $N_{sphere,2}$ second spherical sample points, and $N_R$ axial sample points, and that the rotated coefficients for molecular subsets 410 and 420 will be stored on a computer readable and recordable medium and later retrieved, the procedure outlined in FIG. 14 requires $2*N_{sphere,1}*O(N^4)$ operations to generate the rotated coefficients for molecular subset 410 in step 1410, $2*N_{sphere,2}*O(N^4)$ operations to generate the rotated coefficients for molecular subset 420 in step 1440 and $2*N_{sphere,1}*O(N^5)$ operations in step 1470 to generate the transformed coefficients necessary for computing the shape complementarity scores in step 1485. The latter step in 1470 will be repeated $N_R$ times over the course of the entire process leading to $2*N_{sphere,1}*N_R*O(N^5)$ operations for translation of coefficients while steps 1420 and 1440 are performed only once assuming the storage and retrieval steps of 1425, 1445, 1460, and 1480, bringing the total count to $2*(N_{sphere,1}+N_{sphere,2})*O(N^4)+2*N_{sphere,1}*N_R*O(N^5)$.

For example, for $N_{sphere,1}=N_{sphere,2}=1000$, $N_R=50$, and $N=25$, this corresponds to approx. $10^{11-12}$ calculations. In the present example, this is comparable to the number of operations specific to the actual score computation represented by eqns. 25 and 26 in steps 1485 and 1490. For $N_{ang}$ angular sample points for the third rotation operator, the cost of the score calculations alone is $N_{sphere,1}*N_{sphere,2}*N_R*[4*O(N^3)+2*N*N_{ang}]$. This is roughly $1.3\times10^{12}$ operations for $N_{ang}=72$ angular sample points (i.e., $\Delta\alpha_2\approx5°$).

For the purposes of hardware architecture, the storage and bandwidth requirements of the procedure outlined in FIG. 14 are even more costly. In fact, the full set of all rotated coefficients for molecular subsets 410 and 420 represent a significant amount of data. For example for $N_{sphere,1}=N_{sphere,2}=1000$, $N=25$, assuming 32 bits precision for each value, this amounts to more than 700 Mbits, a value generally far too large to store on-chip in registers or SRAM. If instead the data is stored on DRAM or equivalent memory off-chip, the requirements for the memory bandwidth in the retrieval steps 1460 and 1480 are enormous and impractical, unless the hardware pipeline devoted to step 1450 is purposefully slowed to a crawl; also impractical. The prospect of storing the rotated coefficients on an I/O device, such as a disk, is even less appealing due to the low rates of I/O bandwidth relative to memory bandwidth available for general computer and/or specialized hardware systems. This also says nothing of the large amount of data represented by the precalculated values for the translation matrix elements, $K_{nn'll'|m|}$, of Eqn. 23 in step 1470, even exploiting various symmetries on the quantum numbers.

If alternatively, when screening molecular subset 410 against a collection of molecular subsets 420, all sets of transformed coefficients for molecular subset 410 were precomputed and stored off-chip, this would represent roughly 1 billion coefficient values that must be accessed from memory or an I/O device in the present example of $N_{sphere,1}=1000$, $N_R=50$, and $N=25$, for just processing just one pair of molecular subsets; very impractical.

The above drawbacks in terms of both operational cost and especially the storage and retrieval requirements are generally restrictive for any hardware architecture and will in fact severely limit the efficiency of any general computer software and/or hardware system.

Figure 15:
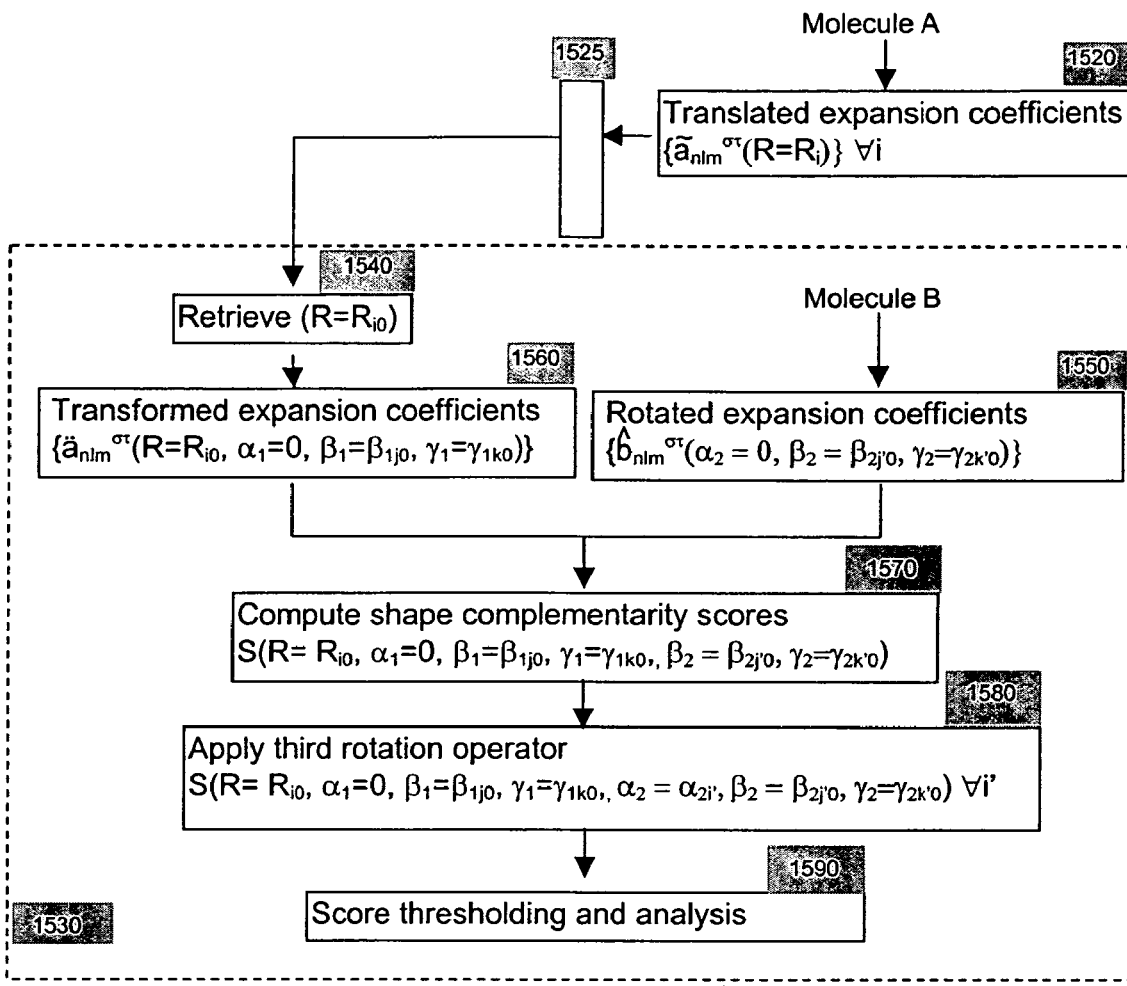
FIG. 15 shows a flow diagram of a novel, and substantially more efficient method, analyzing a molecular combination comprising two molecular subsets based on computations of shape complementarity, by first performing a translation operation on appropriate sets of expansion coefficients before applying a rotation operator in order to generate sets of transformed expansion coefficients, in accordance with embodiments of the present invention.

In order to increase computational efficiency regardless of prior knowledge and to eliminate the drawbacks discussed above, one embodiment of the current invention employs a strategy as shown in FIG. 15. Step 1520 corresponds to the direct application of the translation operator to the set of reference expansion coefficients for molecular subset 410 in order to generate a set of translated coefficients, i.e., $$\{\tilde{a}_{nlm}^{\tau,\sigma}(R=R_i)\}$$

at each distinct axial sample point, $R_i$. Step 1525 shows the complete set of translated coefficients for molecular subset 410 generated in 1520, corresponding to all axial sample points, $\{R_i\}$, being subsequently stored on a computer readable and recordable medium.

In FIG. 15, step 1530 then shows the entire set of shape complementarity scores being constructed for one specifically chosen axial sample point, $R_{i0}$, in the following manner. First all of the translated expansion coefficients for molecular subset 410 corresponding to the chosen axial sample point, $R_{i0}$, are retrieved from the storage medium of step 1525 in step 1540. Then, in step 1550, the second rotation operator is applied to the set of reference expansion coefficients for molecular subset 420 in order to generate a set of rotated coefficients, i.e., $\{b^{\tau,\sigma}_{nlm}(\beta_2=\beta_{2j0}, \gamma_2=\gamma_{2k0})\}$ at a given first spherical sample point distinct $(\beta_{2j0},\gamma_{2k0})$. Then, in step 1560, the first rotation operator corresponding to a specific change in orientation by $(\beta_{1j0}, \gamma_{1k0})$, is applied to each set of translated coefficients retrieved in step 1540, generating corresponding sets of transformed coefficients for the internal and external volume functions of molecular subset 410, i.e., $$\{\tilde{a}_{nlm}^{\tau,\sigma}(R=R_{i0}, \beta_1=\beta_{ij0}, \gamma_1=\gamma_{1k0})\}$$

for one axial sample point, $R_{i0}$, and for one specific first spherical sample point $(\beta_{1j0}, \gamma_{1k0})$.

Then continuing with the description of step 1530, a set of transformed coefficients from step 1560 and a set of rotated coefficients from step 1550 are combined in step 1570 in order to compute a single shape complementarity score corresponding to $\{S_{(i0,j0,k0,m0,n0)}=S(R=R_{i0}, \beta_1=\beta_{1j0}, \gamma_1=\gamma_{1k0}, \beta_2=\beta_{2m0}, \gamma_2=\gamma_{2n0})\}$ for one axial sample point, $R_{i0}$, one first spherical sample point $(\beta_{2j0},\gamma_{2k0})$, and one second spherical sample point $(\beta_{2j0},\gamma_{2k0})$, according to Eqn. 24 or an alternative form such as in Eqn. 25. In step 1580, only necessary if step 1570 utilized Eqn. 25 as opposed to 24, the third rotation operator is applied directly to the scores obtained in step 1570, according to Eqn. 26, in order to construct a set of scores corresponding to $\{S_{(i0,j0,k0,l,m0,n0)}=S(R=R_{i0}, \beta_1=\beta_{1j0}, \gamma_1=\gamma_{1k0}, \alpha_2=\alpha_{2l}, \beta_2=\beta_{2m0}, \gamma_2=\gamma_{2n0})\}$ for one axial sample point, $R_{i0}$, one first spherical sample point $(\beta_{2j0}, \gamma_{2k0})$, one second spherical sample point $(\beta_{2j0}, \gamma_{2k0})$, and all angular sample points $(\alpha_{2l})$ describing rotation of molecular subset 420 around the z-axis of the joint coordinate system. In step 1590, in immediate succession, the resultant scores from step 1580, or step 1570 if 1580 was skipped, are delivered for application of various decision criteria as described above.

Steps 1550, 1560, 1570, 1580, and 1590 are then repeated multiple times in order to generate the entire set of shape complementarity scores for one specifically chosen axial sample point, $R_{i0}$, i.e., $\{S_{(i0,j,k,l,m,n)}=S(R=R_{i0}, \beta_1=\beta_{1j}, \gamma_1=\gamma_{1k}, \alpha_2=\alpha_{2l}, \beta_2=\beta_{2m}, \gamma_2=\gamma_{2n})\}$ for one axial sample point, $R_{i0}$, all first spherical sample points $(\beta_{2j},\gamma_{2k})$, all second spherical sample points $(\beta_{2j},\gamma_{2k})$, and all angular sample points $(\alpha_{2l})$. The number of repetitions of steps 1550 and 1560 depends on the order in which the individual scores in step 1570 are computed. The entirety of step 1530 (including steps 1540, 1550, 1560, 1570, 1580, and 1590) is then repeated for another distinct axial sample point, $R_{i1}$, and so on for all axial sample points in $\{R_i\}$.

In one embodiment, step 1580 can be skipped if instead the third rotation operator was included in step 1550 as part of a composite rotation matrix, as previously discussed. Moreover, in another embodiment, steps 1550 and 1560 may instead calculate sets of coefficients for more than one spherical sample point at a time, depending on the usage of computer readable memory to store intermediate results.

In another embodiment, since it is impractical to perform steps 1550 and 1560 one time for each score generated in 1570, steps 1550 and 1560 are performed concurrently A times and pipelined in front of step 1570, in order to feed the input requirements for generating A*A scores in step 1570. In another embodiment step 1550 is performed A times and step 1560 is performed B times, the results of which are stored in an intermediate computer readable memory and pipelined in front of step 1570, in order to feed the input requirements for generating A*B scores in step 1570.

In yet another embodiment, step 1540 is performed in a pipelined fashion using an intermediate computer addressable memory so that the sets of translation coefficients corresponding to the next axial sample point are read in concurrently while performing one pass of step 1530. In another embodiment, for the purposes of hardware architecture, the entire set of translated coefficients generated in step 1520 are directly stored in on-chip computer readable memory in step 1525 as opposed to off-chip computer readable memory. In another embodiment, step 1530 performs the calculation of shape complementarity scores for more than one axial sample point in parallel and in a concurrent fashion. In another embodiment step 1525 is skipped, and the translation operator is directly applied before the initiation of one pass through step 1530.

The benefits of the procedure in FIG. 15 manifest themselves in terms of both reduced number of operations and reduced storage and memory or I/O bandwidth. In comparison to the procedure outlined in FIG. 14, assuming that there are $N_{sphere,1}$ first spherical sample points, $N_{sphere,2}$ second spherical sample points, and $N_R$ axial sample points, and that the translated coefficients for molecular subsets 410 and 420 will be stored on a computer readable and recordable medium and later retrieved, now $2*N_R*O(N^5)$ operations are needed to perform step 1510 and $2*(N_{sphere,1}+N_{sphere,2})*O(N^4)$ operations to perform steps 1550 and 1560 for one pass through step 1530. This brings the total count to $2*N_R*(N_{sphere,1}+N_{sphere,2})*O(N^4)+2*N_R*O(N^5)$, which will be much smaller for large values of the expansion order N.

For example, for $N_{sphere,1}=N_{sphere,2}=1000$, $N_R=50$, and N=25, this corresponds to less than $10^{10}$ calculations, in comparison to the $10^{11-12}$ of the procedure in FIG. 14. In software, this translates into reduced run time, and in hardware translates into either reduced run-time and/or reduced die area, which can affect chip yields and power requirements.

But far more striking is the reduction in terms of both memory storage and memory and I/O bandwidth, especially critical for hardware designs. The entire set of translated coefficients for all axial sample points in the present example with $N_R=50$, N=25, and 32 bit precision is <18 Mbits as opposed to the 700+ Mbits used up by the rotated coefficients of the procedure in FIG. 14. As discussed above, this data representing the entire set of translated coefficients can either be stored off-chip or even stored in an on-chip memory for faster access. This amount of data represents a very small comparative memory bandwidth, even if stored off-chip. Also the memory or I/O bandwidth requirements for retrieving pre-computed translation matrix elements are significantly reduced. Moreover, the effective use of pre-computation of coefficients, especially valuable when screening one molecular subset against a series of other molecular subsets, becomes viable. Lastly, efficient, pipeline-able hardware architectures become possible, since the required amount of storage in on-chip memory and the amount of memory bandwidth are within the capabilities of current memory and bus technology.

Embodiments of the present invention provide for pre-computation of translation expansion coefficients. These translation expansion coefficients can then be stored on a computer-readable medium. Then before computing shape complementarity scores, the stored translated expansion coefficients can be retrieved as needed for each distinct axial sample point, corresponding to a different relative translation of the two molecular subsets. In the context of assessing a likelihood of molecular combination for a pair of molecular subsets, the translation can be applied once to a set of reference coefficients for molecular subset 410 for a finite number of translational values, performed off-chip, and the results stored for subsequent use in screening against a series of second molecular subsets 420 selected from a molecule library or other collection. The molecule library is generally a database, plurality of databases, or other storage media in which a plurality of digital representations of molecular subsets are stored.

Those skilled in the art should be aware that the methodology described above is applicable to a wide variety of correlation-based score calculations. In addition to the volume-based shape complementarity score calculations described above, the methods are equally applicable to many other correlation-based score calculations based on volumetric functions associated with molecular subsets in the context of a high density search over relative orientations and positions of the two molecular subsets.

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. A method of determining whether a first molecular subset is a lead candidate for a target biomolecule, wherein the target biomolecule is represented as a second molecular subset, the method comprising:
providing a basis expansion of volume functions of the molecular subsets by:
defining a molecular surface for each molecular subset based on locations of a plurality of surface atoms of the corresponding molecular subset;
generating separately first and second internal volume functions as representations of subsets of corresponding volumes enclosed by the first and second molecular surfaces;
generating separately first and second external volume functions as representations of subsets of corresponding volumes external to the first and second molecular surfaces;
representing each of the internal and external volume functions by a respective reference set of expansion coefficients of a basis expansion, where the first reference set is for the first internal and external volume functions and the second reference set is for the second internal and external volume functions;
defining coordinate based representations for each molecular subset using separate corresponding first and second coordinate systems;
placing the coordinate based representations of the first and second molecular subsets in a joint coordinate system with separate frames for each molecular subset centered at respective molecular centers of each molecular subset, with an intermolecular axis defined there between;

defining rigid body transformations and sampling schemes by:
  providing a translation operator associated with an axial sampling scheme comprising a plurality of axial sample points distributed along the intermolecular axis, reflecting discretized relative translation of the first molecular subset with respect to the second molecular subset in the joint coordinate system;
  providing a first rotation operator associated with a first spherical sampling scheme comprising a plurality of spherical sample points distributed on the surface of a sphere centered on the first molecular subset;
  providing a second rotation operator associated with a second spherical sampling scheme comprising a plurality of spherical sample points distributed on the surface of a sphere centered on the second molecular subset;
  providing a third rotation operator associated with an angular sampling scheme comprising a plurality of angular sample points distributed on a circumference of a circle orthogonal to the intermolecular axis;
defining a shape complementarity score for a molecular configuration, the shape complementarity score representing an overlap between the internal volume function of the first molecular subset with the external volume function of the second molecular subset and the internal volume function of the second molecular subset with the external volume function of the first molecular subset at a given relative position and orientation of the first and second molecular subsets in the joint coordinate system;
for every axial sample point from the axial sampling scheme:
  constructing, with a configuration data transformation engine that includes at least one suitably programmed microprocessor, at least one application specific integrated circuit (ASIC), or at least one field programmable gate array (FPGA), or any combination thereof, a set of translated expansion coefficients for the first molecular subset, corresponding to a given axial sample point, by applying a corresponding translation operator to the first reference set of expansion coefficients for both the internal and external volume functions for the first molecular subset;
storing all the sets of translated expansion coefficients for the first molecular subset on a recordable media;
after storing all the sets of translated expansion coefficients, for each axial sample point from the axial sampling scheme, with a shape complementarity engine that includes at least one suitably programmed microprocessor, at least one ASIC, or at least one FPGA, or any combination thereof:
  a) retrieving, from the recordable media, the corresponding set of translated expansion coefficients for the chosen axial sample point;
  b) constructing a set of transformed expansion coefficients for the first molecular subset, corresponding to a set of all configurations prescribed by the Cartesian product of the chosen axial sample point and the spherical sample points from the first spherical sampling scheme, by applying the first rotation operator to the set of translated expansions coefficients;
  c) constructing a set of transformed expansion coefficients for the second molecular subset, corresponding to a set of all configurations prescribed by the Cartesian product of the spherical sample points from the second spherical sampling scheme and the angular sample points from the angular sampling scheme, by applying in succession the second and third rotation operators to the second reference set of expansion coefficients for both the internal and external volume functions for the second molecular subset; and
  d) computing the defined shape complementarity score in terms of the set of transformed expansion coefficients for the first molecular subset, and the set of transformed expansion coefficients for the second molecular subset corresponding to each of a set of sampled configurations associated with the chosen axial sample point; and
  storing the plurality of shape complementarity scores.

2. The method of claim 1, wherein the first internal volume function for the first molecular subset is defined as a union of a set of kernel functions, each kernel function associated with one of the atoms and bonds in the first molecular subset, wherein each kernel function might be dependent on the chemical identity of the associated atom or bond, wherein the kernel function might be dependent on the location of the associated atom or bond within a chemical group and wherein the kernel function associated with an atom might be nonzero for positions within a Van der Waals sphere centered on the atom and zero otherwise.

3. The method of claim 2, wherein the first external volume function for the first molecular subset represents a volume occupied by a probe sphere having a center which moves along a portion of the solvent accessible surface of the first molecular subset and wherein the probe sphere has a radius which might remain constant or might vary as a function of location on the molecular surface.

4. The method of claim 1, wherein the coordinate based representation of the first molecular subset is defined using a spherical, cylindrical or Cartesian coordinate system.

5. The method of claim 1, wherein the molecular center of the first molecular subset is a center of mass or a centroid of the first molecular subset.

6. The method of claim 1, wherein the joint coordinate system used in moving or rotating the coordinate based representations of the first molecular subset and the second molecular subset relative to one another is different from the joint coordinate system used in the final calculations of the shape complementarity scores.

7. The method of claim 1, wherein an order of the basis expansion used in representing both the internal and external volume functions for the first molecular subset has a finite value and where the finite value for the order of the basis expansion might be predetermined.

8. The method of claim 7, where the finite value for the order of the basis expansion is adaptively determined based on a quantitative analysis of basis expansion errors for trial values of the order of the basis expansion.

9. The method of claim 1, wherein the basis expansion used in representing each of the internal and external volume functions is a radial/spherical harmonics basis expansion comprising a plurality of basis functions defined as products of a set of orthonormal radial basis functions and a set of spherical harmonics basis functions.

10. The method of claim 9, wherein the radial basis functions include a mutually orthonormal set of basis functions which depend on the radius in a spherical coordinate system centered on the molecular center of the first molecular subset.

11. The method of claim 10, wherein the radial basis functions include scaled or unscaled Laguerre polynomial-based radial basis functions.

12. The method of claim 9, wherein the spherical harmonics basis functions are real-valued.

13. The method of claim 9, wherein the radial/spherical harmonics basis expansion has a finite value for the order of the expansion and the expansion coefficients are discretized radial/spherical harmonic expansion coefficients.

14. The method of claim 1, wherein different orientations of the coordinate based representation of the first molecular subset with respect to the frame located at the molecular center of the first molecular subset are represented by a set of at least two of three Euler angles representing roll, pitch, and yaw.

15. The method of claim 14, wherein:
the z-axes of the separate frames for each molecular subset are aligned with the intermolecular axis,
the roll Euler angle for the first molecular subset, representing a change in orientation of the first molecular subset with respect to the z-axis of the first molecular subset's frame, is disregarded,
different orientations of the first molecular subset are represented by a pair of Euler angles, namely the pitch and yaw Euler angles, and
different orientations for the second molecular subset are represented by a full set of three Euler angles, including the roll Euler angle for the second molecular subset, representing a change in orientation of the second molecular subset with respect to the z-axis of the frame of the second molecular subset.

16. The method of claim 15, wherein the computation of shape complementarity scores is restricted to a subset of the possible orientations of the second molecular subset by placing limits on the roll, pitch, and yaw Euler angles for the second molecular subset.

17. The method of claim 15, wherein the first rotation operator for the first molecular subset is represented by a matrix function of the pitch and yaw Euler angles for the first molecular subset, the second rotation operator for the second molecular subset is represented by a matrix function of the pitch and yaw Euler angles for the second molecular subset, and the third rotation operator for the second molecular subset is represented by a matrix function of the roll Euler angle for the second molecular subset.

18. The method of claim 17, wherein the basis expansion for each molecular subset is the radial/spherical harmonics basis expansion comprising a plurality of basis functions defined as products of a set of orthonormal radial basis functions and a set of spherical harmonics basis functions and the first and second rotation operators are Wigner rotation matrices with indices specified in terms of the quantum numbers of the basis expansion for both molecular subsets and the roll Euler angle is set to zero.

19. The method of claim 14, wherein the first rotation operator for the first molecular subset is represented by a matrix function of the roll, pitch, and yaw Euler angles for the first molecular subset.

20. The method of claim 14, wherein the basis expansion of the first molecular subset is a radial/spherical harmonics basis expansion comprising a plurality of basis functions defined as products of a set of radial basis functions and a set of spherical harmonics basis functions, and the first rotation operator is a Wigner rotation matrix with indices specified in terms of quantum numbers of the radial/spherical harmonics basis expansion.

21. The method of claim 14, wherein the computation of shape complementarity scores is restricted to a subset of the possible orientations of the first molecular subset by placing limits on the pitch and yaw Euler angles for the first molecular subset.

22. The method of claim 1, wherein the two successive applications of the second and third rotation operators to the coordinate based representation of the second molecular subset are combined into the application of a single combined rotation operator.

23. The method of claim 22, wherein the combined rotation operator is represented by a matrix function of roll, pitch, and yaw Euler angles for the second molecular subset and said matrix function might be a Wigner rotation matrix with indices specified in terms of quantum numbers of the basis expansion for the second molecular subset.

24. The method for claim 1, wherein the sets of transformed expansion coefficients of the second molecular subset are generated by applying only the second rotation operator, and the resultant shape complementarity scores are subjected to a matrix multiplication representing the third rotation operator in order to generate a plurality of shape complementarity scores that represent the set of angular sample points for the second molecular subset.

25. The method for claim 24, wherein the basis expansion for each molecular subset is the radial/spherical harmonics basis expansion comprising a plurality of basis functions defined as products of a set of orthonormal radial basis functions and a set of spherical harmonics basis functions and the matrix function representing the third rotation operator as applied to shape complementarity scores is a function of the roll Euler angle of the second molecular subset, with indices specified by azimuthal quantum numbers of the basis expansion for both molecular subsets.

26. The method of claim 1, wherein the translation operator applied to the coordinate based representation of the first molecular subset is a matrix function of the displacement along the intermolecular axis between the two molecular subsets.

27. The method of claim 1, wherein the coordinate based representation of the internal volume function of the first molecular subset is generated for a specific coordinate system, stored on a recordable medium as a set of discrete values, each discrete value representing a portion of the information representing the coordinate based representation of the internal volume function of the first molecular subset, then the stored discrete values retrieved as needed when constructing a set of reference expansion coefficients for the internal volume function of the first molecular subset, having first converted each discrete value into another value representing the corresponding portion of the information representing the coordinate based representation of the internal volume function of the first molecular subset in a coordinate system used to define the basis expansion, the conversion being accomplished by a suitable coordinate transformation.

28. The method of claim 1, wherein the coordinate based representation of the external volume function of the first molecular subset is generated for a specific coordinate system, stored on a recordable medium as a set of discrete values, each discrete value representing a portion of the information representing the coordinate based representation of the external volume function of the first molecular subset, then the stored discrete values retrieved as needed when constructing a set of reference expansion coefficients for the external volume function of the first molecular subset, having first converted each discrete value into another value representing the corresponding portion of the information representing the coordinate based representation of the external volume function of the first molecular subset in a coordinate system used to define the basis expansion, the conversion accomplished by a suitable coordinate transformation.

29. The method of claim 1, wherein either the axial and/or the first spherical sampling schemes for the first molecular subset are regular sampling schemes, and wherein the angular and/or the second spherical sampling scheme for the second molecular subset are regular sampling schemes.

30. The method of claim 1, wherein either the axial and/or the first spherical sampling schemes for the first molecular subset are irregular sampling schemes.

31. The method of claim 1, further comprising:
defining a molecular shape for each molecular subset based on a plurality of atoms and bonds forming the corresponding molecular subset or a portion thereof, wherein endpoints of the axial sampling scheme for the first molecular subset are assigned based on geometric analysis of the molecular shapes of both molecular subsets, wherein the geometric analysis might include determination of the maximal spatial extent of both molecular surfaces.

32. The method of claim 1, wherein the angular and/or the second spherical sampling scheme for the second molecular subset are irregular sampling schemes.

33. The method of claim 1, wherein the shape complementarity score is further defined to include a negative of an overlap of the first and second internal volume functions, and wherein the overlap of the first and second internal volume functions in the definition of a shape complementarity score is multiplied by a real-valued constant so that its contribution to the shape complementarity score is opposite in sign to the positive overlap of the internal volume function of one molecular subset and the external volume function of the other molecular subset.

34. The method of claim 1, wherein the computation of shape complementarity scores is restricted to a subset of the possible orientations of the first molecular subset by constraining the first spherical sample points to a subset of the surface of the unit sphere.

35. The method of claim 34, wherein the first molecular subset includes a biopolymer with one or more known active sites, and the computation of shape complementarity scores is restricted to a subset of possible orientations of the first molecular subset by constraining the first spherical sample points to those that lie within the active sites.

36. The method of claim 1, wherein the computation of shape complementarity scores is further restricted to a subset of the possible orientations of the second molecular subset by placing limits on angular sample points for the second molecular subset.

37. The method of claim 1, wherein the set of computed shape complementarity scores is subjected to a set of decision criteria in order to select the optimal shape complementarity scores at corresponding positions and orientations of the two molecular subsets.

38. The method of claim 37, wherein the decision criteria is based on a preset numerical threshold.

39. The method of claim 37, wherein the decision criteria is based on an adaptive threshold dependent on observed statistics of the shape complementarity scores as the shape complementarity scores are generated.

40. The method of claim 37, wherein the decision criteria is based on a cluster analysis of the shape complementarity scores.

41. The method of claim 1, wherein the plurality of sets of shape complementarity scores are calculated at one value for the order of the expansion, the shape complementarity scores are quantitatively analyzed, and a further plurality of shape complementarity scores are calculated at a higher value for the order of the expansion based on results of an intervening analysis.

42. The method of claim 41, wherein the second plurality of shape complementarity scores is computed only at sample points for which an initial shape complementarity score satisfies a set of decision criteria in order to select the optimal shape complementarity scores at corresponding positions and orientations of the two molecular subsets.

43. The method of claim 1, wherein the first molecular surface for the first molecular subset is a solvent accessible molecular surface.

44. The method of claim 1, wherein the first molecular subset includes a biopolymer or a part of a biopolymer.

45. The method of claim 1, wherein the first molecular subset includes a synthetic compound, a chemical group, a medicinal compound or a carbohydrate.

46. The method of claim 1 where the analysis of combination is determined between a first molecular subset and each of a plurality of second molecular subsets selected from a molecule library.

47. The method of claim 46, wherein the set of computed shape complementarity scores is further subjected to a set of decision criteria in order to generate an optimal shape complementarity score, or equivalent measure, representing the configuration with the maximal shape complementarity for each combination and the resultant optimal shape complementarity scores are then ranked according to a sorting criteria in order to prioritize those second molecular subsets selected from the molecule library that exhibit high shape complementarity with the first molecular subset.

48. The method of claim 46, wherein the plurality of computed shape complementarity scores are stored on a recordable medium, the method being repeated for further molecular combinations featuring second molecular subsets selected from the molecule library, and a cluster analysis is performed on the set of stored, shape complementarity scores to perform an analysis of each molecular combination of the first molecular subset with each second molecular subset selected from the molecule library.

49. A computer readable storage medium storing executable instructions for directing one or more processors to determine whether a first molecular subset is a lead candidate for a target biomolecule, wherein the target biomolecule is represented as a second molecular subset, the instructions comprising:
providing a basis expansion of volume functions of the molecular subsets by:
defining a molecular surface for each molecular subset based on locations of a plurality of surface atoms of the corresponding molecular subset;
generating separately first and second internal volume functions as representations of subsets of corresponding volumes enclosed by the first and second molecular surfaces;
generating separately first and second external volume functions as representations of subsets of corresponding volumes external to the first and second molecular surfaces;
representing each of the internal and external volume functions by a respective reference set of expansion coefficients of a basis expansion, where the first reference set is for the first internal and external volume functions and the second reference set is for the second internal and external volume functions;

defining coordinate based representations for each molecular subset using separate corresponding first and second coordinate systems;

placing the coordinate based representations of the first and second molecular subsets in a joint coordinate system with separate frames for each molecular subset centered at respective molecular centers of each molecular subset, with an intermolecular axis defined there between;

defining rigid body transformations and sampling schemes by:

providing a translation operator associated with an axial sampling scheme comprising a plurality of axial sample points distributed along the intermolecular axis, reflecting discretized relative translation of the first molecular subset with respect to the second molecular subset in the joint coordinate system;

providing a first rotation operator associated with a first spherical sampling scheme comprising a plurality of spherical sample points distributed on the surface of a sphere centered on the first molecular subset;

providing a second rotation operator associated with a second spherical sampling scheme comprising a plurality of spherical sample points distributed on the surface of a sphere centered on the second molecular subset;

providing a third rotation operator associated with an angular sampling scheme comprising a plurality of angular sample points distributed on a circumference of a circle orthogonal to the intermolecular axis;

defining a shape complementarity score for a molecular configuration, the shape complementarity score representing an overlap between the internal volume function of the first molecular subset with the external volume function of the second molecular subset and the internal volume function of the second molecular subset with the external volume function of the first molecular subset at a given relative position and orientation of the first and second molecular subsets in the joint coordinate system;

for every axial sample point from the axial sampling scheme:

constructing a set of translated expansion coefficients for the first molecular subset, corresponding to a given axial sample point, by applying a corresponding translation operator to the first reference set of expansion coefficients for both the internal and external volume functions for the first molecular subset;

after storing all the sets of translated expansion coefficients, storing all the sets of translated expansion coefficients for the first molecular subset on a recordable media;

for each axial sample point from the axial sampling scheme:

a) retrieving, from the recordable media, the corresponding set of translated expansion coefficients for the chosen axial sample point;

b) constructing a set of transformed expansion coefficients for the first molecular subset, corresponding to a set of all configurations prescribed by the Cartesian product of the chosen axial sample point and the spherical sample points from the first spherical sampling scheme, by applying the first rotation operator to the set of translated expansions coefficients;

c) constructing a set of transformed expansion coefficients for the second molecular subset, corresponding to a set of all configurations prescribed by the Cartesian product of the spherical sample points from the second spherical sampling scheme and the angular sample points from the angular sampling scheme, by applying in succession the second and third rotation operators to the second reference set of expansion coefficients for both the internal and external volume functions for the second molecular subset; and d) computing the defined shape complementarity score in terms of the set of transformed expansion coefficients for the first molecular subset, and the set of transformed expansion coefficients for the second molecular subset corresponding to each of a set of sampled configurations associated with the chosen axial sample point; and storing the plurality of shape complementarity scores.

50. A computational modeling system for determining whether a first molecular subset is a lead candidate for a target biomolecule, wherein the target biomolecule is represented as a second molecular subset, wherein the molecular subsets are represented with a basis expansion of volume functions provided by: defining a molecular surface for each molecular subset based on locations of a plurality of surface atoms of the corresponding molecular subset; generating separately first and second internal volume functions as representations of subsets of corresponding volumes enclosed by the first and second molecular surfaces; generating separately first and second external volume functions as representations of subsets of corresponding volumes external to the first and second molecular surfaces; representing each of the internal and external volume functions by a respective reference set of expansion coefficients of a basis expansion, where the first reference set is for the first internal and external volume functions and the second reference set is for the second internal and external volume functions, wherein a coordinate based representations for each molecular subset uses separate corresponding first and second coordinate systems and a joint coordinate system with separate frames for each molecular subset centered at respective molecular centers of each molecular subset, with an intermolecular axis defined there between;

wherein rigid body transformations and sampling schemes include:

a translation operator associated with an axial sampling scheme comprising a plurality of axial sample points distributed along the intermolecular axis, reflecting discretized relative translation of the first molecular subset with respect to the second molecular subset in the joint coordinate system;

a first rotation operator associated with a first spherical sampling scheme comprising a plurality of spherical sample points distributed on the surface of a sphere centered on the first molecular subset;

a second rotation operator associated with a second spherical sampling scheme comprising a plurality of spherical sample points distributed on the surface of a sphere centered on the second molecular subset; and a third rotation operator associated with an angular sampling scheme comprising a plurality of angular sample points distributed on a circumference of a circle orthogonal to the intermolecular axis, the system comprising:

a configuration data transformation circuit configured to construct, for every axial sample point from the axial sampling scheme, a set of translated expansion coefficients for the first molecular subset, corresponding to a given axial sample point, by applying a corresponding translation operator to the first reference set of expansion coefficients for both the internal and external volume functions for the first molecular subset, the configuration data transformation circuit including at least one suitably programmed microprocessor, at least one application specific integrated circuit (ASIC), or at least one field programmable gate array (FPGA), or any combination thereof;

a recordable media that stores all the sets of translated expansion coefficients for the first molecular subset;

a shape complementarity circuit that includes at least one suitably programmed microprocessor, at least one ASIC, or at least one FPGA, or any combination thereof and that, after all the sets of translated expansion coefficients are stored in the recordable media, is configured to, for each axial sample point from the axial sampling scheme:
  a) retrieve, from the recordable media, the corresponding set of translated expansion coefficients for the chosen axial sample point;
  b) construct a set of transformed expansion coefficients for the first molecular subset, corresponding to a set of all configurations prescribed by the Cartesian product of the chosen axial sample point and the spherical sample points from the first spherical sampling scheme, by applying the first rotation operator to the set of translated expansions coefficients;
  c) construct a set of transformed expansion coefficients for the second molecular subset, corresponding to a set of all configurations prescribed by the Cartesian product of the spherical sample points from the second spherical sampling scheme and the angular sample points from the angular sampling scheme, by applying in succession the second and third rotation operators to the second reference set of expansion coefficients for both the internal and external volume functions for the second molecular subset; and
  d) compute the defined shape complementarity score in terms of the set of transformed expansion coefficients for the first molecular subset, and the set of transformed expansion coefficients for the second molecular subset corresponding to each of a set of sampled configurations associated with the chosen axial sample point, wherein the shape complementarity score represents an overlap between the internal volume function of the first molecular subset with the external volume function of the second molecular subset and the internal volume function of the second molecular subset with the external volume function of the first molecular subset at a given relative position and orientation of the first and second molecular subsets in the joint coordinate system; and a combination post-processor circuit that determines whether the first molecular subset is a lead candidate based on the shape complementarity scores.

51. The method claim 1, wherein at least one of the shape complementarity scores is used to determine whether the first molecular subset is a lead candidate.

52. The computer readable medium of claim 49, wherein at least one of the shape complementarity scores is used to determine whether the first molecular subset is a lead candidate.

* * * * *